(12) United States Patent
Chang et al.

(10) Patent No.: US 10,495,644 B2
(45) Date of Patent: Dec. 3, 2019

(54) METHODS AND SYSTEMS FOR CANCER DIAGNOSIS AND PROGNOSIS

(71) Applicant: ACADEMIA SINICA, Taipei (TW)

(72) Inventors: Ying-Chih Chang, Taipei (TW); Jr-Ming Lai, Taipei (TW); Jen-Chia Wu, Taipei (TW); Huai-Lu Chen, Taipei (TW); Hung-Jen Shao, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/781,165

(22) PCT Filed: Apr. 1, 2015

(86) PCT No.: PCT/US2015/023956
§ 371 (c)(1),
(2) Date: Sep. 29, 2015

(87) PCT Pub. No.: WO2015/153816
PCT Pub. Date: Oct. 8, 2015

(65) Prior Publication Data
US 2017/0219593 A1 Aug. 3, 2017

Related U.S. Application Data

(60) Provisional application No. 61/973,348, filed on Apr. 1, 2014, provisional application No. 61/975,699, filed on Apr. 4, 2014.

(51) Int. Cl.
*G01N 33/574* (2006.01)
*B01L 3/00* (2006.01)
*G01N 33/543* (2006.01)

(52) U.S. Cl.
CPC .. *G01N 33/57492* (2013.01); *B01L 3/502769* (2013.01); *G01N 33/54366* (2013.01); *B01L 2200/0673* (2013.01); *B01L 2300/0681* (2013.01); *B01L 2300/0816* (2013.01); *B01L 2400/0406* (2013.01); *B01L 2400/0487* (2013.01)

(58) Field of Classification Search
None
See application file for complete search history.

(56) References Cited

U.S. PATENT DOCUMENTS

| | | |
|---|---|---|
| 3,784,015 A | 1/1974 | Kasten |
| 5,147,606 A | 9/1992 | Charlton et al. |
| 5,554,686 A | 9/1996 | Frisch, Jr. et al. |
| 5,646,001 A | 7/1997 | Terstappen et al. |

(Continued)

FOREIGN PATENT DOCUMENTS

| | | |
|---|---|---|
| CN | 1646912 A | 7/2005 |
| CN | 1731901 A | 2/2006 |

(Continued)

OTHER PUBLICATIONS

Balic, et al. Micrometastasis: detection methods and clinical importance. Cancer Biomarkers 9.1-6 (2011): 397-419.

(Continued)

*Primary Examiner* — Rebecca L Martinez
(74) *Attorney, Agent, or Firm* — Wilson Sonsini Goodrich & Rosati

(57) ABSTRACT

The disclosure provides for compositions and methods of making and using a foam composition and its utility in clinical applications.

17 Claims, 24 Drawing Sheets

Specification includes a Sequence Listing.

(56) References Cited

U.S. PATENT DOCUMENTS

| | | |
|---|---|---|
| 5,652,148 A | 7/1997 | Doshi et al. |
| 5,707,799 A | 1/1998 | Hansmann et al. |
| 5,837,115 A | 11/1998 | Austin et al. |
| 5,842,787 A | 12/1998 | Kopf-Sill et al. |
| 5,885,470 A | 3/1999 | Parce et al. |
| 5,952,173 A | 9/1999 | Hansmann et al. |
| 6,039,897 A | 3/2000 | Lochhead et al. |
| 6,046,295 A | 4/2000 | Frisch, Jr. et al. |
| 6,153,113 A | 11/2000 | Goodrich et al. |
| 6,271,309 B1 | 8/2001 | Roberts et al. |
| 6,280,622 B1 | 8/2001 | Goodrich et al. |
| 6,322,683 B1 | 11/2001 | Wolk et al. |
| 6,361,749 B1 | 3/2002 | Terstappen et al. |
| 6,365,362 B1 | 4/2002 | Terstappen et al. |
| 6,372,542 B1 | 4/2002 | Martin et al. |
| 6,562,616 B1 | 5/2003 | Toner et al. |
| 6,613,525 B2 | 9/2003 | Nelson et al. |
| 6,620,627 B1 | 9/2003 | Liberti et al. |
| 6,623,982 B1 | 9/2003 | Liberti et al. |
| 6,632,652 B1 | 10/2003 | Austin et al. |
| 6,645,731 B2 | 11/2003 | Terstappen et al. |
| 6,685,841 B2 | 2/2004 | Lopez et al. |
| 6,699,952 B2 | 3/2004 | Chaikof et al. |
| 6,790,366 B2 | 9/2004 | Terstappen et al. |
| 6,790,599 B1 | 9/2004 | Madou |
| 6,844,028 B2 | 1/2005 | Mao et al. |
| 6,887,578 B2 | 5/2005 | Gleason et al. |
| 6,890,426 B2 | 5/2005 | Terstappen et al. |
| 6,955,738 B2 | 10/2005 | Derand et al. |
| 6,960,449 B2 | 11/2005 | Wang et al. |
| 7,005,493 B2 | 2/2006 | Huang et al. |
| 7,056,657 B2 | 6/2006 | Terstappen et al. |
| 7,067,194 B2 | 6/2006 | Mao et al. |
| 7,117,807 B2 | 10/2006 | Bohn et al. |
| 7,150,812 B2 | 12/2006 | Huang et al. |
| 7,190,818 B2 | 3/2007 | Ellis et al. |
| 7,229,760 B2 | 6/2007 | Zohlnhofer et al. |
| 7,276,170 B2 | 10/2007 | Oakey et al. |
| 7,282,350 B2 | 10/2007 | Rao et al. |
| 7,318,902 B2 | 1/2008 | Oakey et al. |
| 7,332,288 B2 | 2/2008 | Terstappen et al. |
| 7,368,163 B2 | 5/2008 | Huang et al. |
| 7,374,944 B2 | 5/2008 | Thompson et al. |
| 7,428,325 B2 | 9/2008 | Douglass et al. |
| 7,431,969 B2 | 10/2008 | Gleason et al. |
| 7,442,515 B2 | 10/2008 | Ratner et al. |
| 7,472,794 B2 | 1/2009 | Oakey et al. |
| 7,485,343 B1 | 2/2009 | Branson et al. |
| 7,501,157 B2 | 3/2009 | Mao et al. |
| 7,531,120 B2 | 5/2009 | Van et al. |
| 7,579,077 B2 | 8/2009 | Dubrow et al. |
| 7,588,550 B2 | 9/2009 | Leonard et al. |
| 7,629,029 B2 | 12/2009 | Mao et al. |
| 7,687,241 B2 | 3/2010 | Chen |
| 7,695,775 B2 | 4/2010 | Kobrin et al. |
| 7,713,689 B2 | 5/2010 | Chilkoti |
| 7,723,112 B2 | 5/2010 | Clarke et al. |
| 7,727,399 B2 | 6/2010 | Leonard et al. |
| 7,735,652 B2 | 6/2010 | Inglis et al. |
| 7,736,891 B2 | 6/2010 | Nelson et al. |
| 7,777,010 B2 | 8/2010 | Logtenberg |
| 7,783,098 B2 | 8/2010 | Douglass et al. |
| 7,785,810 B2 | 8/2010 | Chen |
| RE41,762 E | 9/2010 | Lopez et al. |
| 7,815,922 B2 | 10/2010 | Chaney et al. |
| 7,846,393 B2 | 12/2010 | Tai et al. |
| 7,846,445 B2 | 12/2010 | Schellenberger et al. |
| 7,846,743 B2 | 12/2010 | Tai et al. |
| 7,850,633 B2 | 12/2010 | Leonard et al. |
| 7,855,068 B2 | 12/2010 | Cao |
| 7,855,279 B2 | 12/2010 | Schellenberger et al. |
| 7,863,012 B2 | 1/2011 | Rao et al. |
| 7,879,444 B2 | 2/2011 | Jiang et al. |
| RE42,249 E | 3/2011 | Lopez et al. |
| 7,901,950 B2 | 3/2011 | Connelly et al. |
| RE42,315 E | 5/2011 | Lopez et al. |
| 7,955,704 B2 | 6/2011 | Lowery et al. |
| 7,960,166 B2 | 6/2011 | Vacanti et al. |
| 7,973,136 B2 | 7/2011 | Lazar et al. |
| 7,981,688 B2 | 7/2011 | Stayton et al. |
| 7,985,475 B2 | 7/2011 | Dubrow |
| 7,988,840 B2 | 8/2011 | Huang et al. |
| 7,993,821 B2 | 8/2011 | Chiu et al. |
| 8,008,032 B2 | 8/2011 | Forsyth et al. |
| 8,012,480 B2 | 9/2011 | Lorence |
| 8,021,318 B2 | 9/2011 | Leonard et al. |
| 8,021,614 B2 | 9/2011 | Huang et al. |
| 8,025,854 B2 | 9/2011 | Ohman et al. |
| 8,057,418 B2 | 11/2011 | Korbling et al. |
| 8,063,187 B2 | 11/2011 | Chu et al. |
| D650,091 S | 12/2011 | Odeh |
| 8,069,782 B2 | 12/2011 | Fragala et al. |
| 8,083,706 B2 | 12/2011 | Leonard et al. |
| 8,092,684 B2 | 1/2012 | Leonard et al. |
| 8,093,365 B2 | 1/2012 | Wisniewski et al. |
| 8,097,153 B2 | 1/2012 | Leonard et al. |
| 8,097,162 B2 | 1/2012 | Leonard et al. |
| 8,101,720 B2 | 1/2012 | Lazar et al. |
| 8,158,410 B2 | 4/2012 | Tang et al. |
| 8,158,728 B2 | 4/2012 | Desimone et al. |
| 8,178,602 B2 | 5/2012 | Mao et al. |
| 8,186,913 B2 | 5/2012 | Toner et al. |
| 8,282,799 B2 | 10/2012 | Huang et al. |
| 8,288,116 B2 | 10/2012 | Chen |
| 8,288,170 B2 | 10/2012 | Tai et al. |
| 8,304,230 B2 | 11/2012 | Toner et al. |
| 8,308,699 B2 | 11/2012 | Zhang et al. |
| 8,333,934 B2 | 12/2012 | Cao et al. |
| 8,343,440 B2 | 1/2013 | Yoshioka |
| 8,357,528 B2 | 1/2013 | Vacanti et al. |
| 8,367,314 B2 | 2/2013 | Chilkoti |
| 8,372,579 B2 | 2/2013 | Toner et al. |
| 8,414,806 B2 | 4/2013 | Sun et al. |
| 8,445,225 B2 | 5/2013 | Kuhn et al. |
| 8,481,336 B2 | 7/2013 | Earhart et al. |
| 8,491,516 B2 | 7/2013 | Leonard et al. |
| 8,507,283 B2 | 8/2013 | Stayton et al. |
| 8,545,983 B2 | 10/2013 | Jiang et al. |
| 8,557,528 B2 | 10/2013 | Hauch et al. |
| 8,557,577 B2 | 10/2013 | Hauch et al. |
| 8,574,660 B2 | 11/2013 | Weaver et al. |
| 8,579,117 B2 | 11/2013 | Sturm et al. |
| 8,632,838 B2 | 1/2014 | Roth et al. |
| 8,663,625 B2 | 3/2014 | Stroock et al. |
| 8,669,044 B2 | 3/2014 | Chiu et al. |
| 8,796,184 B2 | 8/2014 | Chilkoti et al. |
| 8,821,812 B2 | 9/2014 | Ohman et al. |
| 8,822,231 B2 | 9/2014 | Melin et al. |
| 8,835,144 B2 | 9/2014 | Jiang et al. |
| 8,895,298 B2 | 11/2014 | Toner et al. |
| 8,911,957 B2 | 12/2014 | Irimia et al. |
| 8,921,102 B2 | 12/2014 | Fuchs et al. |
| 8,980,568 B2 | 3/2015 | Lin et al. |
| 8,986,966 B2 | 3/2015 | Toner et al. |
| 8,986,988 B2 | 3/2015 | Karnik et al. |
| 9,016,221 B2 | 4/2015 | Brennan et al. |
| 9,056,318 B2 | 6/2015 | Bergman et al. |
| 9,140,697 B2 | 9/2015 | Tseng et al. |
| 9,174,222 B2 | 11/2015 | Huang et al. |
| 9,494,500 B2 | 11/2016 | Chang et al. |
| 9,541,480 B2 | 1/2017 | Chang et al. |
| 2001/0031309 A1 | 10/2001 | Lee et al. |
| 2001/0036556 A1 | 11/2001 | Jen |
| 2002/0009759 A1 | 1/2002 | Terstappen et al. |
| 2002/0055093 A1 | 5/2002 | Abbott et al. |
| 2002/0098535 A1 | 7/2002 | Wang et al. |
| 2002/0119482 A1 | 8/2002 | Nelson et al. |
| 2002/0125192 A1 | 9/2002 | Lopez et al. |
| 2002/0141913 A1 | 10/2002 | Terstappen et al. |
| 2002/0160139 A1 | 10/2002 | Huang et al. |
| 2002/0182633 A1 | 12/2002 | Chen et al. |
| 2003/0022216 A1 | 1/2003 | Mao et al. |
| 2003/0071525 A1 | 4/2003 | Tong et al. |
| 2003/0087338 A1 | 5/2003 | Messersmith et al. |

(56) References Cited

U.S. PATENT DOCUMENTS

| | | |
|---|---|---|
| 2003/0096226 A1 | 5/2003 | Logtenberg |
| 2003/0129676 A1 | 7/2003 | Terstappen et al. |
| 2003/0138645 A1 | 7/2003 | Gleason et al. |
| 2003/0157054 A1 | 8/2003 | Gillies et al. |
| 2003/0159999 A1 | 8/2003 | Oakey et al. |
| 2003/0163084 A1 | 8/2003 | Griffiths et al. |
| 2003/0206901 A1 | 11/2003 | Chen |
| 2003/0213551 A1 | 11/2003 | Derand et al. |
| 2003/0216534 A1 | 11/2003 | Chaikof et al. |
| 2004/0004043 A1 | 1/2004 | Terstappen et al. |
| 2004/0009471 A1 | 1/2004 | Cao |
| 2004/0028875 A1 | 2/2004 | Van et al. |
| 2004/0038339 A1 | 2/2004 | Kufer et al. |
| 2004/0053334 A1 | 3/2004 | Ratner et al. |
| 2004/0072269 A1 | 4/2004 | Rao et al. |
| 2004/0109853 A1 | 6/2004 | McDaniel |
| 2004/0115721 A1 | 6/2004 | Mao et al. |
| 2004/0118757 A1 | 6/2004 | Terstappen et al. |
| 2004/0175407 A1 | 9/2004 | McDaniel |
| 2004/0225249 A1 | 11/2004 | Leonard et al. |
| 2004/0254419 A1 | 12/2004 | Wang et al. |
| 2005/0025797 A1 | 2/2005 | Wang et al. |
| 2005/0042766 A1 | 2/2005 | Ohman et al. |
| 2005/0058576 A1 | 3/2005 | Pranis et al. |
| 2005/0079132 A1 | 4/2005 | Wang et al. |
| 2005/0100675 A1 | 5/2005 | Mao et al. |
| 2005/0107870 A1 | 5/2005 | Wang et al. |
| 2005/0147758 A1 | 7/2005 | Mao et al. |
| 2005/0153342 A1 | 7/2005 | Chen |
| 2005/0175501 A1 | 8/2005 | Thompson et al. |
| 2005/0178286 A1 | 8/2005 | Bohn et al. |
| 2005/0181195 A1 | 8/2005 | Dubrow |
| 2005/0181463 A1 | 8/2005 | Rao et al. |
| 2005/0186685 A1 | 8/2005 | Kange et al. |
| 2005/0215764 A1 | 9/2005 | Tuszynski et al. |
| 2005/0230272 A1 | 10/2005 | Lee et al. |
| 2005/0255327 A1 | 11/2005 | Chaney et al. |
| 2005/0265980 A1 | 12/2005 | Chen et al. |
| 2005/0267440 A1 | 12/2005 | Herman et al. |
| 2005/0288398 A1 | 12/2005 | Messersmith et al. |
| 2006/0002825 A1 | 1/2006 | Derand et al. |
| 2006/0009550 A1 | 1/2006 | Messersmith et al. |
| 2006/0014013 A1 | 1/2006 | Saavedra et al. |
| 2006/0057180 A1 | 3/2006 | Chilkoti et al. |
| 2006/0076295 A1 | 4/2006 | Leonard et al. |
| 2006/0079740 A1 | 4/2006 | Silver et al. |
| 2006/0088666 A1 | 4/2006 | Kobrin et al. |
| 2006/0093836 A1 | 5/2006 | Huang et al. |
| 2006/0134599 A1 | 6/2006 | Toner et al. |
| 2006/0137438 A1 | 6/2006 | Lenzing et al. |
| 2006/0159916 A1 | 7/2006 | Dubrow et al. |
| 2006/0160066 A1 | 7/2006 | Bhatia et al. |
| 2006/0166183 A1 | 7/2006 | Short et al. |
| 2006/0169642 A1 | 8/2006 | Oakey et al. |
| 2006/0173394 A1 | 8/2006 | Stroock et al. |
| 2006/0194192 A1 | 8/2006 | Rao et al. |
| 2006/0237390 A1 | 10/2006 | King et al. |
| 2006/0251795 A1 | 11/2006 | Kobrin et al. |
| 2006/0252046 A1 | 11/2006 | Short et al. |
| 2006/0252054 A1 | 11/2006 | Lin et al. |
| 2006/0254972 A1 | 11/2006 | Tai et al. |
| 2006/0285996 A1 | 12/2006 | Ohman et al. |
| 2007/0003549 A1 | 1/2007 | Ignatovich et al. |
| 2007/0010702 A1 | 1/2007 | Wang et al. |
| 2007/0025883 A1 | 2/2007 | Tai et al. |
| 2007/0026381 A1 | 2/2007 | Huang et al. |
| 2007/0026416 A1 | 2/2007 | Fuchs |
| 2007/0026469 A1 | 2/2007 | Fuchs et al. |
| 2007/0032620 A1 | 2/2007 | Gleason et al. |
| 2007/0037173 A1 | 2/2007 | Allard et al. |
| 2007/0048859 A1 | 3/2007 | Sears |
| 2007/0059716 A1 | 3/2007 | Balis et al. |
| 2007/0071762 A1 | 3/2007 | Ts'o et al. |
| 2007/0072220 A1 | 3/2007 | Chilkoti |
| 2007/0077276 A1 | 4/2007 | Haynie |
| 2007/0122406 A1 | 5/2007 | Chamberlain et al. |
| 2007/0131622 A1 | 6/2007 | Oakey et al. |
| 2007/0154960 A1 | 7/2007 | Connelly et al. |
| 2007/0172903 A1 | 7/2007 | Toner et al. |
| 2007/0178133 A1 | 8/2007 | Rolland |
| 2007/0187250 A1 | 8/2007 | Huang et al. |
| 2007/0202536 A1 | 8/2007 | Yamanishi et al. |
| 2007/0231851 A1 | 10/2007 | Toner et al. |
| 2007/0259424 A1 | 11/2007 | Toner et al. |
| 2007/0264675 A1 | 11/2007 | Toner et al. |
| 2007/0266777 A1 | 11/2007 | Bergman et al. |
| 2007/0281353 A1 | 12/2007 | Vacanti et al. |
| 2008/0009780 A1 | 1/2008 | Leonard et al. |
| 2008/0023399 A1 | 1/2008 | Inglis et al. |
| 2008/0026486 A1 | 1/2008 | Cooper et al. |
| 2008/0090239 A1 | 4/2008 | Shoemaker et al. |
| 2008/0113350 A1 | 5/2008 | Terstappen |
| 2008/0114096 A1 | 5/2008 | Qu et al. |
| 2008/0131425 A1 | 6/2008 | Garcia et al. |
| 2008/0147178 A1 | 6/2008 | Pacetti et al. |
| 2008/0149566 A1 | 6/2008 | Messersmith et al. |
| 2008/0176271 A1 | 7/2008 | Silver et al. |
| 2008/0181861 A1 | 7/2008 | Jiang et al. |
| 2008/0188638 A1 | 8/2008 | Breitenkamp et al. |
| 2008/0206757 A1 | 8/2008 | Lin et al. |
| 2008/0207913 A1 | 8/2008 | Breitenkamp et al. |
| 2008/0213853 A1 | 9/2008 | Garcia et al. |
| 2008/0220531 A1 | 9/2008 | Stayton et al. |
| 2008/0241892 A1 | 10/2008 | Roitman et al. |
| 2008/0248499 A1 | 10/2008 | Chiu et al. |
| 2008/0255305 A1 | 10/2008 | Brook et al. |
| 2008/0274335 A1 | 11/2008 | Bowman et al. |
| 2008/0311182 A1 | 12/2008 | Ferrari et al. |
| 2008/0312356 A1 | 12/2008 | Kobrin et al. |
| 2009/0020431 A1 | 1/2009 | Voccia et al. |
| 2009/0029043 A1 | 1/2009 | Rong et al. |
| 2009/0036982 A1 | 2/2009 | Aharoni et al. |
| 2009/0060791 A1 | 3/2009 | Hagiwara et al. |
| 2009/0068760 A1 | 3/2009 | Nelson et al. |
| 2009/0093610 A1 | 4/2009 | Textor et al. |
| 2009/0098017 A1 | 4/2009 | Celik-Butler et al. |
| 2009/0105463 A1 | 4/2009 | Berry et al. |
| 2009/0114344 A1 | 5/2009 | Barinov et al. |
| 2009/0117574 A1 | 5/2009 | Labgold et al. |
| 2009/0136982 A1 | 5/2009 | Tang et al. |
| 2009/0139931 A1 | 6/2009 | Leonard et al. |
| 2009/0142772 A1 | 6/2009 | Lau et al. |
| 2009/0156460 A1 | 6/2009 | Jiang et al. |
| 2009/0181441 A1 | 7/2009 | Jin et al. |
| 2009/0203536 A1 | 8/2009 | Vermette et al. |
| 2009/0215088 A1 | 8/2009 | Forsyth et al. |
| 2009/0226499 A1 | 9/2009 | Wisniewski et al. |
| 2009/0247424 A1 | 10/2009 | Chilkoti et al. |
| 2009/0259015 A1 | 10/2009 | Jiang et al. |
| 2009/0259302 A1 | 10/2009 | Trollsas et al. |
| 2009/0263457 A1 | 10/2009 | Trollsas et al. |
| 2009/0264317 A1 | 10/2009 | Ofir et al. |
| 2009/0269323 A1 | 10/2009 | Luk et al. |
| 2009/0281250 A1 | 11/2009 | Desimone et al. |
| 2009/0285873 A1 | 11/2009 | Lim et al. |
| 2009/0292234 A1 | 11/2009 | Leonard et al. |
| 2009/0298067 A1 | 12/2009 | Irimia et al. |
| 2009/0311734 A1 | 12/2009 | Greve et al. |
| 2009/0317836 A1 | 12/2009 | Kuhn et al. |
| 2010/0004578 A1 | 1/2010 | Leonard et al. |
| 2010/0028526 A1 | 2/2010 | Martin et al. |
| 2010/0055733 A1 | 3/2010 | Lutolf et al. |
| 2010/0059414 A1 | 3/2010 | Sturm et al. |
| 2010/0061892 A1 | 3/2010 | Flaim et al. |
| 2010/0062156 A1 | 3/2010 | Kurth et al. |
| 2010/0063570 A1 | 3/2010 | Pacetti et al. |
| 2010/0081735 A1 | 4/2010 | Mao et al. |
| 2010/0092393 A1 | 4/2010 | Haghgooie et al. |
| 2010/0092491 A1 | 4/2010 | Anastasi et al. |
| 2010/0096327 A1 | 4/2010 | Gin et al. |
| 2010/0099160 A1 | 4/2010 | Jiang et al. |
| 2010/0099579 A1 | 4/2010 | Chilkoti |
| 2010/0112026 A1 | 5/2010 | Karp et al. |
| 2010/0118642 A1 | 5/2010 | Ho et al. |

(56) References Cited

U.S. PATENT DOCUMENTS

| | | |
|---|---|---|
| 2010/0137984 A1 | 6/2010 | Lowery et al. |
| 2010/0140160 A1 | 6/2010 | Dubrow et al. |
| 2010/0143438 A1 | 6/2010 | Todd et al. |
| 2010/0143741 A1 | 6/2010 | Bell et al. |
| 2010/0145286 A1 | 6/2010 | Zhang et al. |
| 2010/0151491 A1 | 6/2010 | Himmelhaus et al. |
| 2010/0152708 A1 | 6/2010 | Li et al. |
| 2010/0159462 A1 | 6/2010 | Takayama et al. |
| 2010/0160645 A1 | 6/2010 | Breitenkamp et al. |
| 2010/0169990 A1 | 7/2010 | Clarke et al. |
| 2010/0173402 A1 | 7/2010 | Chen |
| 2010/0198131 A1 | 8/2010 | Leonard et al. |
| 2010/0209612 A1 | 8/2010 | Rong et al. |
| 2010/0210745 A1 | 8/2010 | Mcdaniel et al. |
| 2010/0226943 A1 | 9/2010 | Brennan et al. |
| 2010/0233146 A1 | 9/2010 | Mcdaniel |
| 2010/0233693 A1 | 9/2010 | Kopf-Sill et al. |
| 2010/0233694 A1 | 9/2010 | Kopf-Sill |
| 2010/0233812 A1 | 9/2010 | Sun et al. |
| 2010/0247492 A1 | 9/2010 | Kuhn et al. |
| 2010/0247760 A1 | 9/2010 | Houben et al. |
| 2010/0248334 A1 | 9/2010 | Mcdaniel |
| 2010/0248358 A1 | 9/2010 | Yoshioka |
| 2010/0273991 A1 | 10/2010 | Luk et al. |
| 2010/0278892 A1 | 11/2010 | Krauland et al. |
| 2010/0279321 A1 | 11/2010 | Chiu et al. |
| 2010/0280252 A1 | 11/2010 | Breitenkamp et al. |
| 2010/0285581 A1 | 11/2010 | Hauch et al. |
| 2010/0285972 A1 | 11/2010 | Dubrow et al. |
| 2010/0294146 A1 | 11/2010 | Fragala et al. |
| 2010/0304485 A1 | 12/2010 | Karnik et al. |
| 2010/0311599 A1 | 12/2010 | Wheeler et al. |
| 2010/0316842 A1 | 12/2010 | Tuteja et al. |
| 2010/0323918 A1 | 12/2010 | Huang et al. |
| 2010/0330025 A1 | 12/2010 | Messersmith et al. |
| 2010/0331965 A1 | 12/2010 | Dugas et al. |
| 2011/0005997 A1 | 1/2011 | Kurth et al. |
| 2011/0008404 A1 | 1/2011 | Lyon et al. |
| 2011/0027803 A1 | 2/2011 | Moussavi et al. |
| 2011/0048947 A1 | 3/2011 | Petronis et al. |
| 2011/0054347 A1 | 3/2011 | Goss et al. |
| 2011/0056884 A1 | 3/2011 | Leonard et al. |
| 2011/0059468 A1 | 3/2011 | Earhart et al. |
| 2011/0062083 A1 | 3/2011 | Leonard et al. |
| 2011/0066097 A1 | 3/2011 | Leonard et al. |
| 2011/0091864 A1 | 4/2011 | Karlsson et al. |
| 2011/0097277 A1 | 4/2011 | Jiang et al. |
| 2011/0105712 A1 | 5/2011 | Jiang et al. |
| 2011/0105982 A1 | 5/2011 | Leonard et al. |
| 2011/0117674 A1 | 5/2011 | Melin et al. |
| 2011/0143119 A1 | 6/2011 | Bell et al. |
| 2011/0165161 A1 | 7/2011 | Lin et al. |
| 2011/0165415 A1 | 7/2011 | Ma et al. |
| 2011/0171663 A1 | 7/2011 | Smith et al. |
| 2011/0192233 A1 | 8/2011 | Aizenberg et al. |
| 2011/0195104 A1 | 8/2011 | Jiang et al. |
| 2011/0212085 A1 | 9/2011 | Joseloff et al. |
| 2011/0212297 A1 | 9/2011 | Dhinojwala et al. |
| 2011/0212440 A1 | 9/2011 | Viovy et al. |
| 2011/0217449 A1 | 9/2011 | Lowery et al. |
| 2011/0224383 A1 | 9/2011 | Sill et al. |
| 2011/0236904 A1 | 9/2011 | Hauch et al. |
| 2011/0240064 A1 | 10/2011 | Wales et al. |
| 2011/0240595 A1 | 10/2011 | Dubrow |
| 2011/0250626 A1 | 10/2011 | Williams et al. |
| 2011/0250679 A1 | 10/2011 | Chang |
| 2011/0256619 A1 | 10/2011 | Vacanti et al. |
| 2011/0266492 A1 | 11/2011 | Stayton et al. |
| 2011/0275530 A1 | 11/2011 | Walfish et al. |
| 2011/0282005 A1 | 11/2011 | Jiang et al. |
| 2011/0294186 A1 | 12/2011 | Fuchs et al. |
| 2011/0300551 A1 | 12/2011 | Rao et al. |
| 2011/0300603 A1 | 12/2011 | Forsyth et al. |
| 2011/0301442 A1 | 12/2011 | Luecke et al. |
| 2011/0305660 A1 | 12/2011 | Stayton et al. |
| 2011/0305872 A1 | 12/2011 | Li et al. |
| 2011/0305881 A1 | 12/2011 | Schultz et al. |
| 2011/0305895 A1 | 12/2011 | Roth et al. |
| 2011/0305898 A1 | 12/2011 | Zhang et al. |
| 2011/0305909 A1 | 12/2011 | Weaver et al. |
| 2012/0003711 A1 | 1/2012 | Tseng et al. |
| 2012/0006728 A1 | 1/2012 | Huang et al. |
| 2012/0015146 A1 | 1/2012 | Advincula et al. |
| 2012/0015835 A1 | 1/2012 | Fuchs et al. |
| 2012/0021200 A1 | 1/2012 | Koberstein et al. |
| 2012/0028342 A1 | 2/2012 | Ismagilov et al. |
| 2012/0037544 A1 | 2/2012 | Lane et al. |
| 2012/0045828 A1 | 2/2012 | Davis et al. |
| 2012/0052415 A1 | 3/2012 | Fragala et al. |
| 2012/0058302 A1 | 3/2012 | Eggenspieler et al. |
| 2012/0058500 A1 | 3/2012 | Mitchell et al. |
| 2012/0061304 A1 | 3/2012 | Leonard et al. |
| 2012/0064150 A1 | 3/2012 | Wisniewski et al. |
| 2012/0077246 A1 | 3/2012 | Hong et al. |
| 2012/0094327 A1 | 4/2012 | Young et al. |
| 2012/0114742 A1 | 5/2012 | Martinez et al. |
| 2012/0178094 A1 | 7/2012 | Kuhn |
| 2012/0196273 A1 | 8/2012 | Huang et al. |
| 2012/0252022 A1 | 10/2012 | Walfish et al. |
| 2012/0270209 A1 | 10/2012 | Shah et al. |
| 2012/0301900 A1 | 11/2012 | Kang et al. |
| 2013/0121895 A1 | 5/2013 | Tang et al. |
| 2013/0143197 A1 | 6/2013 | Heyneker |
| 2014/0017776 A1 | 1/2014 | Kopf-Sill |
| 2014/0296095 A1 | 10/2014 | Lin et al. |
| 2016/0059234 A1 | 3/2016 | Chang et al. |
| 2017/0199184 A1 | 7/2017 | Chang et al. |
| 2017/0268967 A1 | 9/2017 | Shao |

FOREIGN PATENT DOCUMENTS

| | | |
|---|---|---|
| CN | 101701039 A | 5/2010 |
| CN | 101765762 A | 6/2010 |
| CN | 102011193 A | 4/2011 |
| CN | 103261436 A | 8/2013 |
| CN | 103998932 A | 8/2014 |
| EP | 0783694 B1 | 11/2003 |
| EP | 2359689 A1 | 8/2011 |
| EP | 1569510 B1 | 11/2011 |
| EP | 2359689 B1 | 8/2015 |
| GB | 2427468 B | 3/2011 |
| GB | 2472927 B | 5/2011 |
| WO | WO-9823948 A1 | 6/1998 |
| WO | WO-9920649 A1 | 4/1999 |
| WO | WO-2007048459 A1 | 5/2007 |
| WO | WO-2007079229 A2 | 7/2007 |
| WO | WO-2007079250 A2 | 7/2007 |
| WO | WO-2008157257 A1 | 12/2008 |
| WO | WO-2007079250 A3 | 3/2009 |
| WO | WO-2009051734 A1 | 4/2009 |
| WO | WO-2009088933 A1 | 7/2009 |
| WO | WO-2009140326 A2 | 11/2009 |
| WO | WO-2010123608 A2 | 10/2010 |
| WO | WO-2010124227 A2 | 10/2010 |
| WO | WO-2010132795 A2 | 11/2010 |
| WO | WO-2012016136 A2 | 2/2012 |
| WO | WO-2012094642 A2 | 7/2012 |
| WO | WO-2012103025 A2 | 8/2012 |
| WO | WO-2012116073 A2 | 8/2012 |
| WO | WO-2013003624 A2 | 1/2013 |
| WO | WO-2013006828 A1 | 1/2013 |
| WO | WO-2013036620 A1 | 3/2013 |
| WO | WO-2013131001 A2 | 9/2013 |
| WO | WO-2015153816 | 10/2015 |

OTHER PUBLICATIONS

Barradas, et al. Towards the biological understanding of CTC: capture technologies, definitions and potential to create metastasis. Cancers 5.4 (2013): 1619-1642.

Hong, et al. Detecting circulating tumor cells: current challenges and new trends. Theranostics 3.6 (2013): 377-394.

(56) References Cited

OTHER PUBLICATIONS

Park, et al. Continuous focusing of microparticles using inertial lift force and vorticity via multi-orifice microfluidic channels. Lab on a Chip 9.7 (2009): 939-948.
Lawrence, et al. Leukocytes roll on a selectin at physiologic flow rates: distinction from and prerequisite for adhesion through integrins. Cell. May 31, 1991;65(5):859-73.
Notice of allowance dated Jul. 7, 2016 for U.S. Appl. No. 14/065,265.
Notice of allowance dated Sep. 1, 2016 for U.S. Appl. No. 14/128,354.
Ananthanarayanan, et al. Neural stem cell adhesion and proliferation on phospholipid bilayers functionalized with RGD peptides. Biomaterials, Elsevier Science Publishers BV., Barking GB, vol. 31, No. 33, Nov. 1, 2010, pp. 8706-8715.
"European search report dated Jan. 29, 2016 for EP 15182577.5".
Kaladhar, et al. Cell mimetic lateral stabilization of outer cell mimetic bilayer on polymer surfaces by peptide bonding and their blood compatibility. J Biomed Mater Res A. Oct. 2006;79(1):23-35.
Lin, et al. Adhesion of antibody-functionalized polymersomes. Langmuir. Apr. 25, 2006;22(9):3975-9.
Lin, J.J. et al. 2006. Adhesion of antibody-functionalized polymersomes. Langmuir 22: 3975-3979. specif. pp. 3975, 3979.
"Office action dated Jan. 21, 2015 for U.S. Appl. No. 14/065,265."
Office action dated Mar. 9, 2016 for U.S. Appl. No. 14/065,265.
Office action dated Mar. 23, 2016 for U.S. Appl. No. 14/128,354.
"Office action dated May 29, 2015 for U.S. Appl. No. 14/065,265."
"Office action dated Mar. 23, 2016 for U.S. Appl. No. 14/128,345".
Phillips, J.A. et al. 2009. Enrichment of cancer cells using aptamers immobilized on a microfluidic channel. Analytical Chemistry81 : 1 033-1 039. specif. pp. 1 034, 1 035, 1 036, 1 037, 1 038.
Xu, et al. Aptamer-based microfluidic device for enrichment, sorting, and detection of multiple cancer cells. Anal Chem. Sep. 1, 2009;81(17):7436-42. doi: 10.1021/ac9012072.
Xu, Y. et al. 2009. Aptamer-based microfluidic device for enrichment, sorting, and detection of multiple cancer cells. AnalyticalChemistry 81: 7436-7442. specif. pp. 7436, 7437, 7439, 7440.
Alix-Panabieres, et al. Challenges in circulating tumour cell research. Nat Rev Cancer. Sep. 2014;14(9):623-31. doi: 10.1038/nrc3820. Epub Jul. 31, 2014.
Antolovic, et al. Heterogeneous detection of circulating tumor cells in patients with colorectal cancer by immunomagnetic enrichment using different EpCAM-specific antibodies. BMC Biotechnol. Apr. 28, 2010;10:35. doi: 10.1186/1472-6750-10-35.
Baeuerle, et al. EpCAM (CD326) finding its role in cancer. Br J Cancer. Feb. 12, 2007;96(3):417-23. Epub Jan. 9, 2007.
Balzar, et al. Epidermal growth factor-like repeats mediate lateral and reciprocal interactions of Ep-CAM molecules in homophilic adhesions. Mol Cell Biol. Apr. 2001;21(7):2570-80.
Barkley, et al. Bubble-induced detachment of affinity-adsorbed erythrocytes. Biotechnol Appl Biochem. Oct. 2004;40(Pt 2):145-9.
Bhagat, et al. Continuous particle separation in spiral microchannels using Dean flows and differential migration. Lab Chip. Nov. 2008;8(11):1906-14. doi: 10.1039/b807107a. Epub Sep. 24, 2008.
Cao, et al. Detachment strategies for affinity-adsorbed cells. Enzyme and microbial technology. 2002; 31: 153-160.
Chaudry, et al. EpCAM an immunotherapeutic target for gastrointestinal malignancy: current experience and future challenges. Br J Cancer. Apr. 10, 2007;96(7):1013-9. Epub Feb. 27, 20073
Chen, et al. Generation and characterization of monoclonal antibodies against dengue virus type 1 for epitope mapping and serological detection by epitope-based peptide antigens. Clin Vaccine Immunol. Apr. 2007;14(4):404-11. Epub Feb. 7, 2007.
Cima, et al. Label-free isolation of circulating tumor cells in microfluidic devices: Current research and perspectives. Biomicrofluidics. Jan. 24, 2013;7(1):11810. doi: 10.1063/1.4780062. eCollection 2013.
Co-pending U.S. Appl. No. 14/781,165, filed Sep. 29, 2015.
Co-pending U.S. Appl. No. 15/072,287, filed Mar. 16, 2016.
Co-pending U.S. Appl. No. 15/378,938, filed Dec. 14, 2016.
Cornell, et al. A biosensor that uses ion-channel switches. Letters to Nauture. Jun. 5, 1997. vol. 387. p. 580-583.

Dickson, et al. Efficient capture of circulating tumor cells with a novel immunocytochemical microfluidic device. Biomicrofluidics. Sep. 2011;5(3):34119-3411915. doi: 10.1063/1.3623748. Epub Aug. 22, 2011.
European search report and written opinion dated May 2, 2015 for EP Application No. 12805303.0.
Garstecki, et al. Formation of droplets and bubbles in a microfluidic T-junction-scaling and mechanism of break-up. Lab Chip. Mar. 2006;6(3):437-46. Epub Jan. 25, 2006.
Gervais, Luc. Capillary Microfluidic Chips for Point-of-Care Testing: from Research Tools to Decentralized Medical Diagnostics. InfoScience. 2011. Thesis 5047. Available at http://infoscience.epfl. ch/record/165376/files/EPFL_TH5047.pdf.
Gomez-Suarez, et al. Analysis of bacterial detachment from substratum surfaces by the passage of air-liquid interfaces. Appl Environ Microbiol. Jun. 2001;67(6):2531-7.
Holmen, et al. Heterogeneity of human nasal vascular and sinusoidal endothelial cells from the inferior turbinate. Am J Respir Cell Mol Biol. Jan. 2005;32(1):18-27. Epub Oct. 21, 2004.
"Hsiung, et al. A planar interdigitated ring electrode array via dielectrophoresis for uniform patterning of cells. Biosens Bioelectron. Dec. 1, 2008;24(4):869-875."
Hsu, et al. Microvortex for focusing, guiding and sorting of particles. Lab Chip. Dec. 2008;8(12):2128-34. doi: 10.1039/b813434k. Epub Oct. 30, 2008.
International search report and written opinion dated May 30, 2013 for PCT Application No. PCT/US2013/028667 with publication.
International search report and written opinion dated Dec. 10, 2012 for PCT/US2012/044701.
Ishihara, et al. Photoinduced graft polymerization of 2-methacryloyloxyethyl phosphorylcholine on polyethylene membrane surface for obtaining blood cell adhesion resistance. Colloids and Surfaces B: Biointerfaces, vol. 18, No. 3-4, Oct. 1, 2000, pp. 325-355.
Johnson, et al. Structure of an adsorbed dimyristoylphosphatidylcholine bilayer measured with specular reflection of neutrons. Biophys J. Feb. 1991;59(2):289-94.
Kahn, et al. Enumeration of circulating tumor cells in the blood of breast cancer patients after filtration enrichment: correlation with disease stage. Breast Cancer Res Treat. Aug. 2004;86(3):237-47.
Kaladhar, et al. Supported cell mimetic monolayers and their interaction with blood. Langmuir. Dec. 7, 2004;20(25):11115-22.
Karabacak, et al. Microfluidic, marker-free isolation of circulating tumor cells from blood samples. Nat Protoc. Mar. 2014;9(3):694-710. doi: 10.1038/nprot.2014.044. Epub Feb. 27, 2014.
Nagrath, et al. Isolation of rare circulating tumour cells in cancer patients by microchip technology. Nature. Dec. 20, 2007;450(7173):1235-9.
NCBI Direct Submission. NM_002354.2. *Homo sapiens* epithelial cell adhesion molecule (EPCAM), mRNA. Feb. 5, 2012. [Retrieved from the Internet:<http://www.ncbi.nlm.nih.gov/nuccore/218505669?sat=15&satkey=5763417>.
Pantel, et al. Detection, clinical relevance and specific biological properties of disseminating tumour cells. Nat Rev Cancer. May 2008;8(5):329-40. doi: 10.1038/nrc2375.
Patriarca, et al. Epithelial cell adhesion molecule expression (CD326) in cancer: a short review. Cancer Treat Rev. Feb. 2012;38(1):68-75. doi: 10.1016/j.ctrv.2011.04.002. Epub May 14, 2011.
Ruf, et al. Characterisation of the new EpCAM-specific antibody HO-3: implications for trifunctional antibody immunotherapy of cancer. Br J Cancer. Aug. 6, 2007;97(3):315-21. Epub Jul. 10, 2007.
Tan, et al. Versatile label free biochip for the detection of circulating tumor cells from peripheral blood in cancer patients. Biosens Bioelectron. Dec. 15, 2010;26(4):1701-5. doi: 10.1016/j.bios.2010. 07.054. Epub Jul. 22, 2010.
Adams, et al. Highly efficient circulating tumor cell isolation from whole blood and label-free enumeration using polymer-based microfluidics with an integrated conductivity sensor. J Am Chem Soc. Jul. 9, 2008;130(27):8633-41. doi: 10.1021/ja8015022. Epub Jun. 17, 2008.
Adams, et al. Integrated acoustic and magnetic separation in microfluidic channels. Appl Phys Lett. Dec. 21, 2009;95(25):254103.

(56) References Cited

OTHER PUBLICATIONS

Allard, et al. Tumor cells circulate in the peripheral blood of all major carcinomas but not in healthy subjects or patients with nonmalignant diseases. Clin Cancer Res. Oct. 15, 2004;10(20):6897-904.
Balasubramanian, et al. Confocal images of circulating tumor cells obtained using a methodology and technology that removes normal cells. Mol Pharm. Sep.-Oct. 2009;6(5):1402-8. doi: 10.1021/mp9000519.
Cavalli, et al. Micro- and nanobubbles: a versatile non-viral platform for gene delivery. Int J Pharm. Nov. 18, 2013;456(2):437-45. doi: 10.1016/j.ijpharm.2013.08.041. Epub Sep. 2, 2013.
Cohen, et al. Relationship of circulating tumor cells to tumor response, progression-free survival, and overall survival in patients with metastatic colorectal cancer. J Clin Oncol. Jul. 1, 2008;26(19):3213-21. doi: 10.1200/JCO.2007.15.8923.
Cremer, et al. Writing and erasing barriers to lateral mobility into fluid phospholipid bilayers. Langmuir 15.11 (1999): 3893-3896.
Dainiak, et al. Cell chromatography: separation of different microbial cells using IMAC supermacroporous monolithic columns. Biotechnol Prog. Mar.-Apr. 2005;21(2):644-9.
De Giorgi, et al. Application of a filtration- and isolation-by-size technique for the detection of circulating tumor cells in cutaneous melanoma. J Invest Dermatol. Oct. 2010;130(10):2440-7. doi: 10.1038/jid.2010.141. Epub Jun. 10, 2010.
Dharmasiri, et al. High-throughput selection, enumeration, electrokinetic manipulation, and molecular profiling of low-abundance circulating tumor cells using a microfluidic system. Anal Chem. Mar. 15, 2011;83(6):2301-9. doi: 10.1021/ac103172y. Epub Feb. 14, 2011.
Fehm, et al. Cytogenetic evidence that circulating epithelial cells in patients with carcinoma are malignant. Clin Cancer Res. Jul. 2002;8(7):2073-84.
Fehm, et al. HER2 status of circulating tumor cells in patients with metastatic breast cancer: a prospective, multicenter trial. Breast Cancer Res Treat. Nov. 2010;124(2):403-12. doi: 10.1007/s10549-010-1163-x. Epub Sep. 22, 2010.
Geers, et al. Targeted liposome-loaded microbubbles for cell-specific ultrasound-triggered drug delivery. Small. Dec. 9, 2013;9(23):4027-35. doi: 10.1002/smll.201300161. Epub Jun. 5, 2013.
Glasmastar, et al. Protein adsorption on supported phospholipid bilayers. J Colloid Interface Sci. Feb. 1, 2002;246(1):40-7.
Huang, et al. Type I Collagen-Functionalized Supported Lipid Bilayer as a Cell Culture Platform. Biomacromolecules, vol. 11, No. 5, May 10, 2010, pp. 1231-1240.
Kaizuka, et al. Structure and dynamics of supported intermembrane junctions. Biophys J. Feb. 2004;86(2):905-12.
Kang, et al. A combined micromagnetic-microfluidic device for rapid capture and culture of rare circulating tumor cells. Lab Chip. Jun. 21, 2012;12(12):2175-81. doi: 10.1039/c2lc40072c. Epub Mar. 28, 2012.
Kang, et al. Isomagnetophoresis to discriminate subtle difference in magnetic susceptibility. Journal of the American Chemical Society 130.2 (2008): 396-397.
Krivacic, et al. A rare-cell detector for cancer. Proc Natl Acad Sci U S A. Jul. 20, 2004;101(29):10501-4. Epub Jul. 12, 2004.
Kuo, et al. Deformability considerations in filtration of biological cells. Lab Chip. Apr. 7, 2010;10(7):837-42. doi: 10.1039/b922301k. Epub Jan. 19, 2010.
Li, et al. Negative enrichment of target cells by microfluidic affinity chromatography. Anal Chem. Oct. 15, 2011;83(20):7863-9. doi: 10.1021/ac201752s. Epub Sep. 22, 2011.
Mahalingam, et al. Formation, stability, and mechanical properties of bovine serum albumin stabilized air bubbles produced using coaxial electrohydrodynamic atomization. Langmuir. Jun. 17, 2014;30(23):6694-703. doi: 10.1021/la5011715. Epub Jun. 4, 2014.
Olmos, et al. Circulating tumour cell (CTC) counts as intermediate end points in castration-resistant prostate cancer (CRPC): a single-centre experience. Ann Oncol. Jan. 2009;20(1):27-33. doi: 10.1093/annonc/mdn544. Epub Aug. 11, 2008.
Ozkumur, et al. Inertial focusing for tumor antigen-dependent and -independent sorting of rare circulating tumor cells. Sci Transl Med. Apr. 3, 2013;5(179):179ra47. doi: 10.1126/scitranslmed. 3005616.
Panchision, et al. Optimized flow cytometric analysis of central nervous system tissue reveals novel functional relationships among cells expressing CD133, CD15, and CD24. Stem Cells. Jun. 2007;25(6):1560-70. Epub Mar. 1, 2007.
Phillips, et al. Enrichment of cancer cells using aptamers immobilized on a microfluidic channel. Anal Chem. Feb. 1, 2009;81(3):1033-9. doi: 10.1021/ac802092j.
Schiro, et al. Sensitive and high-throughput isolation of rare cells from peripheral blood with ensemble-decision aliquot ranking. Angew Chem Int Ed Engl. May 7, 2012;51(19):4618-22. doi: 10.1002/anie.201108695. Epub Feb. 22, 2012.
Shah, et al. Biopolymer system for cell recovery from microfluidic cell capture devices. Anal Chem. Apr. 17, 2012;84(8):3682-8. doi: 10.1021/ac300190j. Epub Apr. 3, 2012.
Shih, et al. Flow-focusing regimes for accelerated production of monodisperse drug-loadable microbubbles toward clinical-scale applications. Lab Chip. Dec. 21, 2013;13(24):4816-26. doi: 10.1039/c3lc51016f.
Singer, et al. The fluid mosaic model of the structure of cell membranes. Science. Feb. 18, 1972;175(4023):720-31.
Stott, et al. Isolation of circulating tumor cells using a microvortex-generating herringbone-chip. Proc Natl Acad Sci U S A. Oct. 26, 2010;107(43):18392-7. doi: 10.1073/pnas.1012539107. Epub Oct. 7, 2010.
Stroock, et al. Chaotic mixer for microchannels. Science. Jan. 25, 2002;295(5555):647-51.
Sun, et al. High-performance size-based microdevice for the detection of circulating tumor cells from peripheral blood in rectal cancer patients. PLoS One. Sep. 16, 2013;8(9):e75865. doi: 10.1371/journal.pone.0075865. eCollection 2013.
Thorsteinsson, et al. The clinical significance of circulating tumor cells in non-metastatic colorectal cancer-a review. European Journal of Surgical Oncology (EJSO) 37.6 (2011): 459-465.
Triffo, et al. Monitoring lipid anchor organization in cell membranes by PIE-FCCS. J Am Chem Soc. Jul. 4, 2012;134(26):10833-42. doi: 10.1021/ja300374c. Epub Jun. 14, 2012.
Tseng, et al. Tethered fibronectin liposomes on supported lipid bilayers as a prepackaged controlled-release platform for cell-based assays. Biomacromolecules. Aug. 13, 2012;13(8):2254-62. doi: 10.1021/bm300426u. Epub Jul. 11, 2012.
U.S. Appl. No. 13/007477, filed Jan. 14, 2011.
Vona, et al. Isolation by size of epithelial tumor cells : a new method for the immunomorphological and molecular characterization of circulating tumor cells. Am J Pathol. Jan. 2000;156(1):57-63.
Wang, et al. Highly efficient capture of circulating tumor cells by using nanostructured silicon substrates with integrated chaotic micromixers. Angew Chem Int Ed Engl. Mar. 21, 2011;50(13):3084-8. doi: 10.1002/anie.201005853. Epub Mar. 4, 2011.
Wang, et al. Open-tubular capillary cell affinity chromatography: single and tandem blood cell separation. Anal Chem. Mar. 15, 2008;80(6):2118-24. doi: 10.1021/ac702553w. Epub Feb. 21, 2008.
Wang, et al. Shear stress induces endothelial differentiation from a murine embryonic mesenchymal progenitor cell line. Arterioscler Thromb Vasc Biol. Sep. 2005;25(9):1817-23. Epub Jun. 30, 2005.
Wu, et al. Antibody conjugated supported lipid bilayer for capturing and purification of viable tumor cells in blood for subsequent cell culture. Biomaterials. Jul. 2013;34(21):5191-9. doi: 10.1016/j.biomaterials.2013.03.096. Epub Apr. 21, 2013.
Xu, et al. A cancer detection platform which measures telomerase activity from live circulating tumor cells captured on a microfilter. Cancer Res. Aug. 15, 2010;70(16):6420-6. doi: 10.1158/0008-5472. CAN-10-0686. Epub Jul. 27, 2010.
Yurke, et al. A DNA-fuelled molecular machine made of DNA. Nature. Aug. 10, 2000;406(6796):605-8.
Extended European Search Report and Search Opinion dated Feb. 28, 2017 for European Patent Application No. EP15773744.6.
Office action dated Jul. 26, 2017 for U.S. Appl. No. 15/072,287.
Office action dated Aug. 2, 2017 for U.S. Appl. No. 14/836,390.

(56) References Cited

OTHER PUBLICATIONS

PCT/US2015/023956 International Search Report dated Sep. 30, 2015.

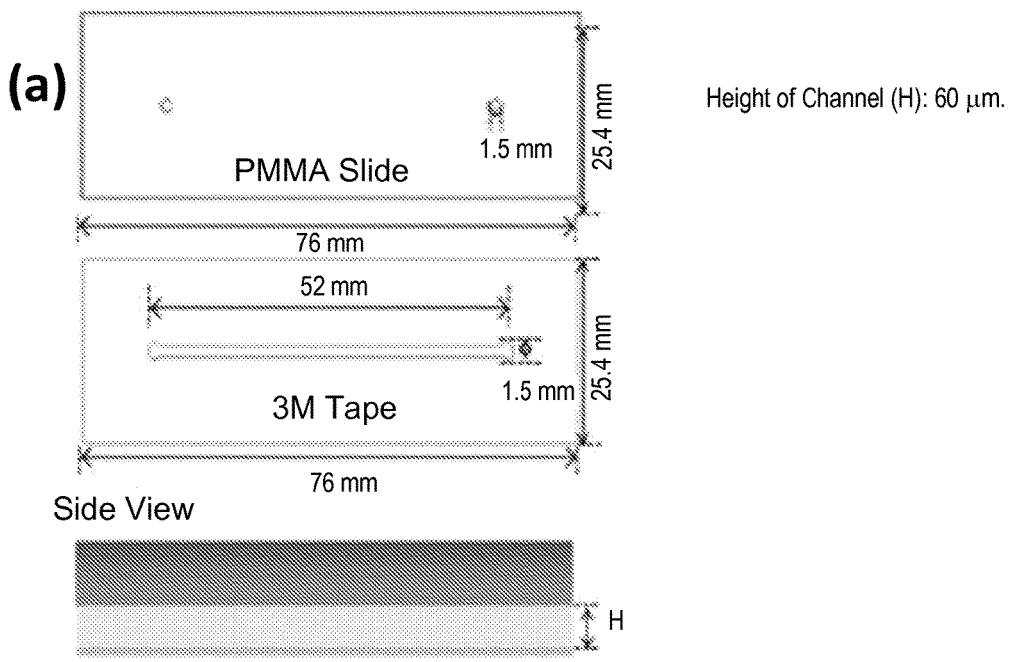
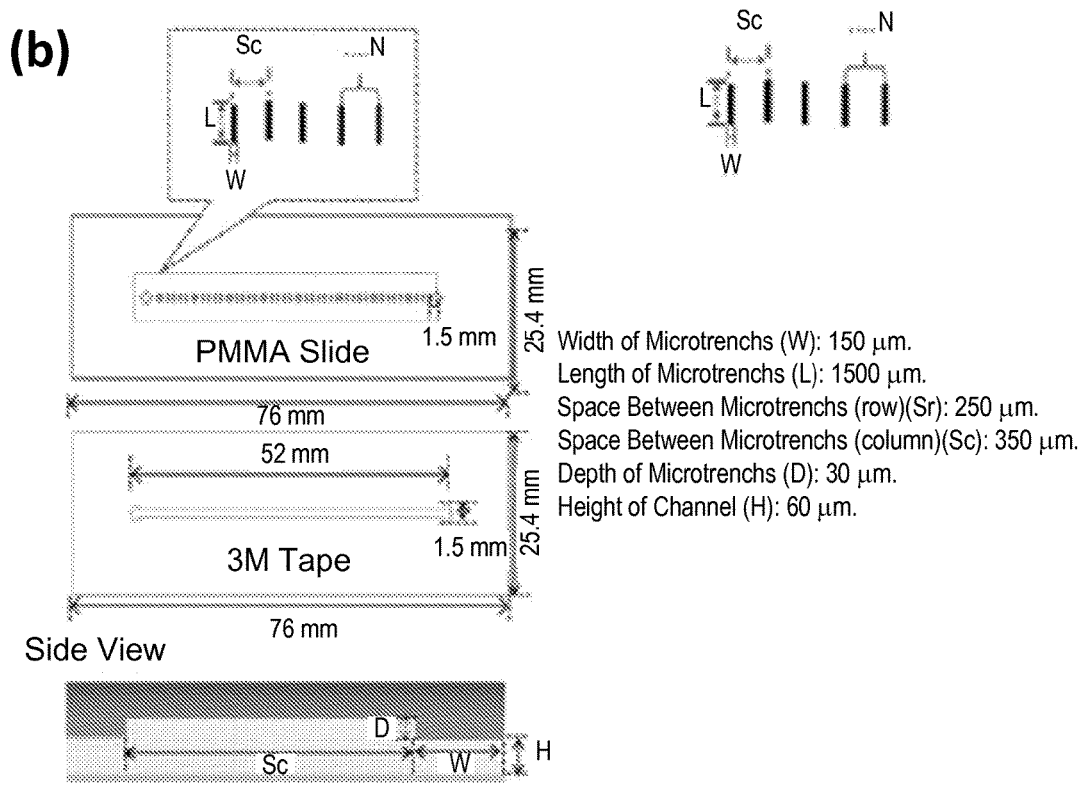
FIG. 10

(e) Top View

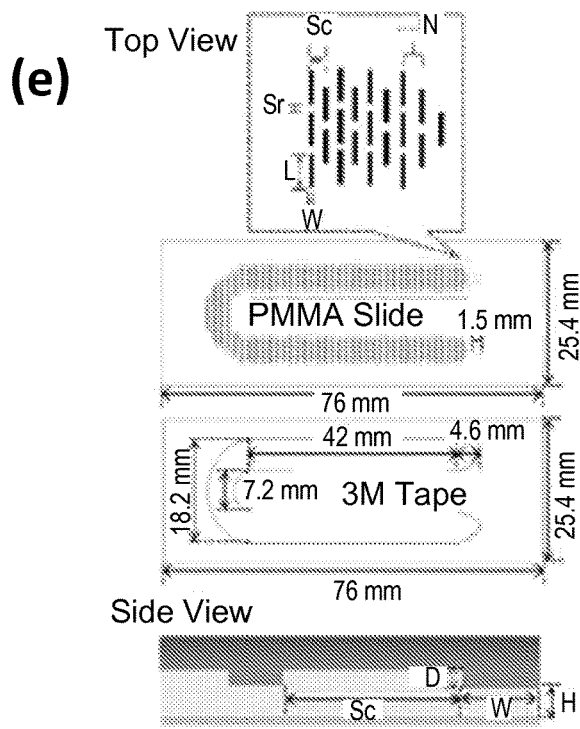
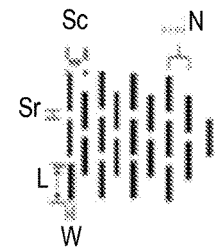

Width of Microtrenchs (W): 150 μm.
Length of Microtrenchs (L): 1500 μm.
Space Between Microtrenchs (row)(Sr): 250 μm.
Space Between Microtrenchs (column)(Sc): 350 μm.
Repeat of Microtrenchs (N): 45
Depth of Microtrenchs (D): 30 μm.
Height of Channel (H): 60 μm.

(f) Top View

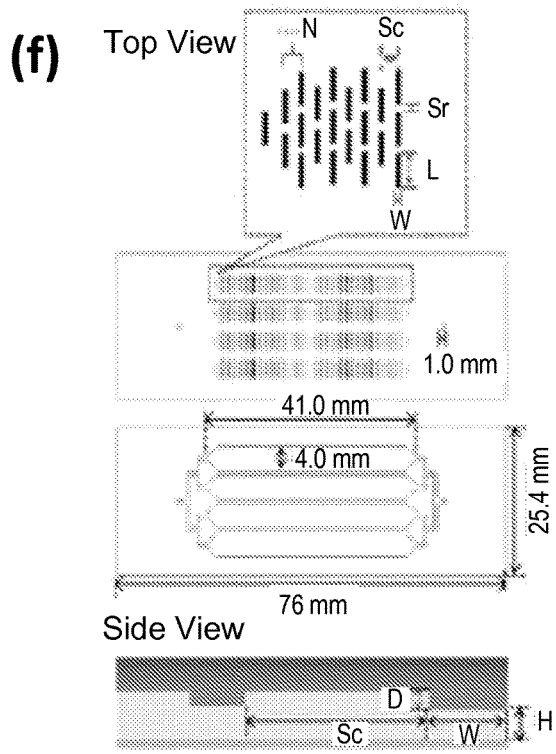
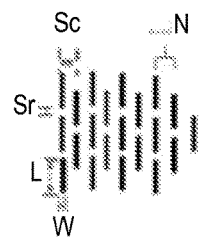

Width of Microtrenchs (W): 150 μm.
Length of Microtrenchs (L): 1000 μm.
Space Between Microtrenchs (row)(Sr): 250 μm.
Space Between Microtrenchs (column)(Sc): 350 μm.
Depth of Microtrenchs (D): 30 μm.
Height of Channel (H): 60 μm.

FIG. 12

SEQUENCE LISTING

<160> NUMBER OF SEQ ID NOS: 2

<210> SEQ ID NO 1
<211> LENGTH: 111
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Gly Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Phe Gly Arg
                85                  90                  95

Ser Val Asp Phe Trp Gly Gln Gly Thr Ser Val Thr Val Ser Ser
            100                 105                 110

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr His Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Ile Tyr Tyr Cys Ala Gln Asn
                85                  90                  95

Leu Glu Asn Pro Arg Thr Phe Gly Gly Gly Thr Lys Leu Glu Ile Lys
            100                 105                 110
```

METHODS AND SYSTEMS FOR CANCER DIAGNOSIS AND PROGNOSIS

CROSS-REFERENCE

This application is a National Stage Entry of PCT Application PCT/US2015/023956, filed Apr. 1, 2015, which claims the benefit of U.S. Provisional Application No. 61/973,348, filed Apr. 1, 2014, and U.S. Provisional Application No. 61/975,699, filed Apr. 4, 2014, which applications are incorporated herein by reference.

BACKGROUND

The study of rare cells, such as circulating tumor cells (CTCs), may aid in detection, diagnostics, and prognosis of diseases as well as in clinical care and drug discovery. For example, isolation and analysis of circulating tumor cells can be important for determining the origin of a tumor or understanding the process of tumor metastasis. Rare cells may be hard to capture due to their relatively low abundance in blood samples. Rare cells, like circulating tumor cells, may be fragile. A variety of techniques, such as immunomagnetic isolation, cell-size based filtration, antibody-functionalized microfluidic devices, fiber-optic array scanning technology, dielectrophoresis, passive cell sorting, negative selection, ensemble-decision aliquot ranking for isolating rare cells may have a low limit of detection and/or variation in reproducibility of results. Thus, there is a need for systems and methods for isolating rare cells such as CTCs in a format that is compatible with subsequent molecular analyses and clinical utility in detection of cancers and other diseases.

SUMMARY

The present disclosure relates to methods, compositions, and systems for isolating target particles of interest such as circulating tumor cells (CTCs), circulating rare cells (CRCs), stem cells (e.g. tumor stem cells and bone marrow stem cells), fetal cells, bacteria, vires, epithelial cells, endothelial cells or the like. Isolated target cells may be viable and useful for cell culture and growing in vitro and in vivo, cell preservation, detection, molecular analysis and clinical applications. The systems and methods may aid in cancer diagnosis, prognosis and treatment.

Thus, in one aspect, a method is provided. The method comprises: (a) using a microfluidic device, selectively enriching rare cells from a heterogeneous cell sample derived from a subject, wherein the microfluidic device comprises a non-fouling composition and has a capture efficiency for the rare cells of at least 40%; and (b) releasing captured rare cells from the microfluidic device while maintaining at least 40% of the released rare cell viable.

In some embodiments, the method further comprises analyzing the released rare cells thereby assessing presence, absence, severity, metastasis, tissue of origin of a condition in the subject. In some embodiments, the condition is cancer and the heterogeneous cell sample is a blood sample. In some embodiments, the condition is a benign disease. In some embodiments, the rare cells are CTCs. In some embodiments, analyzing comprises enumerating CTC's, enumerating viable CTCs, or performing a molecular analysis assay on the CTCs. In some embodiments, the condition is cancer and assessing the severity comprises determining a cancer stage. In some embodiments, the cancer stage comprises dysplasia, stage I, stage II, stage III, or stage IV cancer. In some embodiments, the method further comprises repeating steps (a) and (b) at a second time point. In some embodiments, the analyzing comprises comparing a number of released viable CTCs to a cutoff value. In some embodiments, the cutoff value is 3 rare cells and the blood sample has a volume equal to or up to 6 mL. In some embodiments, the blood sample has a volume equal to up to 2 mL. In some embodiments, assessing the severity comprises determining a cancer stage, and wherein the cancer stage comprises dysplasia, stage I, stage II, stage III, or stage IV cancer. In some embodiments, the method further comprises selecting a drug therapy for the subject based on the cancer stage. In some embodiments, the assessing determines the presence or absence of dysplasia or stage I cancer and occurs before an imaging diagnosis. In some embodiments, the imaging diagnosis comprises an ultrasound, a CT, an MRI, a PET, or a palpation analysis. In some embodiments, the condition is a colon disease, GI disease, or ovarian/endometrial diseases and wherein the analyzing the released rare cells comprises staining the released rare cells with DAPI, anti-CK20, and anti-CD45. In some embodiments, the condition is a breast disease or prostate disease, and wherein the analyzing of the released rare cells comprises staining the released rare cells with anti-PSA and anti-PSMA. In some embodiments, the condition is a breast disease, and wherein analyzing the released rare cells comprises staining the released rare cells with one or more markers selected from the group consisting of anti-CK7 anti-HER2, anti-ER, and anti-PR. In some embodiments, the condition is a lung disease, and wherein analyzing the released rare cells comprises staining the released rare cells with one or more markers selected from the group consisting of anti-CK7, anti-TTF1, and anti-EGFR. In some embodiments, the condition is cancer and wherein analyzing the released rare cells comprises staining the rare cells with anti-pan-CK or anti-CK18. In some embodiments, the condition is micrometastases.

In another aspect, a method of assessing a cancer origin in a subject is provided. The method comprises: using a microfluidic device, selectively enriching rare cells from a heterogeneous cell sample; staining the enriched rare cells with a panel of antibodies, wherein the panel of antibodies comprises two or more different types of antibodies; and predicting a cancer origin for the rare cells based on the staining result.

In some embodiments, predicting a cancer origin comprises 1) determining presence of carcinoma cells and 2) determining the cancer origin if carcinoma cells are present. In some embodiments, the panel of antibodies comprises anti-panCK, anti-CK18, anti-CK7, anti-TTF-1, anti-CK20, anti-CDX-2, anti-PSA, or anti-PSMA. In some embodiments, the cancer origin comprises breast cancer, lung cancer, pancreatic cancer, colorectal cancer, prostate cancer, or cancer of other origin. In some embodiments, the heterogeneous cell sample is a blood sample having a volume equal to or up to 6 mL. In some embodiments, the blood sample has a volume equal to or up to 2 mL. In some embodiments, the method further comprises selecting a drug therapy for the subject based on the progression of cancer.

In another aspect, a method of releasing target cells captured on a microfluidic surface is provided. The method comprises: flowing air foam across the microfluidic surface, wherein the microfluidic surface comprises a lipid bi-layer and the target cells are captured on a top layer of the lipid bi-layer; and detaching the top layer, thereby releasing the target cells captured on the top layer.

In some embodiments, the captured target cells are released with at least 40% efficiency and 40% viability. In some embodiments, the method further comprises 1) staining the target cells with a panel of antibodies and 2) identifying the origin source based on the staining result. In some embodiments, the panel of antibodies comprise at least two of anti-panCK, anti-CK18, anti-CK7, anti-TTF-1, anti-CK20 mixed with anti-CDX-2, anti-PSA mixed with anti-PSMA. In some embodiments, the method further comprises analyzing the released target cells thereby assessing presence, absence, severity, metastasis, tissue of origin of a condition in a subject.

In another aspect, a method of releasing target cells captured on a microfluidic surface comprising a non-fouling composition is provided. The method comprises: affecting a state of the non-fouling composition; and releasing the target cells, wherein the target cells are released as a result of the affected state of the non-fouling composition.

In another aspect, a method of assessing presence, absence, or severity of a condition in a subject is provided. The method comprises: performing a diagnostic test, wherein the diagnostic test has an ROC curve with an area under the curve of 0.75 or more.

In some embodiments, the condition is cancer. In some embodiments, the condition is stage I or pre-stage I cancer. In some embodiments, the method further comprises comparing a CTC cell count in a blood sample to a cutoff value based on the ROC curve, thereby assessing presence or absence of the condition.

In another aspect, a method of assessing presence, absence, or severity of a condition in a subject is provided. The method comprises: using a microfluidic device, selectively enriching rare cells from a patient blood sample having a volume equal to or less than 7 mL; and analyzing the rare cells thereby assessing the presence or severity of the condition in the subject.

In some embodiments, the patient blood sample has a volume equal to or less than 2 mL. In some embodiments, the condition is dysplasia or stage I cancer. In some embodiments, analyzing the rare cells comprises comparing a rare cell number in the patient blood sample to a cutoff value, wherein the cutoff value is generated based on a test having an area under a ROC curve of 0.75 or more. In some embodiments, rare cells are CTCs and wherein the condition is cancer.

In another aspect, a method of determining presence or absence of dysplasia or stage I cancer in a subject is provided. The method comprises: using a microfluidic device, selectively enriching rare cells from a heterogeneous cell sample derived from the subject; and determining a number of enriched rare cells and comparing the number to a cutoff value, thereby determining presence or absence of dysplasia or stage I cancer in the subject.

In some embodiments, rare cells are CTCs. In some embodiments, determining presence or absence is done before imaging. In some embodiments, imaging is unable to detect or determine presence or absence of dysplasia or stage I cancer.

In another aspect, a method of assessing the presence or severity of a condition in a subject is provided. The method comprises: using a microfluidic device, selectively enriching rare cells from a heterogeneous cell sample derived from the subject with a capture efficiency of at least 40%; releasing the rare cells from the microfluidic device while maintaining at least 40% of the rare cell viable; and analyzing the released rare cells thereby assessing the presence or severity of the condition in the subject.

In some embodiments, the presence or severity of the condition is assessed with a sensitivity and specificity defined by an area under an ROC curve, wherein the area under the ROC curve is 0.75 or more. In some embodiments, the condition is cancer. In some embodiments, condition is a benign disease. In some embodiments, the rare cells are CTCs. In some embodiments, analyzing the released rare cells involves enumerating CTC's, enumerating viable CTCs, and performing a molecular analysis assay on the CTCs. In some embodiments, the condition is cancer and assessing the severity comprises determining a cancer stage. In some embodiments, the cancer stage comprises dysplasia, stage I, stage II, stage III, or stage IV cancer. In some embodiments, the method further comprises 1) generating a cutoff value based on the area under the curve and 2) determining presence or severity of the condition based on the cutoff value. In some embodiments, determining presence or severity of the condition comprises comparing the cutoff value against a released rare cell number within the heterogeneous cell sample. In some embodiments, the cutoff value is 3 or more rare cells and the heterogeneous cell sample is a patient blood sample having a volume equal to or less than 2 mL. In some embodiments, the condition is cancer or disease. In some embodiments, assessing the severity comprises determining a cancer stage, and wherein the cancer stage comprises dysplasia, stage I, stage II, stage III, or stage IV cancer. In some embodiments, the heterogeneous cell sample is a patient blood sample having a volume equal to or less than 2 mL. In some embodiments, the condition is a colon disease and wherein analyzing the released rare cells comprises staining the rare cells with DAPI, CK20, and CD45. In some embodiments, the condition is a breast or prostate disease, and wherein analyzing the released rare cells comprises staining the rare cells with anti-PSA and/or anti-PSMA. In some embodiments, the condition is cancer and wherein analyzing the released rare cells comprises staining the rare cells with anti-pan-CK or anti-CK18. In some embodiments, the condition is micrometastases. In some embodiments, the condition is cancer, and wherein the presence of the condition is determined at a stage undetectable by imaging techniques comprising CT, PET, ultrasound, or MRI.

In another aspect, a method of assessing a cancer origin in a subject is provided. The method comprises: using a microfluidic device, selectively enriching rare cells from a heterogeneous cell sample derived from the subject; releasing the rare cells from the microfluidic device; staining the rare cells with a panel of antibodies, wherein the panel of antibodies comprises two or more different types of antibodies; and predicting a cancer origin for the rare cells based on the staining result.

In some embodiments, predicting a cancer origin comprises 1) determining presence of carcinoma cells and 2) determining the cancer origin if carcinoma cells are present. In some embodiments, the panel of antibodies comprises anti-panCK, anti-CK18, anti-CK7, anti-TTF-1, anti-CK20, anti-CDX-2, anti-PSA, or anti-PSMA. In some embodiments, the cancer origin comprises breast cancer, lung cancer, pancreatic cancer, colorectal cancer, prostate cancer, or cancer of other origin. In some embodiments, the the rare cells are collected from peripheral blood from a patient in an amount equal to or less than 2 mL.

In another aspect, a method of releasing target cells captured on a microfluidic surface is provided. The method comprises: flowing a fluid comprising air bubbles across the microfluidic surface, wherein the microfluidic surface includes a lipid bi-layer and binding moieties that selectively bind the target cells, and wherein the binding moieties are coupled to a top layer of the lipid bi-layer; and detaching the top layer of the lipid bi-layer, thereby detaching the binding moieties coupled to the top layer releasing the target cells bound to the binding moieties.

In some embodiments, binding moieties bind the target cells with at least 40% efficiency. In some embodiments, releasing of the target cells releases the cells with at least 40% efficiency. In some embodiments, the released target cells have a viability of at least 40%. In some embodiments, the method further comprises determining an origin source for the target cells. In some embodiments, determining the origin source comprises 1) staining the target cells with a panel of antibodies and 2) identifying the origin source based on the staining result. In some embodiments, the panel of antibodies comprise at least two of anti-panCK, anti-CK18, anti-CK7, anti-TTF-1, anti-CK20 mixed with anti-CDX-2, anti-PSA mixed with anti-PSMA. In some embodiments, the foam composition comprises air bubbles, a majority of which has a diameter smaller than a width of the microfluidic surface or a height of a microfluidic channel.

Another aspect the disclosure provides for a foam composition having a volume greater than 1 milliliter, wherein the foam composition comprises air bubbles, wherein greater than 50% of the air bubbles comprise a diameter from 10 microns to 100 microns, and wherein greater than 80% of the volume of the foam composition is air. In some embodiments, greater than 60% of the air bubbles comprise a diameter from 10 microns to 100 microns. In some embodiments, greater than 70% of the air bubbles comprise a diameter from 10 microns to 100 microns. In some embodiments, greater than 80% of the air bubbles comprise a diameter from 10 microns to 100 microns. In some embodiments, greater than 90% of the air bubbles comprise a diameter from 10 microns to 100 microns. In some embodiments, the foam composition comprises a volume greater than 2 milliliters. In some embodiments, the foam composition comprises a volume greater than 3 milliliters. In some embodiments, the foam composition comprises a volume greater than 4 milliliters. In some embodiments, the foam composition comprises a volume greater than 5 milliliters. In some embodiments, the foam composition is isotonic. In some embodiments, the foam composition comprises Bovine Albumin Serum (BSA). In some embodiments, the foam composition comprises cell culture medium. In some embodiments, the foam composition comprises a protein-containing solution compatible with cell culture. In some embodiments, a ratio of liquid to air in the foam composition is at least 1.5:1. In some embodiments, a ratio of liquid to air in the foam composition is at least 2:1. In some embodiments, a ratio of liquid to air in the foam composition is at least 3:1. In some embodiments, a ratio of liquid to air in the foam composition is at least 4:1. In some embodiments, the ratio of liquid to air in the foam composition is at least 5:1. In some embodiments, greater than 90% of the volume of the foam composition is air. In some embodiments, greater than 95% of the volume of the foam composition is air.

In one aspect, the disclosure provides for a method for removing a particle from a surface comprising: flowing a foam composition over a surface, and removing the particle from the surface, wherein the foam composition comprises air bubbles, and wherein at least 50% of the air bubbles comprise a diameter from 10 microns to 100 microns. In some embodiments, the flowing comprises a linear velocity of at least 2.5 mm/s. In some embodiments, the flowing comprises a linear velocity of at most 4 mm/s. In some embodiments, the flowing comprises a linear velocity from 2.6 mm/s to 3.9 mm/s. In some embodiments, the flowing comprises a linear velocity of at least 0.5 mm/s. In some embodiments, the flowing comprises a linear velocity of at most 4 mm/s. In some embodiments, the flowing comprises a linear velocity from 0.5 mm/s to 4 mm/s. In some embodiments, the flowing removes greater than 60% of the non-fouling composition. In some embodiments, the flowing removes greater than 70% of the non-fouling composition. In some embodiments, the flowing removes greater than 80% of the non-fouling composition. In some embodiments, the flowing removes greater than 90% of the non-fouling composition. In some embodiments, the surface comprises a set of microstructures. In some embodiments, the surface comprises a non-fouling composition. In some embodiments, the non-fouling composition comprises a polymer and a binding moiety. In some embodiments, the non-fouling composition comprises a lipid layer and a binding moiety. In some embodiments, the binding moiety is non-covalently coupled to the non-fouling composition. In some embodiments, the binding moiety is covalently coupled to the non-fouling composition. In some embodiments, the binding moiety is embedded in the non-fouling composition. In some embodiments, the binding moiety is coupled to the surface. In some embodiments, the lipid layer comprises a monolayer. In some embodiments, the lipid layer comprises a bilayer. In some embodiments, the lipid layer comprises liposomes. In some embodiments, the lipid layer comprises two or more of a lipid monolayer, bilayer, or liposomes. In some embodiments, the binding moiety comprises an anti-EpCAM antibody. In some embodiments, the binding moiety comprises an anti-HER2 antibody. In some embodiments, the binding moiety comprises an antibody. In some embodiments, the surface comprises a bound cell. In some embodiments, the bound cell is removed by the foam composition. In some embodiments, the bound cell is bound to the surface by a binding moiety. In some embodiments, the cell is a rare cell. In some embodiments, the cell is a circulating tumor cell. In some embodiments, the non-fouling composition prevents binding of at least 50% of non-target particles. In some embodiments, the non-fouling composition prevents binding of at least 60% of non-target particles. In some embodiments, the non-fouling composition prevents binding of at least 70% of non-target particles. In some embodiments, the non-fouling composition prevents binding of at least 80% of non-target particles. In some embodiments, the non-fouling composition prevents binding of at least 90% of non-target particles. In some embodiments, the foam composition is generated by a method for generating a foam composition comprising: combining a liquid solution and air in a ratio of at least 1.5:1; and vortexing the liquid solution and the air for up to 30 seconds, thereby generating air bubbles, wherein at least 50% of the air bubbles comprise a diameter from 10 microns to 100 microns. In some embodiments, the foam composition is generated by a method for generating a foam composition comprising: introducing a solution into a first container, transferring the solution into a second container, wherein the second container comprises air, and wherein the transferring occurs through a hole, transferring the solution from the second container into the first container through the hole, and generating foam, wherein the foam comprises air bubbles, and wherein at least 50% of the air bubbles comprise a diameter from 10 microns to 100 microns. In some embodiments, the foam composition is generated by a method for generating a foam composition comprising: drawing a solution through a membrane, wherein the solution comprises a ratio of at least 1:1.5 air to liquid, wherein the drawing produces air bubbles, and wherein at least 50% of the air bubbles comprise a diameter from 10 microns to 100 microns. In some embodiments, the surface comprises a microfluidic channel.

In one aspect, the disclosure provides for a method for generating a foam composition comprising: combining a liquid solution and air in a ratio of at least 1.5:1, vortexing the liquid solution and the air for up to 30 seconds, thereby generating air bubbles, wherein at least 50% of the air bubbles comprise a diameter from 10 microns to 100 microns. In some embodiments, the ratio is at least 2:1. In some embodiments, the ratio is at least 3:1. In some embodiments, the ratio is at least 4:1. In some embodiments, the ratio is at least 5:1. In some embodiments, at least 50% of the air bubbles comprise a diameter from 10 microns to 100 microns. In some embodiments, at least 60% of the air bubbles comprise a diameter from 10 microns to 100 microns. In some embodiments, at least 70% of the air bubbles comprise a diameter from 10 microns to 100 microns. In some embodiments, at least 80% of the air bubbles comprise a diameter from 10 microns to 100 microns. In some embodiments, at least 90% of the air bubbles comprise a diameter from 10 microns to 100 microns.

In one aspect the disclosure provides for a method for generating a foam composition comprising: introducing a solution into a first container, transferring the solution into a second container, wherein the second container comprises air, and wherein the transferring occurs through a hole; transferring the solution from the second container into the first container through the hole; and generating foam, wherein the foam comprises air bubbles, and wherein at least 50% of the air bubbles comprise a diameter from 10 microns to 100 microns. In some embodiments, the method is repeated. In some embodiments, the method is repeated at least 5 times. In some embodiments, the method is repeated 10 times. In some embodiments, the container comprises a syringe. In some embodiments, the hole comprises a diameter of at 2 millimeters. In some embodiments, the hole comprises a diameter of at most 100 micron. In some embodiments, at least 60% of the air bubbles comprise a diameter from 10 microns to 100 microns. In some embodiments, at least 70% of the air bubbles comprise a diameter from 10 microns to 100 microns. In some embodiments, at least 80% of the air bubbles comprise a diameter from 10 microns to 100 microns. In some embodiments, at least 90% of the air bubbles comprise a diameter from 10 microns to 100 microns. In some embodiments, a ratio of the solution to the air is at least 1.5:1. In some embodiments, a ratio of the solution to the air is at least 2:1. In some embodiments, a ratio of the solution to the air is at least 3:1. In some embodiments, a ratio of the solution to the air is at least 4:1. In some embodiments, a ratio of the solution to the air is at least 5:1.

In one aspect the disclosure provides for a method for generating a foam composition comprising: drawing a solution through a membrane, wherein the solution comprises a ratio of at least 1:1.5 air to liquid, wherein the drawing produces air bubbles, and wherein at least 50% of the air bubbles comprise a diameter from 10 microns to 100 microns. In some embodiments, the membrane comprises a fine pore membrane. In some embodiments, the membrane comprises a plurality of pores. In some embodiments, the pores comprise a diameter of 2 millimeters. In some embodiments, the membrane comprises an airstone. In some embodiments, the ratio is at least 2:1. In some embodiments, the ratio is at least 3:1. In some embodiments, the ratio is at least 4:1. In some embodiments, the ratio is at least 5:1. In some embodiments, at least 60% of the air bubbles comprise a diameter from 10 microns to 100 microns. In some embodiments, at least 70% of the air bubbles comprise a diameter from 10 microns to 100 microns. In some embodiments, at least 80% of the air bubbles comprise a diameter from 10 microns to 100 microns. In some embodiments, at least 90% of the air bubbles comprise a diameter from 10 microns to 100 microns.

In one aspect the disclosure provides for a method for generating a foam composition comprising: pumping a solution comprising a protein-containing solution, wherein said pumping produces air bubbles, and wherein at least 50% of said air bubbles comprise a diameter from 10 microns to 100 microns. In some embodiments, the pumping occurs only once. In some embodiments, the pumping mixes said protein-containing solution with atmospheric air.

Another aspect of the present disclosure features a cell capture/release platform for isolating target cells in a sample. The platform comprises a lipid conjugate comprising a lubricated composition and a binding agent that specifically binds the target cells, and wherein the lipid conjugate and the binding agent are linked through a linker. In some embodiments, the lipid conjugate is immobilized on a substrate. In some embodiments, the substrate is a planar device. In certain embodiments, the substrate is a microfluidic device.

Another aspect of the present disclosure features a method for isolating target cells in a sample. The method comprises the steps of (a) contacting the sample with a lipid conjugate comprising a lubricated composition and a binding agent that specifically binds the target cells, and wherein the lubricated conjugate and the binding agent are linked through a linke; (b) washing away the unbound cells; and (c) releasing the bound cells, thereby the target cells are isolated.

The sample described herein can be body fluid, dilution of body fluid, whole blood, urine, lymph or ascite. In some embodiments, the sample is less than 9 mL, less than 6 mL, less than 4 mL or less than 3 mL, less than 2 mL or less than 1 mL in volume. In some embodiments, the sample is about 8 mL, about 6 mL, about 4 mL, about 2 mL or about 1 mL in volume.

The target cells described herein include, but not limited to, tumor cells, stem cells, pathogens, T-cells, cardiomyocytes, circulating tumor cells, circulating epithelial cells and circulating endothelial cells.

In some embodiments, the method further comprises enriching the isolated cells.

The isolated cells remain viable. In some embodiments, the isolated cells have cell viality greater than 95%, greater than 90%, greater than 80%, greater than 70%, greater than 60%, greater than 50%, greater than 40%, or greater than 30%. In some embodiments, at least about 90%, at least about 80%, at least about 70%, at least about 60%, at least about 50%, at least about 40%, or at least about 30% of the isolated cells are viable.

The binding agent disclosed herein specifically binds the target cell surface. In some embodiments, the target cells are epithelial cells, and the binding agent is an antibody against epithelial cell adhesion molecules membrane protein (anti-EpCAM). In a preferred embodiment, the binding agent is an anti-EpAb 4-1.

The lubricated composition disclosed herein is a lipid moiety, lipid mixture, lipid monolayer, lipid bilayer, liposome, lipopolymer or polyethylene glycol. In a preferred embodiment, the lubricated composition is a supported lipid bilayer (SLB).

The target cells are released without disrupting the cells, thereby the isolated cells remain intact and viable. In some embodiments, the target cells are released via the disruption of the lipid conjugate. In some embodiments, the target cells are released via the disruption of the lubricated composition (such as SLB).

In some embodiments, the washing in step (b) is performed by applying a shear stress to the lubricated composition. In some embodiments, the shear stress is about 0.5 to about 30 dynes/cm$^2$. In some embodiments, the shear stress is about 0.5, about 1, about 2.5, about 5, about 7.5, about 10, about 12.5, about 15, about 20 or about 30 dynes/cm$^2$.

In some embodiments, the releasing in step (c) is performed by applying a gentle sweeping force. The gentle sweeping force includes, but not limited to, a shear of air bubbles, a shear of air foam, a shear of emulsive fluid, ultrasonic vibration or an oil phase. The gentle sweeping force provides a hydrophobic interaction with the lubricated composition.

In some embodiments, the method further comprises enriching the isolated cells. In some embodiments, the enrichment of isolated cells is at least 200 fold, at least 400 fold, at least 600 fold, at least 800 fold, or at least 1000 fold.

In another aspect, the present disclosure features a method of culturing and growing the isolated cells in vitroor in vivo. The method includes the steps of (a) isolating the target cells according to the methods disclosed herein, and (b) maintaining the isolated cells under conditions effective to culture and grow the viable target cells in vivo or in vitro.

Another aspect of the present disclosure features a method of preserving viable target cells. The method includes the steps of (a) isolating the target cells according to the methods disclosed herein, and (b) preserving the isolated cells under suitable conditions for long term storage.

In another aspect, the present disclosure features a method of performing molecular analysis on the isolated cells. The method includes the steps of (a) isolating the target cells according to the methods described herein, and (b) performing molecular analysis.

Another aspect of the present disclosure features a method of detecting target cells in a subject. The method includes the step of (a) isolating the target cells according to the methods described herein; (b) detecting the target cells by staining. The subject is having or suspected of having a disease/cancer.

Another aspect of the present disclosure features a a method of assessing cancer progression in a patient suffering from cancer. The method comprises the steps of (a) isolating circulating tumor cells (CTCs) from the patient, and (b) performing one or more cellular or molecular analyses on the CTCs to determine cancer progression in the patient.

The isolated circulating tumor cells (CTCs) are substantially pure. In some embodiments, the substantially pure population of CTCs comprises no more than 20% of non-CTC cells. In some embodiments, the substantially pure population of CTCs comprises no more than 10% of non-CTC cells. In some embodiments, the substantially pure population of CTCs comprises no more than 5% of non-CTC cells.

Examples of the cancers include, but are not limited to, lung cancer, esophageal cancer, bladder cancer, gastric cancer, colon cancer, skin cancer, papillary thyroid carcinoma, colorectal cancer, breast cancer, lymphoma, pancreatic cancer, prostate cancer, ovarian cancer, pelvic cancer, and testicular cancer.

In some embodiments, the one or more cellular or molecular analyses comprise morphological analysis, genomics analysis, epigenomics analysis, transcriptomics analysis, proteomics analysis, or any combination thereof.

In some embodiments, the one or more cellular or molecular analyses comprise determining one or more DNA mutations in the CTCs.

In some embodiments, the DNA mutation comprises an insertion, a deletion, a substitution, a translocation, a gene amplification, or any combination thereof.

In some embodiments, the DNA mutation is located in a gene selected from the group consisting of KRAS, APC, TP53, BRAF, PTEN, EGFR, ERCC1, RRM1, ELM4, HER2, and ALK.

In some embodiments, the one or more cellular or molecular analyses comprise determining protein expression level of a cancer specific gene in the CTCs. In some embodiments, the one or more cellular or molecular analysis comprise determining RNA expression level of a cancer specific gene in the CTCs.

In some embodiments, the method further comprises detecting the expression of one or more cancer-specific markers in the CTCs by staining, and enumerating the stained cells. The stage and/or prognosis of tumors in the patient can be determined based upon the combination results of molecular analysis and enumeration of the cancer-specific CTCs.

A number of cancer-specific markers are known in the art. In some embodiments, the cancer specific marker is cytokeratin, CDX1, CDH17, prostate-specific antigen (PSA), prostate specific membrane antigen (PSMA), mucin-1 (MUC-1), human epidermal growth factor receptor 2 (HER2), chorionic gonadotropin (hCG), alpha fetoprotein (AFP), hepato-cellular carcinoma (HCC), N-cadherin, epidermal growth factor receptor (EGFR), ERCC1, androgen receptor (AR), human equilibrative nucleoside transporter 1 (hENT1), RRM1, or carcinoembryonic antigen (CEA), CD 44 and p53, epithelial cell adhesion molecule (EpCAM), GD2, GM2, GM1, GD1a, GT1b, A2B5, Tf, Tn, Globo H, CD133, CD24, CD44, CD90, ER, or PR.

Further, the present disclosure features a method assessing the presence and/or the severity of a disease in a subject, the method comprising (a) isolating circulating tumor cells (CTCs) from the subject; (b) detecting the expression of one or more cancer-specific markers in the CTCs by staining; (c) enumerating the stained cells; and wherein the number and/or change in number of stained cells compared to a control is an indication of the presence and/or the severity of the disease; thereby, assessing the presence and/or the severity of the disease.

In some embodiments, the method further comprises performing one or more cellular or molecular analyses on the CTCs, and the presence and/or the severity of the disease is determined based on the combination results of molecular analyses and enumeration of the disease-specific CTCs.

In some embodiments, the disease is a cancer. The increased number of stained cells is an indication of cancer poor prognosis or metastasis.

In some embodiments, the disease is a precancerous disorder. Examples of precancerous disorders include actinic keratosis, Barrett's esophagus, atrophic gastritis, Dyskeratosis congenita, Sideropenic dysphagia, Lichen planus, Oral submucous fibrosis, Solar elastosis and cervical dysplasia.

The present disclosure also features a method for detecting colorectal cancer or gastrointestinal (GI) tract diseases in a subject. The method includes the steps of (a) isolating circulating tumor cells (CTCs) from the subject; (b) detecting the expression of one or more markers selected from the group consisting of DAPI, CK20, CD45, CDH17, CDX2, CK7, CEA, panCK, TCN, SULT2B1, ALDOB, COL11A1, PI3, CCL20, MTHFD11, IL-1b, SRPX2, SLC04A1, TESC, and IL-23a in the CTCs by staining; (c) enumerating the stained cells; and wherein the number and/or change in number of stained cells as compared to a control is an indication of the presence and/or the severity of colorectal cancer or gastrointestinal (GI) tract diseases.

In some embodiments, the markers includes CK20 and one or more selected from the group consisting of DAPI, CD45, CDH17, CDX2, CK7, CEA, panCK TCN, SULT2B1, ALDOB, COL11A1, PI3, CCL20, MTHFD11, IL-1b, SRPX2, SLC04A1, TESC, and/or IL-23a.

In some embodiments, the markers are selected from the group consisting of DAPI, CK20, CD45, and CEA. In some embodiments, the markers are selected from the group consisting of DAPI, CK20 and CD45.

In some embodiments, the presence and/or the severity of colorectal cancer or gastrointestinal (GI) tract diseases is indicated by the number or a change in the number of stained cells in the expression of DAPI+/CK20+/CD45−.

In some embodiments, the subject is a human patient having or suspected of having gastrointestinal (GI) tract diseases. The gastrointestinal tract disease includes, but not limited to, Barret's esophagus, gastric ulcer, gastritis, leiomyoma, polyps, Crohn's disease, ulcerative colitis, pancreatitis, adenocarcinoma, mucinous adenocarcinoma, carcinoid tumor, squamous cell carcinoma, lymphoma, and sarcoma.

In some embodiments, the subject is a human patient is having a colorectal cancer (CRC). In certain embodiments, the colorectal cancer patient is suffering from colorectal cancer is stage 0, stage I, stage II, stage III and/or stage IV colorectal cancer.

The details of one or more embodiments of the invention are set forth in the description below. Other features or advantages of the present invention will be apparent from the following drawings and detailed description of several embodiments, and also from the appending claims.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10 illustrates the construction and dimension of microfluidic channel design A and B.

FIG. 12 illustrates the construction and dimension of microfluidic channel design E and F.

DETAILED DESCRIPTION

General Overview

The disclosure provides for compositions and methods for capturing and removing particles from a non-fouling composition. The particles may be particles of interest, such as cells including circulating tumor cells (CTCs), circulating rare cells (CRCs), stem cells (e.g. tumor stem cells and bone marrow stem cells), fetal cells, bacteria, vires, epithelial cells, endothelial cells or the like. The particles of interest can be flowed through a channel which can comprise a surface. The surface can be coated with a binding moiety, to which the particles of interest can attach. The surface can comprise a non-fouling composition. A non-fouling composition can refer to a lipid composition that lessens the binding of non-specific particles. In other words, a non-fouling composition can enrich the purity of the particles of interest by reducing the binding of non-specific particles to the composition. When the particles of interest are captured by the binding moiety and the non-fouling composition, they can be removed by a gentle sweeping force or a foam composition comprising air bubbles. For example, the gentle sweeping force may be a shear of air bubbles, a shear of air foams, a shear of emulsive fluid, ultrasonic vibration or an oil phase. The foam composition can remove the particle of interest, the binding moiety and/or the non-fouling composition.

Figure 1:
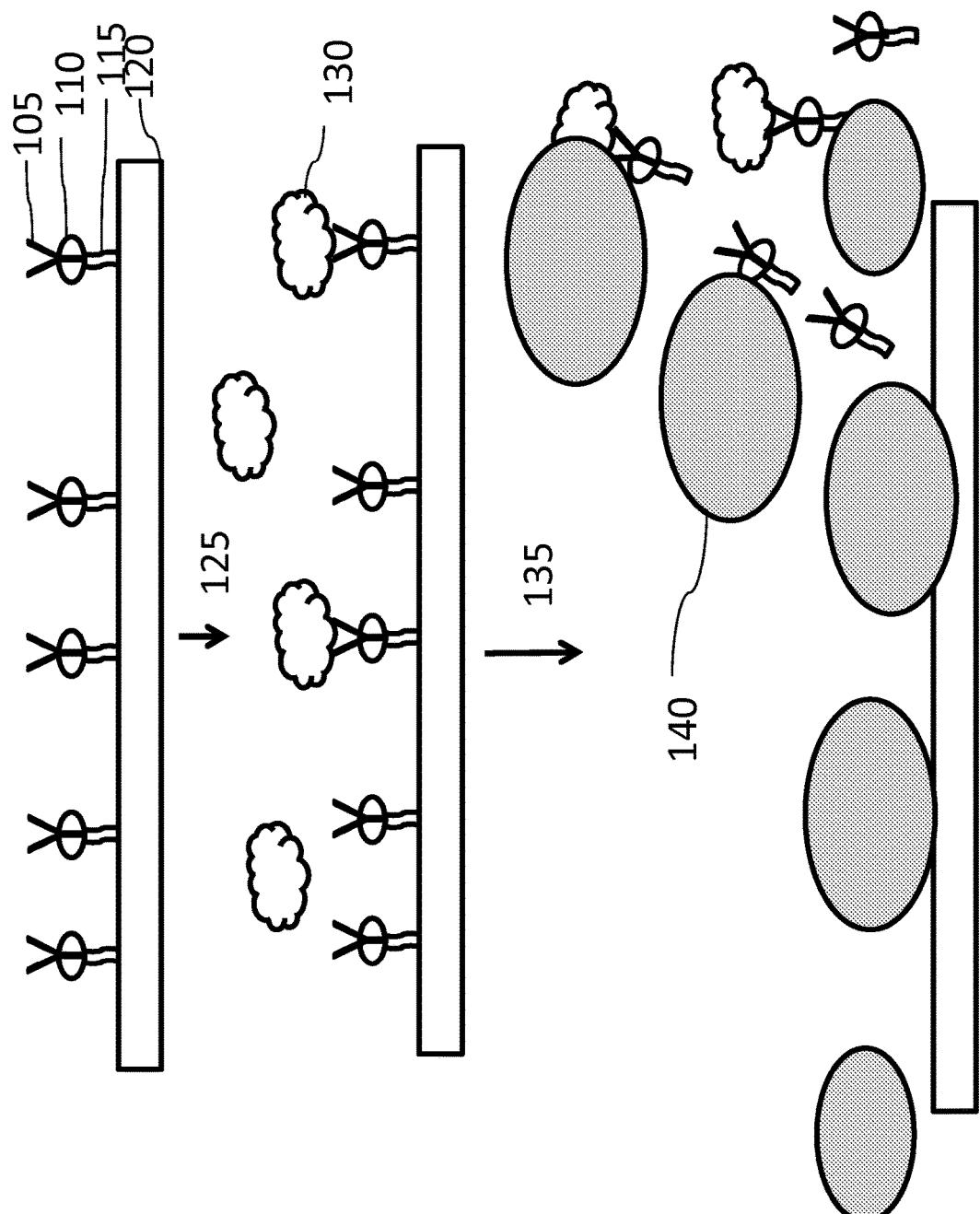
FIG. 1 illustrates an exemplary embodiment of the methods of the disclosure.

An exemplary embodiment of the method is diagrammed in FIG. 1. A surface 120 can be coated in a non-fouling composition 115. The non-fouling composition 115 can be attached to a linker 110. The linker 110 can be conjugated to a binding moiety 105. The binding moiety 105 can be an antibody. The surface 120 can be contacted 125 with a sample comprising a particle of interest 130. In some instances, the particle of interest 130 is a cell. In some instances, the particle of interest 130 is a rare cell. The particle of interest 130 can bind to the binding moiety 105. A foam composition comprising air bubbles 140 can be flowed over 135 the surface 120. The air bubbles 140 can remove the non-fouling composition 115 from the surface 120, along with any bound cells 130. While FIG. 1 shows air bubble 140 removing a single particle of interest, it shall be understood that the air bubble may remove a plurality of particles of interest and/or non-fouling compositions.

Particles of interest (e.g., CTCs) may be further analyzed and utilized in clinical applications such as cancer diagnosis, prognosis, and treatment. The aforementioned systems and methods may enable capture and release of viable CTCs that is sensitive and compatible with means to confirm a disease (e.g., compatible with subsequent molecular analysis). For example, the system and methods provided herein may allow capture and release of viable CTCs, allowing live cancer cells to be studied in vitro or propagated to enable analyses with additional techniques to obtain results that may lead to actionable therapy guidance and may benefit therapeutic development. In some instances, the additional techniques may include genome-wide molecular analyses to study mutations or epigenetic changes. In some instances, the additional techniques may include pathway analyses for pharmaceutical intervention that targets cancer stem cells. While application with respect to cancer is primarily discussed herein, it shall be understood that the compositions and methods described herein may be used in clinical applications relating to non-cancerous conditions. For example, clinical applications may relate to polyps, benign diseases such as inflammatory bowel disease (IBD), arthritis, colitis, and the like. For example, when active, CTC count may be high and detection rate high.

Surfaces

The devices herein useful for the selective capture and efficient release of particles of interest such as CTCs can include one or more surfaces. Such surfaces may be flat, curved, planar, circular, irregularly shaped, and/or comprise topological features (e.g., microstructures or nanostructures such as nanoparticles, nanowires, etc). The surfaces may be the same. The surfaces may be different (e.g., a top surface may comprise microstructures, and a bottom surface may be flat).

Exemplary surfaces can include, but are not limited to, a biological microelectromechanical surface (bioMEM) surface, a microwell, a slide, a petri dish, a cell culture plate, a capillary, a tubing, a pipette tip, and a tube. A surface can be solid, liquid, and/or semisolid. The non-fouling composition may be incorporated into cell cultural dishes, microfluidic channels, microfluidic chips, filtration filter, capillaries, tubes, beads, nanoparticles, or the like. A surface can have any geometry (e.g., a surface can be planar, tilted, jagged, have topology).

A surface can comprise a microfluidic surface. A surface can be a part of, or may generate a microfluidic channel. A surface can be the surface of a slide, the inside surface of a wellplate or any other cavity.

The surface can be made of a solid material. Exemplary surface materials can include silicon, glass, hydroxylated poly(methyl methacrylate) (PMMA), aluminum oxide, plastic, metal, titanium oxide ($TiO_2$), Au, Ag, Pt, and the like.

A surface can be a part of, or may generate a channel. The channel can include a surface configured to capture the particle of interest (e.g., cell). The channel can be formed within a microfluidic device configured to capture the particle of interest from whole blood samples. Capture can be mediated by the interaction of a particle of interest (e.g., cell) with a binding moiety on a surface of the channel. For example, the channel can include microstructures coated with binding moieties. The microstructures can be arranged to isolate a particle of interest from a whole blood sample within the channel. Such a channel can be used to capture particle of interests from blood samples from patients, and can be useful both in cancer biology research and clinical cancer management, including the detection, diagnosis, and monitoring of cancer.

A channel can comprise three dimensions. The cross-section of the channel can be defined as two dimensions of the channel's volume (e.g., height and width). In some embodiments, the width of the channel may be about equal to or greater than 10 um, 20 um, 30 um, 40 um, 50 um, 60 um, 70 um, 80 um, 90 um, 100 um, 120 um, 150 um, 200 um, 250 um, 300 um, 500 um, 1 mm, 2 mm, 5 mm, 10 mm, 20 mm, 50 mm, or 100 mm. In some embodiments, the height of the channel may be about equal to or greater than 20 um, 30 um, 40 um, 50 um, 60 um, 70 um, 80 um, 90 um, 100 um, 120 um, 140 um, 160 um, 180 um, 200 um, 250 um, 300 um, 500 um, 1 mm, 2 mm, 5 mm, 10 mm, 20 mm, 50 mm, or 100 mm. The third dimension can be referred to as the length of the channel.

A microfluidic channel can comprise microstructures. For example, microstructures can be etched into the surface with overall dimensions of 2.5 cm×7.5 cm. A rim of 2 mm can be left around the substrate for bonding to the bottom surface to create a closed chamber. For example, engraved rectangular microstructures can have a width of from 250 μm to a length of 1000 μm with a variable height (e.g., 50, 80 and 100 μm). Microstructures can be arranged in a zig-zigged or staggered patterns with the number of features in row 1 to 5 being a, 2, 3, 2 and 1 with a spacing of 250 μm in between. Adjacent feature many be spaced at 200 μm. This staggered pattern can be repeated through the entire length of the channel and 1 to 4 of more rows of these features can run in parallel throughout the length of the channel cavity. The height, width, or length of the microstructures can be at least 5, 10, 25, 50, 75, 100, 250, 500 micrometers or more. The height, width, or length of the microstructures can be at most 100, 500, 250, 100, 75, 50, 25, or 10 or less micrometers. The spacing between microstructures can be at least 10, 25, 50, 75, 100, 250, 500, or 750 or more micrometers. The spacing between the microstructures can be at most 1000, 750, 500, 250, 100, 75, 50, or 25 or less micrometers.

The microstructures can be oriented in a herringbone pattern. A herringbone pattern can be created by forming a column of herringbones in which each microstructure is positioned adjacent to another microstructure. All microstructures in the column can face the same direction. In some embodiments, a distance between each microstructure is 50 micrometers. The microstructures can be positioned at any distance from each other. A column can include any number of microstructures. For example, a column can comprise at least about 1, 2, 3, 4, 5, 6, 7, 8, 9 or 10 or more microstructures. A column can comprise at most about 1, 2, 3, 4, 5, 6, 7, 8, 9 or 10 or more microstructures. The herringbone pattern can further include multiple columns of microstructures formed serially from an inlet to the outlet. In some embodiments, two adjacent columns of microstructures can be separated by 100 micrometers. In other words, a first microstructure of the second column can be positioned 100 micrometers away from a last microstructure of the first column. This pattern can be repeated from an inlet of the channel to the outlet.

The surface (e.g., of the microfluidic channel) can create, or be part of a volume. The surfaces herein can generate a volume over which the a sample is flowed. Such volume can be at least about 1, 10, 20, 30, 40, 50, 60, 70, 80, 90, 100, 200 or more microliters. Alternatively, or in addition, the volume of the surface can be at most about 1, 10, 20, 30, 40, 50, 60, 70, 80, 90, 100, 200 or more microliters.

Adhesion of the particles of interest within the sample to the surface can be increased along the flat surface of each microstructure due to formation of a stagnation zone in the center of the flat surface, thereby providing a stagnant flow condition increasing residence time and/or increasing the efficiency of chemical interactions with the binding surface. In some embodiments, the surface can be an outer surface of a microstructure within the channel or a portion of the surface being oriented substantially perpendicular to a direction of fluid flow of the biological sample within the microfluidic channel. The microstructure can extend completely or partially across the microfluidic channel.

A microfluidic device can include a fluid flow channel providing fluid communication between an inlet and an outlet. The channel can include at least one surface configured to bind the particle of interest (e.g., functionalized with a binding moiety). The surface can be formed on one or more microstructures within the channel configured to capture the particle of interest in the sample. The channel can be included in combination with other components to provide a system for isolating analytes or particles of interest (e.g., cells) from a sample. The volume of the channel or the region having the binding moiety may be selected depending on the volume of the sample being employed. The volume of the channel can be larger than the size of the sample.

One or more surfaces (e.g., of the microfluidic channel) can be configured to direct fluid flow and/or particles of interest within a fluid passing through the microfluidic channel. For example, the surface of a channel can be rough or smooth. The channel can include a roughened surface. The channel can comprise a periodic amplitude and/or frequency that is of a size comparable with a desired analyte or particle of interest (e.g., cell). In some instances, the channel can be defined by a wall with an undulating or "saw-tooth"-shaped surface positioned opposite the base of one or more microstructures within the microfluidic channel. The saw-tooth shaped surface can have a height and frequency on the order of about 1-100 micrometers. The saw-tooth shaped surface can be positioned directly opposite one or more microstructures extending only partially across the surface. The channel dimensions can be selected to provide a desired rate of binding of the particle of interest to the surface of the microfluidic channel.

The rate and pressure of fluid flow (e.g., for sample flow, buffer clean up, etc) can be selected to provide a desired rate of binding to the surface. The fluid flow velocity can also be selected to provide a desired shear stress to particles of interest bound to the surface. At least two variables can be manipulated to control the shear stress applied to the channel: the cross sectional area of the chamber and the fluid pressure applied to the chamber. Other factors can be manipulated to control the amount of shear stress necessary to allow binding of desired particles of interest and to prevent binding of undesired particles, (e.g., the binding moiety employed and the density of the binding moiety in the channel). Pumps that produce suitable shear forces in combination with microfluidic channels can produce a unidirectional shear stress (i.e., there can be substantially no reversal of direction of flow, and/or substantially constant shear stress). Either unidirectional or substantially constant shear stress can be maintained during the time in which a sample is passed through a channel.

The surface (e.g., microfluidic channel) can be configured to maximize binding of the particle of interest to one or more surfaces within the channel, while permitting a desired rate of fluid flow through the channel. Increasing the surface area of the microstructures can increase the area for particle of interest binding while increasing the resistance to sample fluid flow through the channel from the inlet to the outlet.

Microfluidic devices as mentioned herein may efficiently isolate particles of interest (e.g., rare cells, CTCs, stem cells, etc). Release and recovery of rare cells may be an important factor in isolating the rare cells. For example, when using a gradient elution method, there may be a potential for disruption of the cell membrane, degradation of surface markers, and alteration of the phenotypic and functional information of the CTCs which may limit downstream analyses of cells. For example, when using a flow-induced cell detachment, the necessary shear stress (e.g., 50 to 200 dynes/cm2) to break the antibody-cell surface antigen bonds may alter gene expression and possibly lead to cell death.

Functionalized Surfaces

The surface (e.g., microfluidic channel) can be coated with a non-fouling composition. A non-fouling composition can be a composition that prevents fouling (e.g., prevents binding of non-specific particles such as serum protein, while retaining the ability to bind particles of interest). The non-fouling composition can act as a lubricating surface such that only low flow shear stress, or low flow rates, can be used in the methods of the disclosure. For a non-fouling composition, only low flow shear stress may be required to remove non-specific cells or unwanted components from the non-fouling layer. In some instances, non-fouling behavior may be related to surface hydration, flexibility, and fluidity of the non-fouling surfaces. The non-fouling composition may comprise binding moieties and/or linkers as further described herein.

The non-fouling composition can comprise a lipid layer, or a lipid conjugate. The lipid layer can comprise a lipid monolayer, a lipid bilayer, supported lipid bilayers (SLBs) or lipid multilayers, liposomes, polypeptides, polyelectrolyte multilayers (PEMs), polyvinyl alcohol, polyethylene glycol (PEG), hydrogel polymers, extracellular matrix proteins, carbohydrate, polymer brushes, zwitterionic materials, poly(carboxybetaine) (pCB), poly(sulfobetaine) (pSB), pDMAEMA, and small organic compounds, or any combination thereof. Exemplary lipids that can be used in a non-fouling can include, but are not limited to, 1,2-dioleoyl-sn-glycero-3-phosphoethanolamine-N-(cap biotinyl) (sodium salt) (b-PE), 1-Palmitoyl-2-oleoyl-sn-glycero-3-phosphocholine (POPC), diacylglycerols, phospholipids, glycolipids, sterols, phosphatidylcholine (PtdCho), phosphatidylethanolamine (PtdEtn), phosphatidylinositol (PtdIns), phosphatidylserine (PtdSer), and phosphosphingolipids.

A lipid layer may possess lateral mobility. A lipid layer may be bioinert. A lipid layer may effectively resist non-specific proteins adsorption and cells adhesion (e.g., due to lateral mobility and bioinertness). Lateral mobility may allow lipid and proteins to reorganize their distribution on the surface. Lateral mobility may allow for assembly of proteins and increase binding affinity and specificity of target cells (particles of interest).

The mobility of the lipid molecules on a liquid-solid interface may enable them to continuously exchange positions with each other. Due to the mobility of the lipid molecules, once particles of interest approach an antibody-modified lipid layer, the underlining fluidic lipid layer may allow migration of antibody molecules toward the particles of interest (e.g., due to active recruitment or diffusion). As a result, particles of interest may adhere more firmly on the surface. Conversely, when antibody-functionalized lipids are concentrated underneath particles of interest, the concentration of non-functionalized lipids away from the target cells may increase, leading to greater resistance to non-specific binding. Reduced non-specific binding by protein and blood cells may reduce steric hindrance created by non-specific binding events in a limited binding space.

The non-fouling compositions may aid in removal of non-specific particles by exerting a small force. A shear stress required to remove non-specific particles from a non-fouling composition may be much less than from a conventional antibody coated surface, and may be much lower than that normally experienced by cells in physiological state such as that observed in human blood vessels (e.g., ~15 dyne/cm2).

In some embodiments, the non-fouling composition may be a supported lipid bilayer (SLB). SLBs may comprise lipids such as, 1,2-dioleoyl-sn-glycero-3-phosphoethanolamine-N-(cap biotinyl) (sodium salt) (b-PE) and 1-Palmitoyi-2-oleoyl-sn-glycero-3-phosphocholine (POPC). SLBs may be protein resistant. For example, SLBs may be protein resistant due to presence of neutral and zwitterionic phosphatidylcholine head groups in a wide pH range. For example, SLBs may be protein resistant due to an aqueous thin film formed between the hydrophilic lipid head groups and the bulk solution.

The non-fouling composition can comprise polyethylene glycol (PEG). The PEG can comprise a molecular weight of at least about 50, 100, 200, 500, 700, 1000, 5000, 10000, 15000, 50000, 75000, 100000, 150000, 200000, or 250000 or more daltons. The PEG can comprise a molecular weight of at most about 50, 100, 200, 500, 700, 1000, 5000, 10000, 15000, 50000, 75000, 100000, 150000, 200000, or 250000 or more daltons. The PEG can comprise a molecular weight from 100 to 100,000 daltons.

The non-fouling composition can comprise polyelectrolyte multilayers (PEMs). A PEM can refer to a polymer comprising an electrolyte. Exemplary PEMs can include, but are not limited to, poly-L-lysine/poly-L-glutamic acid (PLL/PLGA), poly-L-lysine/poly-L-aspartic acid, poly(sodium styrene sulfonate) (PSS), polyacrylic acid (PAA), poly(ethacrylic acid) (PEA), or any combination thereof.

The non-fouling composition can comprise a polymer brush. A polymer brush can refer to a polymer that can be attached at one end to a surface. Exemplary polymer brushes can include ([2-(acryloyloxy)ethyl] trimethyl ammonium chloride, TMA)/(2-carboxy ethyl acrylate, CAA) copolymer.

The non-fouling composition can comprise lipids, PEGs, polyelectrolyte multilayers, or polymer brushes, or any combination thereof.

The non-fouling composition can comprise a thickness. The thickness of the non-fouling composition can be at least about 0.5, 1, 10, 25, 50, 75, 100, 200, 300, 400, 500, 600, 700, 800, 900, 1000, 2000, 5000, 10000, 25000, 50000, 100000, 200000, 300000, 500000, 750000, 1000000 or more nanometers. The thickness of the non-fouling composition can be at most about 0.5, 1, 10, 25, 50, 75, 100, 200, 300, 400, 500, 600, 700, 800, 900, 1000, 2000, 5000, 10000, 25000, 50000, 100000, 200000, 300000, 500000, 750000, 1000000 or more nanometers.

A non-fouling composition can comprise a functional group. A functional group can be capable of covalent and/or non-covalent attachment either directly to a functional group present in the binding moiety, or directly to a functional group that is part of the linkage composition. Exemplary functional groups can include, but are not limited to hydroxy groups, amine groups, carboxylic acid or ester groups, thioester groups, aldehyde groups, epoxy or oxirane groups, hyrdrazine groups and thiol groups, biotin, avidin, streptavidin, DNA, RNA, ligand, receptor, antigen, antibody and positive-negative charges. A functional group can be attached to a lipid of the non-fouling composition. A function group may be selected to be reactive with functional groups present in either the linker or binding moiety. A functional group may be selected to bind to a second member of a binding pair which is present in either the linker or binding moiety. In some embodiments, the non-fouling composition may be a supported lipid bilayer (SLB) that inherently creates a lubricating layer rejecting non-specific blood components and assists a binding moiety's mobility to form a cell capture platform.

The non-fouling composition can be covalently attached to the surface. The non-fouling composition can be non-covalently attached to the surface. The non-fouling composition can interact with the surface by hydrogen bonding, electrostatic interactions, hydrophilic-hydrophilic interaction, polar-polar interaction, complimentary DNA binding, magnetic force, van der waals interactions, ionic interactions, and the like.

The non-fouling composition can bind a particle of interest while reducing the binding of other non-specific particles. The non-fouling composition can bind less than 1, 5, 10, 15, 20, 25, 30, 35, 40, 45, or 50% or more non-specific particles.

The surface may comprise a fouling composition. A fouling composition may comprise a composition that induces the aggregation and/or precipitation of non-specific particles of interest.

The surface may be a functionalized surface. The surface may be functionalized with, for example, dyes, organic photoreceptors, antigens, antibodies, polymers, poly-D-lysine, an oxide chosen among $HfO_2$, $TiO_2$, $Ta_2O_5$, $ZrO_2$ and their mixtures, organic compounds, and functionalized nanolayers. A surface can be functionalized with non-specific binding moiety such as an extracellular matrix, and a thin-film coating. A surface may be functionalized by, for example, soft-lithography, UV irradiation, and ink-jet printing.

In some embodiments, the non-fouling composition may comprise silane-functionalized PEG and the surface may be selected from the group consisting of silicon, glass, hydroxylated poly(methyl methacrylate) (PMMA), aluminum oxide, Ti02 and the like. In some embodiments, the non-fouling composition may comprise thiol-functionalized compounds and the surface may be selected from the group consisting of Au, Ag, Pt, and the like.

Binding Moieties

The surface can be coated with binding moieties selected to bind a particle of interest. The binding moiety can be conjugated to the surface. The binding moiety can be conjugated to the non-fouling composition (e.g., a lipid in the non-fouling composition).

A binding moiety can comprise a moiety that can specifically bind a particle of interest. For example, the binding moiety may selectively bind to one or more cells such as as epithelial or neoplastic cells associated with acute lymphoblastic leukemia, acute or chronic lymphocytic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic corneal nerve tumor, in situ carcinoma, intestinal ganglioneuroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor. Exemplary binding moieties can include peptides, polypeptides, synthetic polymers, molecular imprinted polymers, extracellular matrix proteins, binding receptors, antibodies, DNA, RNA, antigens, aptamers, or any other surface markers which present high affinity to the biological substance.

The binding moiety can bind to the particle of interest through, for example, molecular recognition, chemical affinity, and/or geometrical/shape recognition.

The binding moiety can comprise an antibody. The antibody can comprise antibodies against various epithelial markers, surface adhesion molecules, and growth factor receptors. The antibody can be an anti-EpCAM membrane protein antibody. The anti-EpCAM membrane protein antibody may be a EpAb4-1antibody, comprising a heavy chain sequence with SEQ ID No:1 and a light chain sequence with SEQ ID NO: 2 shown in Table 1. In some instances, the antibody can be anti-EGFR, anti-MUC-1, anti-C-MET, anti-HER-2, anti-EphB4, anti-CEA, or anti-ErbB2. Antibodies as used herein may bind specific cell markers, or cell surface antigens. Markers may comprise EpCAM, EGFR, MUC-1, C-MET, HER-2, EphB4, CEA, or ErbB2. In some instances, two or more different types of antibodies may be conjugated to a surface and/or the non-fouling composition. For example, the surface may be coated with both anti-EpCAM and anti-HER2.

TABLE 1

Amino Acid Sequence of VH and VL domains of EpAb4-1 antibody.

| | FW1 | CDR1 | FW2 | CDR2 |
|---|---|---|---|---|
| SEQ ID NO: 1 (VH) | QIQLVQSGPELKK PGETV KISCKAS | GYTFTNYG MN | WVKQAPGKGLK WMGW | INTYTGEP |
| SEQ ID NO: 2 (VL) | DIVMTQAAFSNPV TLGTS ASISC | RSSKSLLH SNGITYLY | WYLQKPGQSPQ LLIY | HMSNLAS |

TABLE 1 -continued

Amino Acid Sequence of VH and VL domains of EpAb4-1 antibody.

| | FW3 | CDR3 | FW4 | Family |
|---|---|---|---|---|
| SEQ ID NO: 1 (VH) | TYGDDFKGRFAFS LETSA STAYLQINNLKNE DTAT | FGRSVDF | WGQGTSVTVSS | VH9 |
| SEQ ID NO: 2 (VL) | GVPDRFSSSGSGT DFTLRI SRVEAEDVGIYYC | AQNLENPR T | FGGGTKLEIK | VK24/25 |

Complementary-determining regions 1-3 (CDR1-3), framework regions 1-4 (FW1-4) for both the VH and VL domains are shown.

The binding moiety can comprise a functional group. The functional group can be used to attach the binding moiety to the non-fouling composition and/or the surface. The functional group can be used for covalent or non-covalent attachment of the binding moiety. Exemplary functional groups can include, but are not limited to: hydroxy groups, amine groups, carboxylic acid or ester groups, thioester groups, aldehyde groups, epoxy or oxirane groups, hyrdrazine groups, thiol groups, biotin, avidin, streptavidin, DNA, RNA, ligand, receptor, antigen-antibody and positive-negative charges.

In some embodiments, functional groups comprise biotin and streptavidin or their derivatives. In some embodiments, functional groups comprise 1-Ethyl-3-[3-dimethylaminopropyl] carbodiimide hydrochloride (EDC) and N-hydroxysulfosuccinimide (Sulfo-NHS). In some embodiments, the functional groups comprise sulfo Succinimidyl-4-(N-maleimidomethyl) cyclohexane-1-carboxylate (sulfo-SMCC).

In some embodiments, the microfluidic surface comprises a non-fouling composition comprising a lipid non-covalently bound to the surface, and the non-fouling composition is attached to a binding moiety by a linker.

In some embodiments, a layer of an antibody for epithelial cell adhesion molecules (anti-EpCAM), clone EpAb4-1, may be conjugated to SLBs to selectively bind particles of interest such as CTCs. Lateral fluidity of SLBs may enable the clustering of proteins and enhancing the binding affinity and specificity to the particles of interest (e.g., CTCs). Additionally, the zwitterionic nature of the lipid molecules in the SLB may minimize non-specific protein and/or cell adsorption, thereby reducing fouling of the surface by peripheral blood.

Linkers

A linker can join the non-fouling composition and the binding moiety. Linkers can join the binding moiety to the surface. Linkers can join the non-fouling composition to the surface. A linker can join the non-fouling composition and the binding moiety covalently and/or non-covalently. A linkage between the two compositions may be formed by an interaction comprising electrostatic interaction, hydrophilic-hydrophilic interaction, polar-polar interaction, complementary DNA binding, magnetic force, or combinations thereof.

Exemplary linkers can include, but are not limited to: metals, plastics, glass, silicon wafers, hydroxylated poly (methy3 methacrylate) (PMMA), hydroxy groups, amine groups, carboxylic acid or ester groups, thioester groups, aldehyde groups, epoxy or oxirane groups, hyrdrazine groups thiol groups, biotin, avidin, streptavidin, DNA, RNA, ligand, receptor, antigen, antibody, and positive-negative charges, or any combination thereof. For example, the linkers may include silane, aminopropyltrietlioxy silane, aminopropyitrimethoxy silane, silane-PEG-NH2, silane-PEG-N3 (PEG molecular weight is about 1,000 to about 30,000 daltons) and silane-PEG biotin. In some embodiments, complementary DNA fragments may be used for binding the non-fouling composition and the binding moiety. The fragments are attached to each of the compositions and can be partially or completely complementary over their lengths. A suitable length of DNA will generally be at least 15, 20, 25, 35, 50, 100 or more bases in length. An example of the DNA used in the present invention is a DNA tweezer.

The linker can comprise a cleavable linker. Exemplary cleavable linkers can include, but are not limited to: a photosensitive functional group cleavable by ultraviolet irradiation, an electrosensitive functional group cleavable by electro pulse mechanism, an iron or magnetic material cleavable by the absence of the magnetic force, a polyelectrolyte material cleavable
by breaking the electrostatic interaction, a DNA cleavable by hybridization, a thermal dissociable group, and the like. For example, prior to release, an irradiation, heating, magnetic force, electric force, and the like could be applied to a surface containing cleavable linkers. Subsequently, particles of interest may be eluted (e.g., using a shear of air foam).

Particles of Interest, Samples, and Subjects

The disclosure provides for capturing particles of interest. A particle of interest can be a cell. A cell can refer to a eukaryotic cell. A eukaryotic cell can be derived from a rat, cow, pig, dog, cat, mouse, human, primate, guinea pig, or hamster (e.g., CHO cell, BHK cell, NSO cell, SP2/0 cell, HEK cell). A cell can be a cell from a tissue, a hybridoma cell, a yeast cell, a virus (e.g., influenza, coronaviruses), and/or an insect cell. A cell can be a cell derived from a transgenic animal or cultured tissue. A cell can be a prokaryotic cell. A prokaryotic cell can be a bacterium, a fungus, a metazoan, or an archea. A cell can refer to a plurality of cells or any cell referred to herein.

A particle of interest can refer to a part of a cell. For example, a cell can refer to a cell organelle (e.g., golgi complex, endoplasmic reticulum, nuclei), a cell debris (e.g., a cell wall, a peptidoglycan layer), and/or a the contents of a cell (e.g., nucleic acid contents, cytoplasmic contents).

A particle of interest can be a rare cell. Exemplary cells can include but are not limited to: rare cancer cells, circulating tumor cells, circulating tumor microemboli, blood cells, endothelial cells, endoderm-derived cells, ectoderm-derived cells, and meso-derm derived cells, or any combination thereof.

A particle of interest can be part of a sample. A sample can comprise a plurality of particles, only some of which are particles of interests. A particle can refer to a cell, a nucleic acid, a protein, a cellular structure, a tissue, an organ, a cellular break-down product, and the like. A particle can be a fouling particle. A particle may not bind to a non-fouling composition. A sample can comprise at least about 0.1, 0.2, 0.3, 0.4, 0.5, 0.6, 0.7, 0.8, 0.9, 1, 2, 3, 4, 5, 6, 7, 8, 9, or 10% or more particles of interest. A sample can comprise at most about 0.1, 0.2, 0.3, 0.4, 0.5, 0.6, 0.7, 0.8, 0.9, 1, 2, 3, 4, 5, 6, 7, 8, 9, or 10% or more particles of interest.

A sample can be obtained from a subject. A subject can be a human. A subject can be a non-human. A subject can be, for example, a mammal (e.g., dog, cat, cow, horse, primate, mouse, rat, sheep). A subject can be a vertebrate or invertebrate. A subject can have a cancer disease. A subject can have a disease of rare cells. A subject may have a disease of rare cells, or cancer, and not show symptoms of the disease. The subject may not know they have cancer or a disease of rare cells.

A sample can comprise a bodily fluid. Exemplary bodily fluids can include, but are not limited to, blood, serum, plasma, nasal swab or nasopharyngeal wash, saliva, urine, gastric fluid, spinal fluid, tears, stool, mucus, sweat, earwax, oil, glandular secretion, cerebral spinal fluid, tissue, semen, vaginal fluid, interstitial fluids, including interstitial fluids derived from tumor tissue, ocular fluids, spinal fluid, throat swab, breath, hair, finger nails, skin, biopsy, placental fluid, amniotic fluid, cord blood, emphatic fluids, cavity fluids, sputum, pus, micropiota, meconium, breast milk and/or other excretions.

Foam Composition

The non-fouling layer on the surface may provide further advantages to the devices herein. For example, the non-fouling layer may allow for the gentle release of captured particles, such as cells, without substantially affecting their viability. Specifically, the present disclosure contemplates the use of a gentle liquid solution or a foam composition such as an air form composition to release cells captured on the surfaces described herein.

A foam composition may release captured particles via surface tension. For example, when an air bubble (e.g., within a foam composition) contacts the captured particles, an air-liquid interface on the particle surface may form, giving rise to a net force perpendicular to the surface and pulling the captured particle up, leading to release. For particles of interest captured on non-fouling compositions (e.g., lipid layers), forces other than surface tension may contribute to the release of particles of interest, alternatively or in addition to the surface tension. For example, the forces contributing to release of particles of interest may be hydrophobic-hydrophilic, hydrophobic-hydrophobic, and/or hydrophilic-hydrophilic interactions. For example, for a lipid layer, contact with an air bubble may pull hydrophobic heads of the lipid layer into the air phase of the bubble while the hydrophilic tail of the lipid layer is pulled into the liquid phase and the captured particles may be released along with the lipid layer pulled along the air bubble. The forces in addition or alternative to surface tension may be of smaller quantity or of different quality such that the viability of the released cells is higher.

Figure 2:
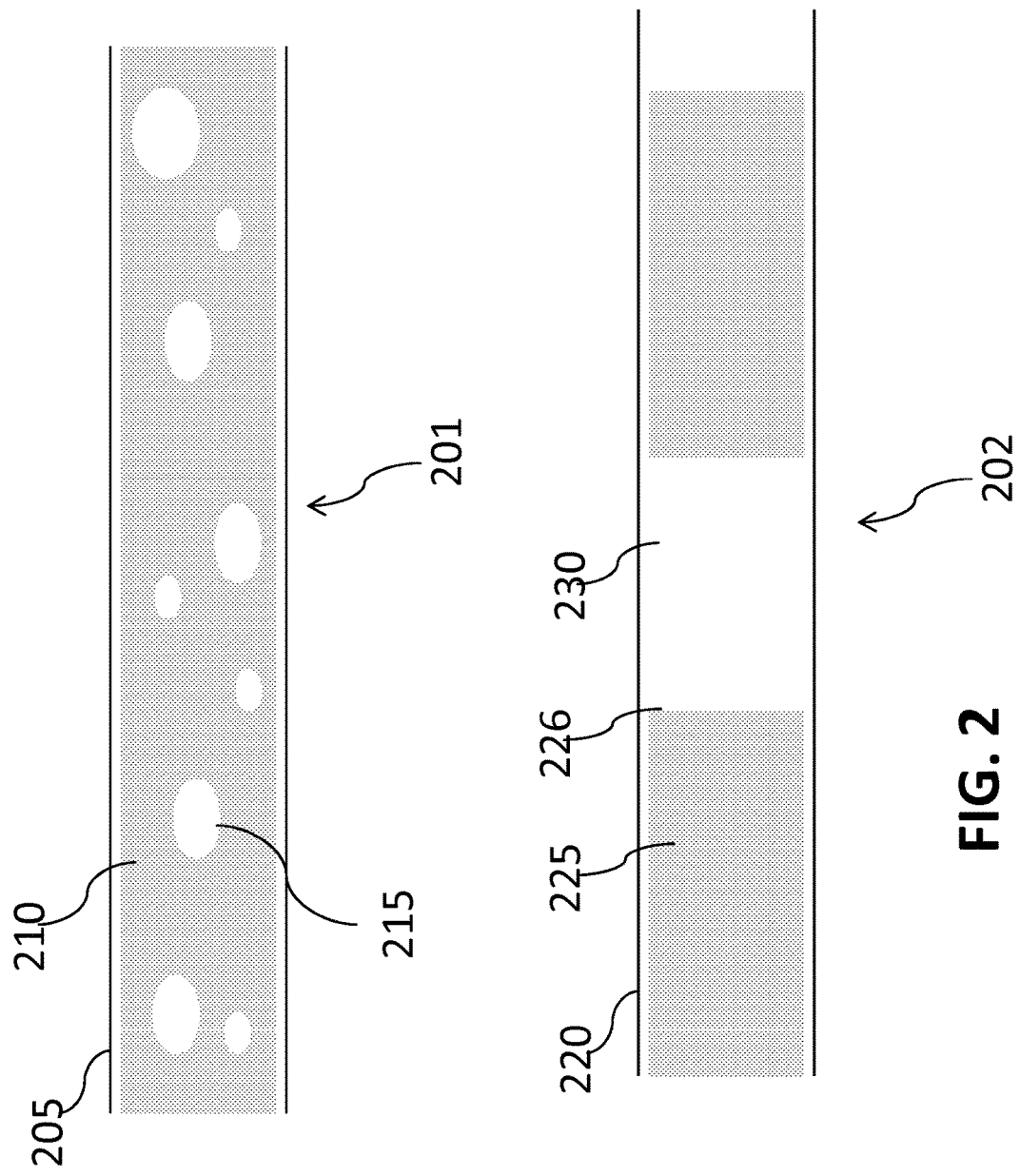
FIG. 2 illustrates an exemplary embodiment of the foam composition of the disclosure and an air-liquid interface.

A foam composition of the disclosure can comprise liquid and air. The liquid and air can be combined to form air bubbles, thereby making foam. The foam composition can be a liquid with pockets of air. The foam composition can be a continuous stream of liquid with pockets of air. For example, a foam composition can comprise an air bubble surrounded by liquid. The foam composition can be a continuous sequence of air bubbles. In some instances, a foam composition may not refer to an air bubble followed by a liquid. An exemplary embodiment of the foam composition of the disclosure is depicted in FIG. 2. In some embodiments, as depicted in 201, a foam composition can be inside a channel 205, which may comprise a surface. The foam composition can comprise a continuous liquid interface 210 which can be interspersed with air bubbles 215. A foam composition can differ from an air-liquid interface as depicted in 202. The air-liquid interface 226 can occur when a section of air 230 is bookended by a liquid 225 in a channel 220 (e.g., wherein the liquid completely consumes the volume between the sections of air). In some instances, the air 230 of the air-liquid interface 226 may be unable to compress when flowed through a channel 220 and may become trapped in the channel 220 (e.g., when the volume decreases along the channel, or there are obstructions within the channel). In some instances, the air 215 of the foam composition of 201 is of a size that may not become trapped in the channel 205. In some instances, the diameter of the air bubbles 215 of the foam composition of 201 is smaller than the cross-sectional dimension of channel (e.g., microfluidic channel 205). In some instances, the diameter of the air bubble 230 of the air-liquid interface 226 may be about the same size as the cross-sectional dimension of the channel (e.g., cross-sectional dimension of the channel).

The air of the foam composition can comprise any gas. For example, air can refer to oxygen, nitrogen, carbon dioxide, hydrogen, argon, and helium. Air can be pressurized air.

The liquid of the foam composition can be isotonic. The liquid of the foam composition may not be isotonic. The liquid of the foam composition can comprise a protein. The liquid of the foam composition can comprise any isotonic protein-containing liquid. The liquid of the foam composition can be a liquid that is compatible with cell culture (e.g., cell culture media, Dulbecco's modified eagle medium (DMEM), Roswell Park Memorial Institute (RPMI), MEM, CMRL, Brinster's BMOC-3, Glasgow, Leibovitz's L-15). The liquid can comprise bovine serum albumin (BSA). Non-limiting examples of proteins can include, fetal bovine serum (FBS), new calf serum (NCS), amino acids (e.g., L-glutamine), albumin, transferrin, fibronectin, aprotinin, casein, and fetuin, or any combination thereof. In some instances, protein and/or serum may coat a surface of air bubbles of the foam composition. In some instances, protein and/or serum may counteract effects of surface tension and stabilize bubbles by preventing outward diffusion of air (e.g., by coating the surface of air bubbles). For example, the liquid may be DMEM supplemented with 10% FBS and RPMI supplemented with 10% FBS. For example, the liquid may be a solution of FBS (e.g., 5%) in PBS.

The liquid can comprise a protein having a concentration of at least 1, 2, 3, 4, 5, 6, 7, 8, 9, 10, 20, 30, or 40% concentration. The liquid can comprise a protein having a concentration of at most 1, 2, 3, 4, 5, 6, 7, 8, 9, 10, 20, 30, or 40% concentration. The liquid can comprise a protein at 5% concentration. The liquid can comprise BSA at 5% concentration in phosphate buffered saline.

The liquid can comprise a protein and a buffer. Exemplary buffers can include phosphate buffered saline (PBS), ammonium sulfate, Bicine, imidazole buffer, hepes, mops, mes, potassium citrate, potassium formate, tris, sodium phosphate dibasic, and sodium phosphate monobasic. In some instances, the liquid comprises phosphate buffered saline.

The protein used in the liquid can be a hydrophobic protein. The temperature of the liquid can be raised to help dissolve the hydrophobic protein in the liquid solution. The temperature of the liquid can be raised to 4 C, 25 C, or 37 C or higher.

The liquid can comprise an amphiphilic polymer. An amphiphilic polymer can refer to a biological molecule (e.g., amino acid polymer) that has both hydrophobic and hydrophilic regions. Hydrophobic and hydrophilic regions of the amphipathic molecule can be involved in electrostatic, polar-polar, and polar-nonpolar interactions. When an amphipatic polymer is agitated with air, the polymer can reorient into micelle-like structures in the aqueous phase. The reorientation of the amphipathic polymer can refer to reorienting the amphipathic polymer such that the majority of polymers are facing the same direction (e.g., the hydrophobic region facing towards the inner core of the micelle, and the hydrophilic region facing towards the aqueous solution). For example, a micelle-like structure can comprise an inner core comprising an air bubble, and an outer core comprising the amphipathic polymer. Exemplary amphipathic molecules can include, but are not limited to, phospholipids, cholesterol, glycolipids, fatty acids, bile acids, saponins, surfactants, detergents, polyethylene glycols, glycerols, and zwitterions.

The liquid can comprise a carbohydrate (e.g., a starch). Exemplary carbohydrates can include monosaccharides, disaccharides, polysaccharides, glucose, mannose, sucrose, cellulose, glyceraldehydes, nucleic acid, DNA, RNA, lactose, and galactose.

The liquid can comprise an emulsion. An emulsion can refer to a mixture of two immiscible liquids. Exemplary emulsions can include water-in-oil emulsions, oil-in-water emulsions, water-in-water emulsions, microemulsions, and nanoemulsions. An emulsion can comprise an emulsifier. Exemplary emulsifiers can include a detergent (e.g., Tween-20, Triton-X), a surfactant (e.g., SDS), and lecithin. In some embodiments, the liquid of the foam composition can comprise any combination of a protein, a carbohydrate, an emulsion, or a polymer.

The liquid may be viscous. The viscosity of the liquid can be at least 20, 30, 40, 50, 60, 70, 80, 90, or 100% greater than the viscosity of water. The viscosity of the liquid can be at most 20, 30, 40, 50, 60, 70, 80, 90, or 100% greater than the viscosity of water. The viscosity of the liquid can be at least 20, 30, 40, 50, 60, 70, 80, 90, or 100% less than the viscosity of water. The viscosity of the liquid can be at most 20, 30, 40, 50, 60, 70, 80, 90, or 100% less than the viscosity of water. The viscosity of the liquid may be such that it maintains the foam composition for at least 1, 2, 5, 10, 15, 20, 25, 30, 35, 40, 45, 50, or 60 minutes.

In some embodiments, the foam composition comprises molecules that balance the strength and weakness of the foam. For example, the foam composition may be able to be malleable enough to move through a channel, such that the shape of the foam bubbles may be temporarily deformed (e.g., a microfluidic channel, e.g., comprising microstructures), yet strong enough to carry the released cells such that the foam bubbles do not pop prematurely.

The volume of liquid to be used to generate the foam composition of the disclosure can be at least 1, 2, 3, 4, 5, 6, 7, 8, 9, or 10 or more milliliters. The volume of liquid to be used to generate the foam composition of the disclosure can be at most 1, 2, 3, 4, 5, 6, 7, 8, 9, or 10 or more milliliters. In some instances, the volume of liquid to be used to generate the foam composition of the disclosure is 4 milliliters. In some instances, the liquid of the foam composition comprises 4 milliliters of a 5% BSA in PBS.

The volume of air to be used to generate the foam composition of the disclosure can be at least 1, 2, 3, 4, 5, 6, 7, 8, 9, or 10 or more milliliters. The volume of air to be used to generate the foam composition of the disclosure can be at most about 1, 2, 3, 4, 5, 6, 7, 8, 9, or 10 or more milliliters. In some instances, the volume of air to be used to generate the foam composition of the disclosure is 2 milliliters.

The liquid and air can be combined in different amounts. For example, the ratio of liquid to air can be at least 0.5:1, 1:1, 1.5:1, 2:1, 3:1, 4:1 or 5:1 or more. The ratio of liquid to air can be at most 0.5:1, 1:1, 1.5:1, 2:1, 3:1, 4:1 or 5:1 or more. In some instances, the ratio of liquid to air is 2:1. The amount of liquid can be at least 50, 75, 100, 125, 150, 175, 200, 225, 250, 275, 300, 325, 350, 375, or 400% or more the amount of air. The amount of liquid can be at most 50, 75, 100, 125, 150, 175, 200, 225, 250, 275, 300, 325, 350, 375, or 400% or more the amount of air. In some instances, the foam composition comprises a mixture of 4 milliliters of a 5% BSA in PBS and 2 mL of air.

The foam composition can comprise air bubbles. The air bubbles of the foam composition can be at least 1, 5, 10, 20, 30, 40, 50, 60, 70, 80, 90, 100, 110, 120, 130, 140, 150, 160, 170, 180, 190, 200, 300, 400, 500, 600, 700, 800, or 900 micrometers or more in diameter. The air bubbles of the foam composition can be at most 1, 5, 10, 20, 30, 40, 50, 60, 70, 80, 90, 100, 110, 120, 130, 140, 150, 160, 170, 180, 190, 200, 300, 400, 500, 600, 700, 800, or 900 micrometers or more in diameter. In some instances, the air bubbles of the foam composition comprise a diameter from 20 micrometers to 500 micrometers. In some instances, the air bubbles of the foam composition comprise a diameter of 60 micrometers. In some instances, the foam composition comprises a mixture of 4 milliliters of a 5% BSA in PBS, 2 mL of air, and comprises air bubbles from about 10 to 100 micrometers.

The air bubbles of the foam composition can be of a size smaller than the cross-sectional dimension of a microfluidic channel. The air bubbles of the foam composition can be of a size larger than the cross-sectional dimension of a microfluidic channel. For example, the air bubbles of the foam composition may compress within a microfluidic channel and pass through. The air bubbles of the foam composition can be of a size larger than the height of a non-fouling composition. The ratio of the diameter of the air bubble to the cross sectional length (e.g., diagonal length, width, or height) of the microfluidic channel may be about $1/100$, $1/50$, $1/25$, $1/18$, $1/16$, $1/12$, $1/8$, $1/5$, $1/4$, $1/2$, $2/3$, 1, 1.2, 1.5, 2, 3, 4, 5, or 10. The diameter of the air bubble and the cross sectional length of the microfluidic channel may be as previously described herein. In some embodiments, the foam composition may comprise air bubbles whose diameter is smaller than the cross sectional length (e.g., diagonal length, width, or height) of the microfluidic channel. In some embodiments, the foam composition may comprise at least some air bubbles whose diameter is smaller than the cross sectional length (e.g., diagonal length, width, or height) of the microfluidic channel. In some embodiments, the foam composition may comprise air bubbles, a majority of which has a diameter smaller than a cross sectional length (e.g., diagonal length, width, or height) of the microfluidic channel. As used herein a majority may refer to at least 20%, 30%, 40%, 50%, 60%, 70%, 80%, or 90%. As used herein, a width of the microfluidic channel may refer to a width of the surface (e.g., microfluidic surface). For example, the foam composition may comprise air bubbles with a diameter between 0 and 200 um while a width of the microfluidic channel is larger than 200 um. For example, the foam composition may comprise at least 50% of air bubbles having a diameter between 1 um and 200 um while a width of the microfluidic channel is larger than 200 um.

The percentage of air bubbles comprising a diameter from 1 micrometer to 200 micrometers can be at least 20, 30, 40, 50, 60, 70, 80, 90, or 100%. The percentage of air bubbles comprising a diameter from 1 micrometer to 100 micrometers can be at least 20, 30, 40, 50, 60, 70, 80, 90, or 100%. The percentage of air bubbles comprising a diameter from 1 micrometer to 200 micrometers can be at most 20, 30, 40, 50, 60, 70, 80, 90, or 100%. The percentage of air bubbles comprising a diameter from 1 micrometer to 100 micrometers can be at most 20, 30, 40, 50, 60, 70, 80, 90, or 100%. The percentage of air bubbles comprising a diameter from 10 micrometers to 100 micrometers can be at least 50, 60, 70, 80, 90, or 100%. The percentage of air bubbles comprising a diameter from 10 micrometers to 100 micrometers can be at most 50, 60, 70, 80, 90, or 100%. In some instances, the foam composition comprises a mixture of 4 milliliters of a 5% BSA in PBS, 2 mL of air, and/or at least 50% of the air bubbles of the foam composition have a diameter from about 10 to 100 micrometers.

The volume of the foam composition can be at least 1-fold, 2-fold, 3-fold, 4-fold, or 5-fold or more the volume of the channel that the foam composition will be flowed over. The volume of the foam composition can be at least 50, 100, 150, 200, 250, 300, 350, 400, 450, 500, 550, 600, 650, 700, 750, 800, 850, 900, 950 or 1000% or more than the volume of the channel that the foam composition will be flowed over. The ratio of the volume of the foam composition to the volume of the channel that the foam composition will be flowed over can be at least 1:1, 2:1, 3:1, 4:1, 5:1, 6:1, 7:1, 8:1, 9:1, or 10:1 or more. In some instances, the foam composition comprises a mixture of 4 milliliters of a 5% BSA in PBS, 2 mL of air, at least 50% of the air bubbles of the foam composition have a diameter from about 10 to 100 micrometers, and/or the volume of the foam composition is at least 5-fold more than the volume of the channel that the foam composition will be flowed over.

The volume of the foam composition that is liquid can vary. For example, the volume of the foam composition can comprise at least 30, 40, 50, 60, 70, 80, 90 or 100% liquid. The volume of the foam composition can comprise at most 30, 40, 50, 60, 70, 80, 90 or 100% liquid.

The volume of the foam composition can comprise varying amounts of liquid and air. For example, the volume of the foam composition can comprise at least 2-fold, 3-fold, 4-fold, 5-fold, 10-fold, 20-fold, 50-fold, or 100-fold or more liquid than air. The volume of the foam composition can comprise at most 2-fold, 3-fold, 4-fold, 5-fold, 10-fold, 20-fold, 50-fold, or 100-fold or more liquid than air. The volume of the foam composition can comprise at least 2-fold, 3-fold, 4-fold, 5-fold, 10-fold, 20-fold, 50-fold, or 100-fold or more air than liquid. The volume of the foam composition can comprise at most 2-fold, 3-fold, 4-fold, 5-fold, 10-fold, 20-fold, 50-fold, or 100-fold or more air than liquid.

The volume of the foam composition can be at least 0.5, 1, 2, 3, 4, 5, 6, 7, 8, 9, or 10 or more milliliters. The volume of the foam composition can be at most 0.5, 1, 2, 3, 4, 5, 6, 7, 8, 9, or 10 or more milliliters. In some instances, the foam volume is 2 milliliters. In some instances, the foam volume to be used in the methods of the disclosure is 1.5 milliliters. In some instances, the foam composition comprises a mixture of 4 milliliters of a 5% BSA in PBS, 2 mL of air, at least 50% of the air bubbles of the foam composition have a diameter from about 10 to 100 micrometers, and/or the volume of the foam composition is at least 1.5 milliliters.

The volume of the foam composition (e.g., amount) can be substantially equal to the volume of the channel over which the foam will be flowed. The volume of the foam composition can be at least 5, 10, 15, 20, 25, 30, 35, 40, 45, 50, 55, 60, 65 or 70-fold or more of the volume of the channel over which the foam will be flowed. The volume of the foam composition can be at most 5, 10, 15, 20, 25, 30, 35, 40, 45, 50, 55, 60, 65 or 70-fold or more of the volume of the channel over which the foam will be flowed. In some instances, the volume of the foam composition is 35 fold more than the volume of the channel over which the foam will be flowed. In some instances, the volume of foam composition to be flowed is 1.5 milliliters, and the volume of the channel is 55 microliters.

The foam composition can be active for use in the methods of the disclosure for at least 1, 5, 10, 15, 20, 25, 30, 35, or 40 or minutes after making the foam. The foam composition can be active for use in the methods of the disclosure for at most 1, 5, 10, 15, 20, 25, 30, 35, or 40 or minutes after making the foam. The foam composition can be active for use 15 minutes after making the foam. In some instances, bubbles may coalesce, break or decrease in size over time, thereby reducing effectiveness of the foam composition. In some instances, the foam composition comprises a mixture of 4 milliliters of a 5% BSA in PBS, 2 mL of air, at least 50% of the air bubbles of the foam composition have a diameter from about 10 to 100 micrometers, the volume of the foam composition is at least 1.5 milliliters, and/or the foam composition can be active for 15 minutes.

The foam composition can be reusable. The foam composition can be reused at least 1, 2, 3, 4 or 5 times. The foam composition can be reused at most 1, 2, 3, 4 or 5 times. The foam composition may not be reusable. The foam composition may be newly prepared for each use.

The foam composition of the disclosure can be less dense than the liquid used to make the foam composition. The foam composition can be 10, 20, 30, 40, or 50% or more, less dense than the liquid used to make the foam composition. The foam composition can comprise a different material phase than the liquid. For example, the foam composition can comprise a gaseous phase (e.g., bubbles). A foam composition can be 50, 150, 200, 250, 300, 350, 400, 450, 500, 550, 600, 650, 700, 750, 800, 850, 900, 950% or more gaseous than a liquid used to make the foam composition.

A foam composition can be viscous. The viscosity of the foam composition can be at least 20, 30, 40, 50, 60, 70, 80, 90, or 100% greater than the viscosity of water. The viscosity of the foam composition can be at most 20, 30, 40, 50, 60, 70, 80, 90, or 100% greater than the viscosity of water. The viscosity of the foam composition can be at least 20, 30, 40, 50, 60, 70, 80, 90, or 100% less than the viscosity of water. The viscosity of the foam composition can be at most 20, 30, 40, 50, 60, 70, 80, 90, or 100% less than the viscosity of water.

Methods of Making a Foam Composition

The foam composition of the disclosure can be prepared using, e.g., any one or more of the methods described herein. In some instances the foam is made at less than 0, 4, 15, 16, 17, 18, 19, 20, 21, 22, 23, 24, 25, 26, 27, 28, 29, or 30 degrees Celsius. The foam composition of the disclosure can be prepared at more than 0, 4, 15, 16, 17, 18, 19, 20, 21, 22, 23, 24, 25, 26, 27, 28, 29, or 30 degrees Celsius. The foam composition can be prepared at a temperature from 0-4 Celsius, 0-18 Celsius, 0-37 Celsius, 4-18 Celsius, 4-18 Celsius, 15-25 Celsius, 18-22 Celsius, 18-25 Celsius, 18-37 Celsius. In some instances, the foam composition of the disclosure is prepared at a temperature from 18-22 degrees Celsius.

In some instances, the foam composition comprises a mixture of 4 milliliters of a 5% BSA in PBS, 2 mL of air, at least 50% of the air bubbles of the foam composition have a diameter from about 10 to 100 micrometers, the volume of the foam composition is at least 1.5 milliliters, and/or the foam composition is prepared at a temperature from 18-22 degrees.

Vortexing

The disclosure provides for methods for making the foam composition of the disclosure. A method for making a foam composition can comprise combining a liquid of the disclosure and air and mixing the sample.

The mixing can be performed by, for example, vortexing, agitating, rocking, stirring, magnetic stirring, and shaking. The mixing (e.g., vortexing) can be performed for at least 5, 10, 15, 20, 25, 30, 35, 40, 45, 50, 55, or 60 or more seconds. The mixing (e.g., vortexing) can be performed for at most 5, 10, 15, 20, 25, 30, 35, 40, 45, 50, 55, or 60 or more seconds.

In some instances, the method of making a foam composition can comprises vortexing for 30 seconds a mixture comprising 4 milliliters of a 5% BSA in PBS, 2 mL of air, wherein the foam composition is prepared at a temperature from 18-22 degrees Syringe The foam composition of the disclosure can be made by transferring the liquid of the disclosure and air between containers through an intermediate valve. Exemplary containers can include, but are not limited to, syringes, tubes, bottles, glasses, and buckets. In some instances, the container is a syringe.

Transferring the liquid and air from one container (e.g., syringe) to another container (e.g., syringe) can comprise transferring the liquid and air through a hole in an intermediate valve. The hole can be useful for generating the air bubbles of the foam composition. The hole can be at least 0.01, 0.05, 0.1, 0.5, 1 or more millimeters in diameter. The hole can be at most 0.01, 0.1, 0.5, 1, 1.5, 2 or more millimeters in diameter. The hole can be 0.2 millimeters. The hole can be of a size that generates air bubbles between 1 and 200 micrometers in diameter. In some instances, the method of making foam composition can comprise transferring a mixture of 4 milliliters of a 5% BSA in PBS, 2 mL of air through a hole comprising a diameter of 0.2 millimeters and wherein at least 50% of the air bubbles of the foam composition have a diameter from about 10 to 100 micrometers.

In some instances, the smaller the opening of the hole, the higher the shear pressure during the transferring, thereby resulting in smaller bubbles. In some instances, the smaller the opening of the hole, the more external pressure to undergo the transferring may be needed. In some instances, the larger the hole, the larger the variation in the size of the bubbles.

The transferring between containers can be performed at least 1, 2, 3, 4, 5, 6, 7, 8, 9, 10, 11, 12, 13, 14, 15, 16, 17, 18, 19, or 20 or more times. The transferring between containers can be performed at most 1, 2, 3, 4, 5, 6, 7, 8, 9, 10, 11, 12, 13, 14, 15, 16, 17, 18, 19, or 20 or more times.

The transferring between containers can be performed for at least 1, 2, 3, 4, 5, 6, 7, 8, 9, or 10 or more seconds. The transferring between containers can be performed for at most 1, 2, 3, 4, 5, 6, 7, 8, 9, or 10 or more seconds. In some instances, the method of making foam composition can comprise transferring a mixture of 4 milliliters of a 5% BSA in PBS, 2 mL of air through a hole comprising a diameter of 2 millimeters at least 10 times, and wherein at least 50% of the air bubbles of the foam composition have a diameter from about 10 to 100 micrometers.

In some instances, the containers for transferring the liquid and air are syringes. The syringes can be the same size. The syringes can be different sizes. A syringe can be able to hold at least 1, 5, 10, 20, 25, or 50 or more milliliters. A syringe can be able to hold at most 1, 5, 10, 20, 25, or 50 or more milliliters. The syringes can comprise a connection port. The connection port can comprise a luer lock. A connection port can comprise a slip tip.

A syringe can be connected to another syringe by a valve. A valve can be a three way valve. The valve can connect to the luer lock of the syringe.

A first syringe can comprise both the liquid and air. In some instances, both the first and second syringes comprise the liquid and air. In some instances, a first syringe comprises the liquid and a second syringe comprises air.

In some instances, the first syringe comprises both the liquid and the air, and the second syringe is empty. The contents from the first syringe can be transferred to the second syringe by depressing the piston of the first syringe. The contents from the first syringe can be transferred to the second syringe by pulling on the piston of the second syringe, thereby drawing in the liquid from the first syringe.

The transferring can be performed at a pressure suited for generating the foam composition of the disclosure. For example, the pressure can be the pressure of an adult human thumb pushing on a barrel and/or piston of a syringe. The pressure used in the transferring can be at least 0.1, 0.2 0.3, 0.4, 0.5, 1, 1.5, 2, 2.5, 3, 3.5, 4, 4.5, 5, 5.5, 6, 6.5, 7, 7.5, 8, 8.5, 9, 9.5 or 10 or more mega pascals (MPa). The pressure used in the transferring can be at most 0.1, 0.2 0.3, 0.4, 0.5, 1, 1.5, 2, 2.5, 3, 3.5, 4, 4.5, 5, 5.5, 6, 6.5, 7, 7.5, 8, 8.5, 9, 9.5 or 10 or more mega pascals (MPa).

Membrane

The foam composition of the disclosure can be made with a membrane. A sample comprising a liquid of the disclosure and air can be drawn through a membrane. Exemplary membranes can include, but are not limited to, air stones, fine-pore membranes, rubber membrane diffusers, air disks, and air tubes. The liquid and air can be drawn through the membrane by a syringe.

The membrane can comprise pores. The pores can be at least 1, 5, 10, 20, 30, 40, 50, 60, 70, 80, 90 or 100 or more micrometers in diameter. The pores can be at most 1, 5, 10, 20, 30, 40, 50, 60, 70, 80, 90 or 100 or more micrometers in diameter. The pores can be of a size that generate air bubbles comprising a diameter from 1 to 200 micrometers. The pores can be of a size that generate air bubbles comprising a diameter from 10 to 100 micrometers. In some instances, the method of making foam composition can comprise drawing a mixture comprising 4 milliliters of a 5% BSA in PBS, 2 mL of air through a membrane comprising pores that are at least 5 microns in diameter, and wherein at least 50% of the air bubbles of the foam composition have a diameter from about 10 to 100 micrometers.

The pressure used to pull the liquid and air mixture through the membrane can be at least 0.1, 0.2, 0.3, 0.4, 0.5, 0.6, 0.7, 0.8, 0.9, or 1 or more $kg/cm^2$. The pressure used to pull the liquid and air mixture through the membrane can be at most 0.1, 0.2, 0.3, 0.4, 0.5, 0.6, 0.7, 0.8, 0.9, or 1 or more $kg/cm^2$.

Pumping

In some instances, a foam composition can be generated by a pumping mechanism. The pumping mechanism may only be performed once to generate the foam of the disclosure. The method can include pumping a liquid solution, wherein during the pumping the solution mixes with air. The mixed solution of liquid and air can be pumped through a nozzle. The nozzle can comprise a diameter of at most 0.001, 0.005, 0.01, 0.05, 0.1, 0.5, or 1 or more millimeters.

Capillary Microfluidics

Figure 3:
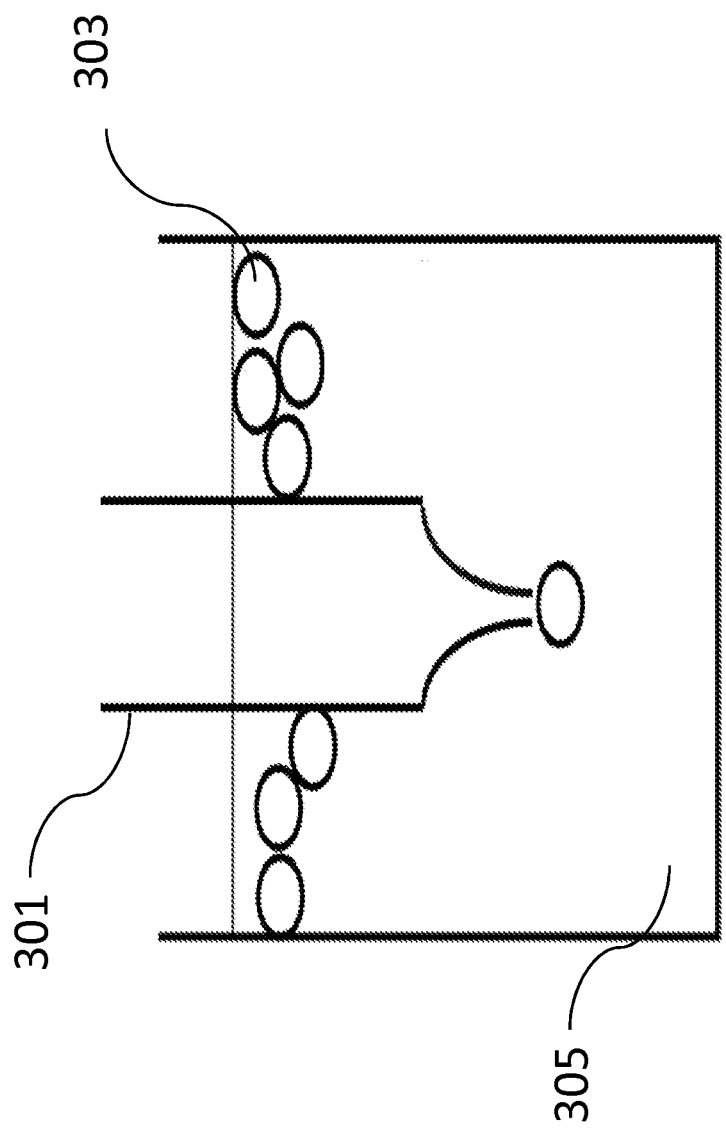
FIG. 3 illustrates a capillary microfluidic device.

In some instances, a foam composition can be generated by capillary microfluidic devices. FIG. 3 illustrates a capillary microfluidic device, in accordance with embodiments. For example, a circular glass capillary 301 may be heated and pulled to form a tapered geometry in one end orifice. A current of air may be flown through the tapered orifice into a tank of liquid 303 (e.g., culture medium) to form air bubbles 305 and a foam composition. The volume of air bubbles may be controlled by adjusting a flow rate of the air current. For example, when the flow rate of the air current is low, monodisperse air drops may be created. For example, when the flow rate of the air current is beyond a certain threshold, an air jet may be formed and air drops may be formed downstream.

Methods

The disclosure provides for methods for capturing and releasing a particle of interest (e.g., circulating tumor cell, circulating rare cells (CRCs), circulating stem cells (e.g. tumor stem cells and bone marrow stem cells), fetal cells, bacteria, vires, epithelial cells, endothelial cells or the like). The particle of interest can be captured on the surface. The surface can be coated in a non-fouling composition. The non-fouling composition can comprise a binding moiety that specifically binds to the particle of interest.

Capture

In order to capture a particle of interest, a sample comprising a particle of interest can be flowed over a surface. The flow rate of the sample on the surface coated with the non-fouling layer can comprise a linear velocity of at least 0.1, 0.2, 0.3, 0.4, 0.5, 1, 1.5, 2, 2.5, 3, 3.5, 4, 4.5, 5, 5.5, 6, 6.5, 7, 8, 9, 10 or more mm/s. The flow rate can comprise a linear velocity of at most 0.1, 0.2, 0.3, 0.4, 0.5, 1, 1.5, 2, 2.5, 3, 3.5, 4, 4.5, 5, 5.5, 6, 6.5, 7, 8, 9, 10 or more mm/s. The flow rate can comprise a linear velocity from 0.5 to 4 mm/s. The flow rate can comprise a linear velocity from 2.5 to 4 mm/s. The flow rate can be a rate wherein at least 50, 60, 70, 80, 90, or 100% of the particles of interest bind to the binding moiety. The flow rate can be a rate wherein at most 50, 60, 70, 80, 90, or 100% of the particles of interest bind to the binding moiety. The flow rate can be a rate that does not damage the particles of interest.

The surface can capture at least 50, 60, 70, 80, 90 or 100% of the particles of interest from the sample. The surface can capture at most 50, 60, 70, 80, 90 or 100% of the particles of interest from the sample. The surface can capture at least 5, 10, 25, 50, 100, 200, 300, 400, 500, 1000, 1500, 2000, or 2500 particles of interest per milliliter of sample. The surface can capture at most 5, 10, 25, 50, 100, 200, 300, 400, 500, 1000, 1500, 2000, or 2500 particles of interest per milliliter of sample. Overall the microfluidic devices and surfaces herein may have a capture efficiency for particles of interest (e.g., rare cells, CTCs, etc) that is at least 40%, 50%, 60%, 70%, 80%, 90%, 95%, or 99%. Capture efficiency of a cell of interest can be defined by defined as (number of confirmed rare cells captured)/(number of actual rare cells flowing through the device or adjacent to the surface)× 100%.

Purification by Washing

The surface can be further purified by removing non-specific particles of interest and/or other components of the sample. Particles of interest may be purified by removing non-specific particles (e.g., cells) and other unwanted components on the surface of a non-fouling composition. The non-fouling composition may have low affinity for non-specific particles and other unwanted components. For example, rinsing a lipid conjugate with a low flow buffer solution of about 0.8 dyne/cm2 to about 50 dyne/cm2 may be sufficient to remove non-specific particles and other unwanted components on the non-fouling composition.

Purification can be performed by flowing a wash buffer over the surface. The flow rate of the wash buffer can comprise a linear velocity of at least 0.1, 0.2, 0.3, 0.4, 0.5, 1, 1.5, 2, 2.5, 3, 3.5, 4, 4.5, 5, 5.5, 6, 6.5, 7, 8, 9, 10 or more mm/s. The flow rate of the wash buffer can comprise a linear velocity of at most 0.1, 0.2, 0.3, 0.4, 0.5, 1, 1.5, 2, 2.5, 3, 3.5, 4, 4.5, 5, 5.5, 6, 6.5, 7, 8, 9, 10 or more mm/s. The flow rate of the wash buffer can comprise a linear velocity from 0.5 to 4 mm/s. The flow rate of the wash buffer can comprise a linear velocity from 2.5 to 4 mm/s. The flow rate of the wash buffer can be a rate wherein at least 50, 60, 70, 80, 90, or 100% of the particles of interest remain bound to the binding moiety. The flow rate of the wash buffer can be a rate wherein at most 50, 60, 70, 80, 90, or 100% of the particles of interest remain bound to the binding moiety. The flow rate of the wash buffer can be a rate that does not damage the particles of interest. Damage can refer to morphological changes in the particle of interest, degradation of the particle of interest, changes in viability of the particles of interest, lysis of the particles of interest, and/or changes in gene expression (e.g., metabolism) of the particle of interest.

Flowing of the wash buffer (i.e., rinsing), can remove at least 40, 50, 60, 70, 80, 90, or 100% of non-specific particles of interest. Flowing of the wash buffer (i.e., rinsing), can remove at most 40, 50, 60, 70, 80, 90, or 100% of non-specific particles of interest. Flowing of the wash buffer can leech at least 1, 2, 3, 4, 5, 6, 7, 8, 9, 10, or 15% or more particles of interest from the non-fouling composition of the surface. Flowing of the wash buffer can leech at most 1, 2, 3, 4, 5, 6, 7, 8, 9, 10, or 15% or more particles of interest from the non-fouling composition of the surface.

Release

The methods of the disclosure provide a releasing method for collecting a particle of interest, wherein the released particle of interest is viable. Release of a particle of interest can be performed by flowing a foam composition of the disclosure over the surface (e.g., a surface comprising a non-fouling layer, linker, and/or binding moiety). Release of particle of interest may be via a gentle sweeping force. A gentle sweeping force as used herein may refer to a shear of air bubbles, a shear of air foams, a shear of emulsive fluid, ultrasonic vibration or an oil phase. In some instances, a foam composition comprising 4 milliliters of a 5% BSA in PBS, 2 mL of air, wherein at least 50% of the air bubbles of the foam composition have a diameter from about 10 to 100 micrometers can be flowed over a surface at a flow rate from 0.5-4 mm/s to release a particle of interest.

The flow rate of the foam composition can comprise a linear velocity of at least 0.1, 0.2, 0.3, 0.4, 0.5, 1, 1.5, 2, 2.5, 3, 3.5, 4, 4.5, 5, 5.5, 6, 6.5, 7, 8, 9, 10 or more mm/s. The flow rate of the foam composition can comprise a linear velocity of at most 0.1, 0.2, 0.3, 0.4, 0.5, 1, 1.5, 2, 2.5, 3, 3.5, 4, 4.5, 5, 5.5, 6, 6.5, 7, 8, 9, 10 or more mm/s. The flow rate of the foam composition can comprise a linear velocity from 0.5 to 4 mm/s. The flow rate of the foam composition can comprise a linear velocity from 2.5 to 4 mm/s. The flow rate of the foam composition can be a rate wherein at least 1%, 2%, 3%, 4%, 5%, 10%, 15%, 20%, 30%, 40%, or 50% of the particles of interest remain bound to the binding moiety. The flow rate of the wash buffer can be a rate wherein at most 1%, 2%, 3%, 4%, 5%, 10%, 15%, 20%, 30%, 40%, or 50% of the particles of interest remain bound to the binding moiety. The flow rate of the foam composition can be a rate that does not damage the particles of interest. Damage can refer to morphological changes in the particle of interest, degradation of the particle of interest, changes in viability of the particles of interest, lysis of the particles of interest, and/or changes in gene expression (e.g., metabolism) of the particle of interest. The foam composition may flow over the surface for about or more than 1 minute, 2 minutes, 3 minutes, 5 minutes, 8 minutes, 10 minutes, 12 minutes, 14 minutes, 16 minutes, 18 minutes, 20 minutes, 25 minutes, or 30 minutes.

The foam composition (e.g., the air bubbles of the foam composition), can result in the removal of the non-fouling composition and/or binding moiety from the surface. The foam composition can result in the removal of at least 50, 60, 70, 80, 90 or 100% of the non-fouling composition and/or binding moiety from the surface. The foam composition can result in the removal of at most 50, 60, 70, 80, 90 or 100% of the non-fouling composition and/or binding moiety from the surface. In some instances, the foam composition removes at least 70% of the non-fouling composition and/or binding moiety. In some instances, a foam composition comprising 4 milliliters of a 5% BSA in PBS, 2 mL of air, wherein at least 50% of the air bubbles of the foam composition have a diameter from about 10 to 100 micrometers flowed over a surface at a flow rate from 0.5-4 mm/s to can result in the removal of at least 50% of the non-fouling composition, binding moiety, linker, and/or particle of interest from the surface.

Particles of interest released by the foam composition of the disclosure may be collected in a collection device. In some embodiments, the collection device may act as a concentration device to concentrate the particles of interest. In some embodiments, a collection device may comprise a membrane. In some embodiments, the membrane may comprise pores with a diameter of about or less than 0.5 um, 1 um, 1.5 um, 2 um, 2.5 um, 3 um, 3.5 um, 4 um, or 5um. Based on the membrane pore size, particles of interest may be collected in an area within the collection device (e.g., membrane). For example, particles of interest larger in size than a pore size of the membrane may be collected on the membrane based on size separation. For example for a membrane having a pore size of 2 um, all cells including cancer cells and WBCs may be collected on the membrane. A negative pressure may be provided on a side of the collection device (e.g., membrane) opposite the side of particles of interest. A negative pressure may ensure that non-specific particles or air bubbles (e.g., foam) pass through pores on the membrane without causing membrane clogging or unexpected debris. A negative pressure may be of an amount that does not affect viability of cells. In some embodiments, cells may be collected in an area about or greater than 10, 20, 30, 40, 50, 60, 70, 80, 90, 100, 120, 140, 160, 180, 200, or more $mm^2$. After collection, the membrane may be removed and mounted on a microscope slide. After collection, the membrane may be imaged (e.g., fluorescently under a microscope). By collecting particles of interest to a small area of the collection device (e.g., membrane), performance of the methods and systems herein may be efficiently evaluated. By collecting particles of interest to a small area of the collection device (e.g., membrane), out of focus images may be limited.

Particles of interest released by the foam composition of the disclosure can be viable. Particles of interest released by the foam composition of the disclosure can be unviable. At least 50, 60, 70, 80, 90, or 100% of the particles of interest released by the foam composition can be viable. At most 50, 60, 70, 80, 90, or 100% of the particles of interest released by the foam composition can be viable. Viability can be determined by changes in morphology (e.g., lysis), gene expression (e.g., caspase activity), gene activity (shutdown of certain cellular pathways), and cellular function (e.g., lack of motility). In some instances, released cells can be used for downstream processes such as ELISAs, immunoassays, culturing, and nucleic acid sequencing. If a released cell fails to perform well in downstream assays, the cell can be referred to as unviable. In some instances, a foam composition comprising 4 milliliters of a 5% BSA in PBS, 2 mL of air, wherein at least 50% of the air bubbles of the foam composition have a diameter from about 10 to 100 micrometers can be flowed over a surface (e.g., comprising a non-fouling composition and a binding moiety) at a flow rate from 0.5-4 mm/s to release a particle of interest to release cells bound to the surface, wherein the at least 50% of the released cells are viable.

The released particles of interest can be at least 50, 60, 70, 80, 90 or 100% free of non-specific particles of interest. The released particles of interest can be at most 50, 60, 70, 80, 90 or 100% free of non-specific particles of interest. A non-specific particle of interest can be any cellular particle that is not a particle of interest. For example, a non-specific particle of interest can include, white blood cells, red blood cells, serum proteins, serum nucleic acids, and circulating epithelial cells. A non-specific particle of interest can refer to a particle that is unable to specifically bind to a binding moiety used in the microfluidic chip of the disclosure. In other words, a non-specific particle of interest may refer to a cell that does not express an antigen/receptor, specific for the binding moiety. In some instances, a foam composition comprising 4 milliliters of a 5% BSA in PBS, 2 mL of air, wherein at least 50% of the air bubbles of the foam composition have a diameter from about 10 to 100 micrometers flowed over a surface at a flow rate from 0.5-4 mm/s to can result in the removal of at least 50% of the non-fouling composition from the surface, and/or result in released particles of interest that are at least 50% free of non-specific particles of interest.

In some instances, a population of cells can be released from the surface (e.g., of a microfluidic channel, e.g., of a non-fouling composition). A population of cells can comprise at least 1, 2, 3, 4, 5, 6, 7, 8, 9, 10, 100, 1000, 10000, 100000, or 1000000 or more cells. A population of cells can comprise at most 1, 2, 3, 4, 5, 6, 7, 8, 9, 10, 100, 1000, 10000, 100000, or 1000000 or more cells. A population of cells can be released from the surface with an efficiency of at least 50, 60, 70, 80, 90, 95, 99, or 100% efficiency. A population of cells can be released from the surface with an efficiency of at most 10, 20, 30, 40, 50, 60, 70, 80, 90, 95, 99, or 100% efficiency. In other words, at least 10, 20, 30, 40, 50, 60, 70, 80, 90, 95, 99 or 100% of the cells in a population of cells can be released by the foam composition of the disclosure. At most 50, 60, 70, 80, 90, 95, 99 or 100% of the cells in a population of cells can be released by the foam composition of the disclosure.

The cells of the population of cells may be viable. At least 50, 60, 70, 80, 90, 95, 99, or 100% of the cells in a population of cells may be viable. At most 50, 60, 70, 80, 90, 95, 99, or 100% of the cells in a population of cells may be viable.

A population of cells can comprise a plurality of particles of interest. A population of cells can comprise at least 20, 30, 40, 50, 60, 70, 80, 90, or 100% particles of interest. A population of cells can comprise at most 20, 30, 40, 50, 60, 70, 80, 90, or 100% particles of interest. A population of cells can comprise a plurality of non-particles of interest. A population of cells can comprise at least 20, 30, 40, 50, 60, 70, 80, 90, or 100% non-particles of interest. A population of cells can comprise at most 20, 30, 40, 50, 60, 70, 80, 90, or 100% non-particles of interest.

The air bubbles of the foam composition of the disclosure can remove the non-fouling composition by interacting with the non-fouling composition. The air-liquid interaction of the air bubble can be hydrophobic. It can interact with the hydrophobic part of the non-fouling composition. When the hydrophobic part of the non-fouling composition comprises the hydrophobic tails of a lipid bilayer, the air bubble can interact with the hydrophobic tails of the lipid bilayer and disrupt the bilayer, thereby dislodging the non-fouling composition from the surface.

In some instances, when the air bubble interacts with the lipid bilayer it can generate a solid-liquid-air contact line (e.g., the contact between the air, liquid and cell). The combination of the contact angle of the air bubble on the cell, and the surface tension of the liquid-air interface of the bubble can be a driving force for pulling the cells off the surface. If the tension of the air-liquid interface of the bubble against the cell is too strong, it can damage the cell. If the surface tension is too weak, the cell may not be removed from the surface. Surface tension can be controlled by the components of the foam composition.

The interaction of the foam composition with the surface (e.g., cell), can result in the reorganization of the surface and/or the non-fouling composition (e.g., molecular changes). For example, a surface comprising a non-fouling composition comprising a lipid bilayer can be disrupted to a monolayer, and/or individual lipid molecules after by interaction with the air bubble of the foam composition.

Isolated cells (such as circulating tumor cells CTCs) may be substantially pure. As used herein, the term "substantially pure population of CTCs" may refer to a cell population where at least about 40, 50, 60, 70, 80, or 90% of the cells are CTCs. In some embodiments, the substantially pure population of CTCs may contain no more than about 30%, no more than about 25%, no more than about 20%, no more than about 15%, no more than about 10%, no more than about 5%, no more than about 4%, no more than about 3%, no more than about 2%, no more than about 1%, no more than about 0.5% non-CTCs. In some embodiments, at least about 70%, at least about 75%, at least about 80%, at least about 85%, at least about 90%, at least about 95%, at least about 96%, at least about 97%, at least about 98%, or at least about 99% of the cells in the substantially pure population of CTCs may be CTCs.

In some embodiments, a lipid layer may be an anti-EpCAM-SLB, and the lipid layer may be incorporated into a microfluidic chip with etched patterns designed to enhance chaotic mixing. By controlling the fluid flow parameters, target cells such as CTCs can be captured. Flow rate of a buffer may subsequently be increased such that any nonspecifically adsorbed blood cells are removed without displacing any of the bound CTCs. The purified CTCs may be eluted from the device via the disruption of SLB assembly (but not the cell membrane or protein binding site), by a gentle sweep of air foams. The CTCs may be released gently to remain viable and suitable for downstream molecular analysis or cultivation.

Compositions

A composition of the disclosure can comprise a released particle of interest (e.g., released rare cell). A released particle of interest can refer to a cell released by the methods of the disclosure (e.g., the flowing of foam and air bubbles over a surface comprising a non-fouling layer). In some instances, during the releasing step, the non-fouling composition, the binding moiety, the linker, and the particle of interest, or any combination thereof are released together. In some instances, during the releasing step, the non-fouling composition, and the particle of interest are released together.

A composition of the disclosure can comprise a released cell, a non-fouling layer, and an air bubble from the foam composition. The air bubble can comprise the released cell and the non-fouling layer. In other words, the air bubble can partially envelop the lipids of the non-fouling layer.

Cell Culture

Released cells may undergo cell culture. Cell culture as used herein may mean growth, maintenance, transfection, or propagation of cells. Cell culture may be in a culture medium. Culture medium as used herein may mean a liquid solution used to provide nutrients (e.g., vitamins, amino acids, essential nutrients, salts, and the like) and properties (e.g., similarity, buffering) to maintain living cells (or living cells in a tissue) and support their growth.

Cell Preservation

Released or cultured cells may undergo cell preservation. High viability storage of cells may be important in clinical medicine and biopharmaceutical development. Cryopreservation may be commonly used for reliable long-term stabilization of cells. Isolated cells may be stored under cryopreservation for long term storage.

Analysis

Collected cells can be detected and counted by any means such as optical (e.g., visual inspection), automated counting, microscopy based detection, FACS, and electrical detection, (e.g., Coulter counters). Counting of the cells, or other particles of interest, isolated using the methods of the disclosure can be useful for diagnosing diseases, monitoring the progress of disease, and monitoring or determining the efficacy of a treatment. Counting particle of interest (e.g., cells) can be of use in non-medical applications For example, counting particles of interest may be useful for determination of the amount, presence, or type of contaminants in environmental samples (e.g., water, air, and soil), pharmaceuticals, food, or cosmetics.

One or more properties of the cells and/or particles of interest, or portions thereof collected by the methods of the disclosure can be measured. Examples of biological properties that can be measured can include mRNA expression, protein expression, and DNA quantification. The particles of interest isolated by the methods of the disclosure can be sequenced. Sequencing can be useful for determining certain sequence characteristics (e.g., polymorphisms and chromosomal abnormalities)

Lysis may be employed to analyze particles of interest (e.g., cell). Lysis may occur while particles of interest are bound to a non-fouling composition. Particles of interest may be analyzed in presence of non-specifically retained particles.

Genetic information may be obtained from a particle of interest (e.g., cell) captured by a binding moiety of a non-fouling composition. Such genetic information can include identification or enumeration of particular genomic DNA, cDNA, or mRNA sequences; identification or enumeration of cell surface markers; and identification or enumeration of proteins or other intracellular contents that is indicative of the type or presence of a particular tumor. Cells can be analyzed to determine the tissue of origin, the stage or severity of disease, or the susceptibility to a particular treatment.

Particles of interests collected by the methods of the disclosure can be assayed for the presence of markers indicative of cancer stem cells. Examples of such markers can include C-MET, EpCAM, MUC-1, EGFR, CD133, CD44, CD24, epithelial-specific antigen (ESA), Nanog, BMI1, DAPI, CK20, CD45, CDH17, CDX2, CK7, CK8, CK18, CK19, TTF-1, CDX2, PSA, PSMA, CEA, panCK, TCN, SULT2B1, ALDOB, COL11A1, PI3, CCL20, MTHFD11, IL-1b, SRPX2, SLCO4A1, TESC, IL-23, CD45, and the like.

Cell staining can be performed using antibodies, e.g., monoclonal antibodies, which recognize specific cell types within the population of cells. The antibodies may be directly labeled with a fluorescent compound or indirectly labeled using, for example, a fluorescent-labeled second antibody which recognizes the first antibody. A panel of antibodies may be used to analyze a cell population in a multi-marker imaging approach. For example, different antibodies may be labeled with different colors and subsequently imaged and/or analyzed in a flow cytometer. In some instances, a multi-marker imaging approach may increase sensitivity of detection of CTCs and aid in identifying CTC subpopulations expressing particular therapeutic targets. The panel of antibodies may comprise 1, 2, 3, 4, 5, 6, 7, 8, 9, 10, 12, 15, 20 or more different types of antibodies. For example, the panel of antibodies may comprise antibodies corresponding to markers panCK, CK18, CK7, TTF-1, CK20, CDX2, PSA, and PSMA. For example, the panel of antibodies may comprise anti-panCK, anti-CK18, anti-CK7, anti-TTF-1, anti-CK20 mixed with anti-CDX-2, anti-PSA mixed with anti-PSMA.

The staining of a cell population with panel of antibodies may involve multiple manipulative steps. For example, 1) a series of samples from a population may be prepared; 2) one antibody from the panel may be combined with each of the samples, and the resulting mixture may be incubated so that the antibody can bind to the cells in the sample which the antibody recognizes; 3) one or more washings of the cells may be performed to remove any unbound antibody. In some instances, if the first antibody has not been directly labeled with a fluorescent compound, additional incubations with other antibodies or reagents and additional washings may be required to label the unconjugated primary antibody bound to the cells.

Cell staining can be followed by flow cytometric analysis to determine the number of stained cells relative to the total number of cells in the population. Commercially available equipment, e.g., equipment manufactured by such companies as Coulter Electronics, Hialeah, Fla., and Becton-Dickinson, Mountain View, Calif., may be utilized for performing the cell sorting and counting step of the analysis.

Clinical Applications

Characterization of CTCs can provide valuable information for treating patients and aiding with individualized treatment strategies. For example, the number and/or change in number of detectable CTCs can be used to predict patient outcome and response to therapy. For example, CTCs can be used to identify genetic alterations in tumor cells that impact therapy decisions. In some instances, the ability to detect, quantify, or evaluate molecule features of CTCs within a patient's bloodstream can allow genetic manipulations of cell characteristics and/or changing cell behavior while CTCs are en route to the metastatic site and thus altering patient outcome. Further analysis, for example via genomics, epigenomics, transcriptomics, and/or proteomics methods, of CTCs may help clinicians understand the tumor biology in real-time. In some instances, CTCs can be used to study responses of cancer cells to therapeutic pressure, and discover novel biomarkers and drug targets for cancers.

The systems and methods described herein may be useful in assessing a favorable or unfavorable survival, and may aid in preventing unnecessary therapy that could result in harmful side-effects when the prognosis is favorable. Thus, the present invention can be used for prognosis of any of a wide variety of cancers, including without limitation, solid tumors and leukemia's including highlighted cancers: apudoma, choristoma, branchioma, malignant carcinoid syndrome, carcinoid heart disease, carcinoma (i.e. Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell), histiocytic disorders, leukemia (i.e. B-cell, mixed-cell, null-cell, T-cell, T-cell chronic, HTLV-II-associated, lymphocytic acute, lymphocytic chronic, mast-cell, and myeloid), histiocytosis malignant, Hodgkin's disease, immunoproliferative small, non-Hodgkin's lymphoma, plasmacytolma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulose cell tumor, gynandroblastoma, hepatoma, hidradenoma, islet cell tumor, icydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophillia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondroscarcoma, cystosarcoma, phyllodes, fibrosarcoma, hemangiosarcoma, leiomyo sarcoma, leukosarcoma, liposarcoma, lymphangiosarcoma, myoswarcoma, myxosarcoma, ovarian carcinoma, rhabdomyosarcoma, sarcoma (i.e. Ewing's experimental, Kaposi's and mast-cell), neoplasms (i.e. bone, breast, digestive system, colorectal, liver, pancreatic, pituitary, testicular, orbital, head and neck, central nervous system, acoustic, pelvic, respiratory tract, and urogenital, neurofibromatosis, and cervical dysplasia.

A volume of blood necessary for analysis using the systems and methods described herein may be equal to about or less than 25 uL, 50 uL, 75 uL, 100 uL, 0.2 mL, 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL or 8 mL, 9 mL, 10 mL, 11 mL, 12 mL, 13 mL, 14 mL, 15 mL or 16 mL. The volume of blood necessary for analysis using the systems and methods described herein may be equal to or up to 25 uL, 50 uL, 75 uL, 100 uL, 0.2 mL, 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL or 8 mL, 9 mL, 10 mL, 11 mL, 12 mL, 13 mL, 14 mL, 15 mL or 16 mL.

Method for Identifying a CTC Source or Tissue of Origin of Cancer

Presence of certain markers on the particles of interest (e.g., CTC) may be indicative of a source or origin of the CTC or a tissue of origin of cancer. Markers may be identified by staining the particles of interests with particular (e.g., specific) antibodies and subsequent imaging (e.g., fluorescent imaging). For example, CK18 may be largely expressed in simple epithelia, ductal epithelia, and pseudostratified epithelia, which may be a useful marker for carcinomas. For example, CK18 may be used as a carcinoma detection marker based on the expression in breast, lung, colorectal, prostate, and pancreatic cancer. For example, particles of interest such as CTCs may be stained with anti-CK18 and the presence of CK18 markers may be assessed. For example, presence of CK7 may be used as a proxy of the CTCs originating from breast, lung, or pancreas. For example, CK7 may be used as a proxy of identifying CTCs originating from breast, lung, or pancreatic cancer. For example, particles of interest such as CTCs may be stained with anti-CK7 and the presence of CK7 markers may be assessed. For example, presence of TTF-1 may be used as a proxy of the CTCs originating from lung, thyroid, or diencephalons. For example, presence of TTF-1 may be used as a proxy of CTCs originating from lung cancer, thyroid cancer, or diencephalic syndrome. For example, particles of interest such as CTCs may be stained with anti-TTF-1 and the presence of TTF-1 markers may be assessed. For example, anti-CK20 mixed with anti-CDX-2 may be used to detect CTCs originating from the colon. For example, anti-CK20 mixed with anti-CDX-2 may be used to detect CTCs originating from colorectal cancer. For example, anti-PSA mixed with anti-PSMA may be used to detect CTCs originating from the prostate. For example, anti-PSA mixed with anti-PSMA may be used to detect CTCs originating from prostate cancer. In some instances, combining CK20 and CK8/18/19 may significantly increase CTC detection rate.

A multi-marker analysis for CTC detection may be utilized for clinical application. For example, a panel of antibodies may be used to analyze a cell population in a multi-marker imaging approach. The panel of antibodies may comprise 1, 2, 3, 4, 5, 6, 7, 8, 9, 10, 12, 15, 20 or more different types of antibodies. For example, the panel of antibodies may comprise antibodies corresponding to markers panCK, CK18, CK7, TTF-1, CK20, CDX2, PSA, and PSMA. For example, the panel of antibodies may comprise anti-panCK, anti-CK18, anti-CK7, anti-TTF-1, anti-CK20 mixed with anti-CDX-2, anti-PSA mixed with anti-PSMA. Anti-X, where X is any marker as referred to herein may refer to an antibody corresponding or specific toward the marker X. CTC detection assays with multi-marker can not only applicable for different types of cancers to establish clinical correlation but can also make CTC as an early detection tool for the healthy individual cancer screening, or early stage cancer patients, even individuals with unknown primary source of cancer.

Figure 4:
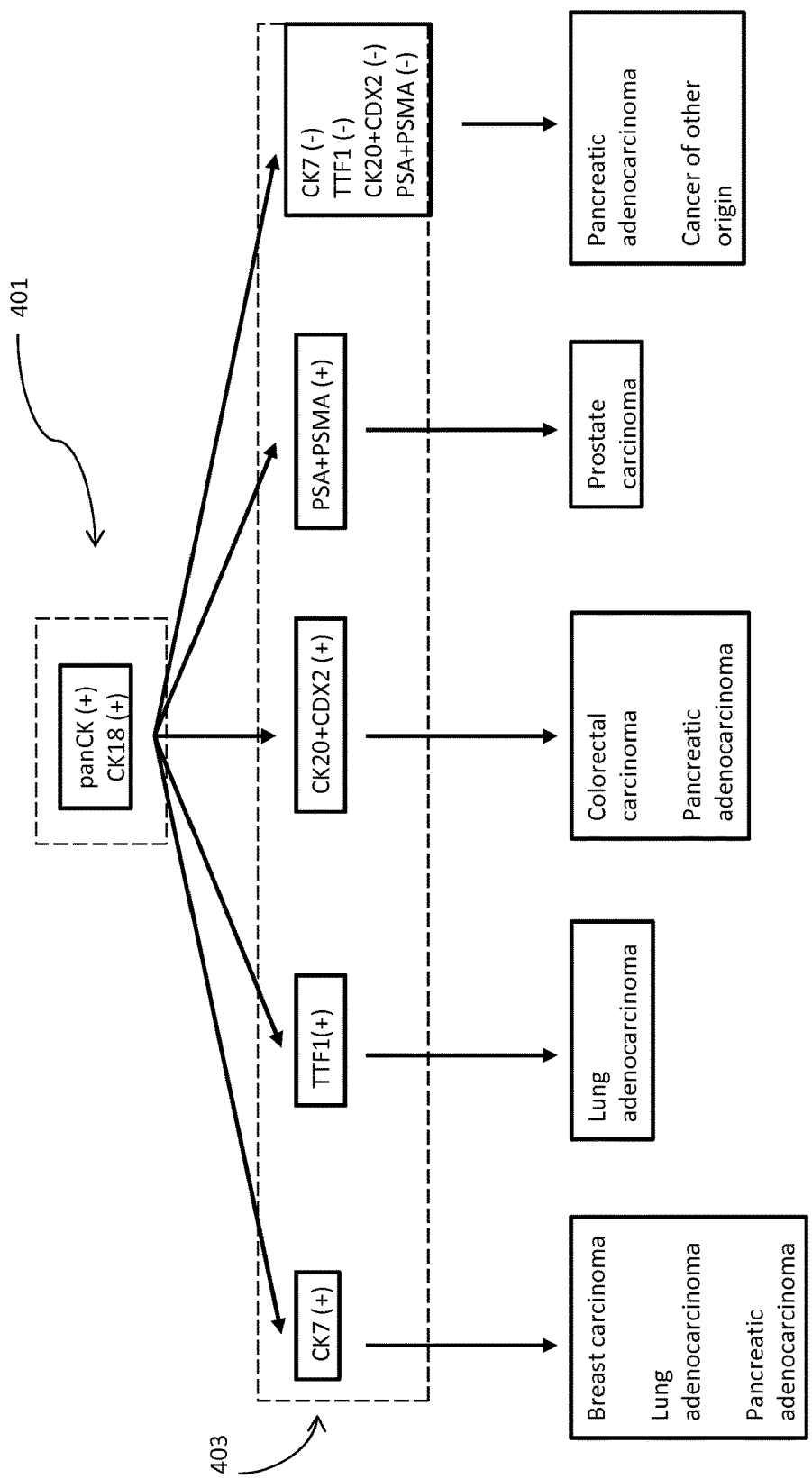
FIG. 4 provides a decision tree for CTC detection.

FIG. 4 provides a decision tree for CTC detection, in accordance with embodiments. For example, the panel of antibodies may comprise anti-panCK, anti-CK18, anti-CK7, anti-TTF-1, anti-CK20 mixed with anti-CDX-2, anti-PSA mixed with anti-PSMA. Anti-panCK and/or anti-CK18 may be used to analyze CTCs as a first step 401 (e.g., identify carcinoma cells). In the second step 403, anti-CK7, anti-TTF-1, anti CK20 mixed with anti-CDX-2, and anti-PSA mixed with anti-PSMA may be used to analyze CTCs. For example, CTCs positive for CK7 may indicate CTCs originating from breast, lung, or pancreas. For example, CTCs positive for CK7 may indicate breast, lung, or pancreatic cancer. For example, CTCs positive for TTF-1 may indicate CTCs originating from the lung, thyroid, or diencephalons. For example, CTCs positive for TTF-1 may indicate lung cancer, thyroid cancer, or diencephalic syndrome. For example, CTCs positive for anti-CK20 mixed with anti-CDX-2 may indicate CTCs originating from the colon. For example, CTCs positive for anti-CK20 mixed with anti-CDX-2 may indicate colorectal cancer. For example, CTCs positive for anti-PSA mixed with anti-PSMA may indicate CTCs originating from the prostate. For example, CTCs positive for anti-PSA mixed with anti-PSMA may indicate prostate cancer. A cancer rate, or possibility of cancer, may be predicted. For example, by using the panel of antibodies, if there are positive stained cells for different antibodies, the possibility of cell origin or origin of cancer may be predicted. For example, the prediction rate may be calculated as staining efficiency of each marker*cancer prevalence*100%. In some embodiments, the chance of breast, colorectal, prostate, and/or lung cancer may be predicted to be equal to about or greater than 1%, 5%, 15%, 20%, 30%, 35%, 40%, 45%, 50%, 55%, 60%, 65%, 70%, 75%, 80%, 85%, 90%, or 95%.

Molecular Analyses for Assessing Presence, Absence, Progression, and/or Severity of Disease The target cells described herein can be circulating tumor cells CTCs. The present disclosure provides systems and method for assessing disease progression (e.g., cancer progression) in a patient suffering from cancer based on molecular analyses on the CTCs. For example, a method for assessing cancer progression in a patient may comprise: 1) isolating circulating tumor cells (CTCs) from the patient according to methods described herein; and 2) performing one or more cellular or molecular analyses on the CTCs to determine cancer progression in the patient.

In some embodiments, the cancer is selected from the group consisting of lung cancer, esophageal cancer, bladder cancer, gastric cancer, colon cancer, skin cancer, papillary thyroid carcinoma, colorectal cancer, breast cancer, lymphoma, pancreatic cancer, prostate cancer, ovarian cancer, pelvic cancer, and testicular cancer.

In some embodiments, one or more cellular or molecular analysis comprises morphological analysis, genomics analysis, epigenomics analysis, transcriptomics analysis, proteomics analysis, or any combination thereof.

In some embodiments, the one or more cellular or molecular analysis may comprise determining one or more DNA mutations in the CTCs. In certain embodiments, the DNA mutation may comprise an insertion, a deletion, a substitution, a translocation, a gene amplification, or any combination thereof. In certain embodiments, the DNA mutation is located in a gene selected from the group consisting of KRAS, APC, TP53, BRAF, PTEN, EGFR, ERCC1, RRM1, ELM4, HER2, and ALK.

In some embodiments, the one or more cellular or molecular analysis may comprise determining protein expression level of a cancer specific gene in the CTCs. In some embodiments, the one or more cellular or molecular analysis may comprise determining RNA expression level of a cancer specific gene in the CTCs.

In some embodiments, the cancer specific gene is cytokeratin, prostate-specific antigen (PSA), prostate specific membrane antigen (PSMA), mucin-1 (MUC-1), human epidermal growth factor receptor 2 (HER2), chorionic gonadotropin (hCG), alpha fetoprotein (AFP), hepato-cellular carcinoma (HCC), N-cadherin, epithelial cell adhesion molecule (EpCAM), epidermal growth factor receptor (EGFR), ERCC1, androgen receptor (AR), human equilibrative nucleoside transporter 1 (hENT1), RRM1, or carcinoembryonic antigen (CEA).

In some embodiments, the method for assessing cancer progression in a patient may further comprise detecting the expression of one or more cancer-specific markers in the CTCs by staining, and enumerating the stained cells. The stage and/or prognosis of tumors in the patient can be determined based upon the combination results of molecular analysis and enumeration of the cancer-specific CTCs.

Cancer-specific markers may be utilized. Such markers may include (1) markers which are elevated in disease, such as human chorionic gonadotropin (hCG) which is elevated in testicular cancer and trophoblastic disease, and alpha fetoprotein (AFP) which is elevated in hepato-cellular carcinoma (HCC), (2) qualitatively altered mRNA or protein markers in disease, such as mRNA splice variants of CD 44 in bladder cancer and mutations in p53 protein in lung and colorectal cancer, (3) protein markers which are normally expressed in a specific tissue, organ or organ system but which appear in an inappropriate body compartment. Examples include prostate specific antigen (PSA) and carcinoembryonic antigen (CEA). CEA concentration is markedly elevated in the blood, plasma or serum of many patients diagnosed with colon disease including inflammatory bowel disease and adeno-carcinoma of the colon, and is used as an indicator of colorectal disease. In some instances, markers may comprise DAPI, cytokeratins (e.g., CK7, CK 18, CK19, CK20, etc), CD45, CDH17, CDX2, TTF-1, CDX2, PSA, PSMA, CEA, panCK, TCN, SULT2B1, ALDOB, COL11A1, PI3, CCL20, HER2, and the like. In some instances, the cancer specific marker may be cytokeratin, CDX1, CDH17, prostate-specific antigen (PSA), prostate specific membrane antigen (PSMA), mucin-1 (MUC-1), human epidermal growth factor receptor 2 (HER2), chorionic gonadotropin (hCG), alpha fetoprotein (AFP), hepatocellular carcinoma (HCC), N-cadherin, epidermal growth factor receptor (EGFR), ERCC1, androgen receptor (AR), human equilibrative nucleoside transporter 1 (hENT1), RRM1, or carcinoembryonic antigen (CEA), CD 44 and p53, epithelial cell adhesion molecule (EpCAM), GD2, GM2, GM1, GD1a, GT1b, A2B5, Tf, Tn, Globo H, CD133, CD24, CD44, CD90, ER, or PR.

In some instances, specific cancers may express specific markers. For example, presence, absence, progression, and/or severity of breast diseases may be assessed by staining rare cells (e.g., CTCs) with anti-CK7, anti-HER2, anti-ER, and anti-PR and analyzing the result. In some instances, presence, absence, progression, and/or severity of breast diseases may be assessed by staining rare cells (e.g., CTCs) with one or more antibodies selected from the group consisting of anti-CK7, anti-HER2, anti-ER, and anti-PR and analyzing the result. In some instances, all four antibodies may be used to stain the rare cells. For example, presence, absence, progression, and/or severity of colon, GI, and/or ovarian/endometrial diseases may be assessed by staining rare cells (e.g., CTCs) with DAPI, anti-CK20, and anti-CD45 analyzing the result. For example, presence, absence, progression, and/or severity of breast or prostate diseases may be assessed by staining rare cells (e.g., CTCs) with anti-PSA and anti-PSMA and analyzing the result. For example, presence, absence, progression, and/or severity of lung diseases may be assessed by staining rare cells (e.g., CTCs) with anti-CK7, anti-TTF1, and anti-EGFR and analyzing the result. In some instances, presence, absence, progression, and/or severity of lung diseases may be assessed by staining rare cells (e.g., CTCs) with one or more antibodies selected from the group consisting of with anti-CK7, anti-TTF1, and anti-EGFR and analyzing the result. In some instances, all three antibodies may be used to stain the rare cells.

In some embodiments, cancer presence, cancer progression, or tumor growth in a patient may be correlated with a CTC burden (e.g., CTC count, CTC quantity, etc). For example within an individual, when tumor volume is larger than a predetermined amount, the CTC burden and tumor growth may be correlated. The predetermined amount of tumor volume may be about or greater than 10, 20, 30, 40, 50, 60, 70, 80, 90, 100, 200, 300, 400, 500 $mm^3$.

Figure 22:
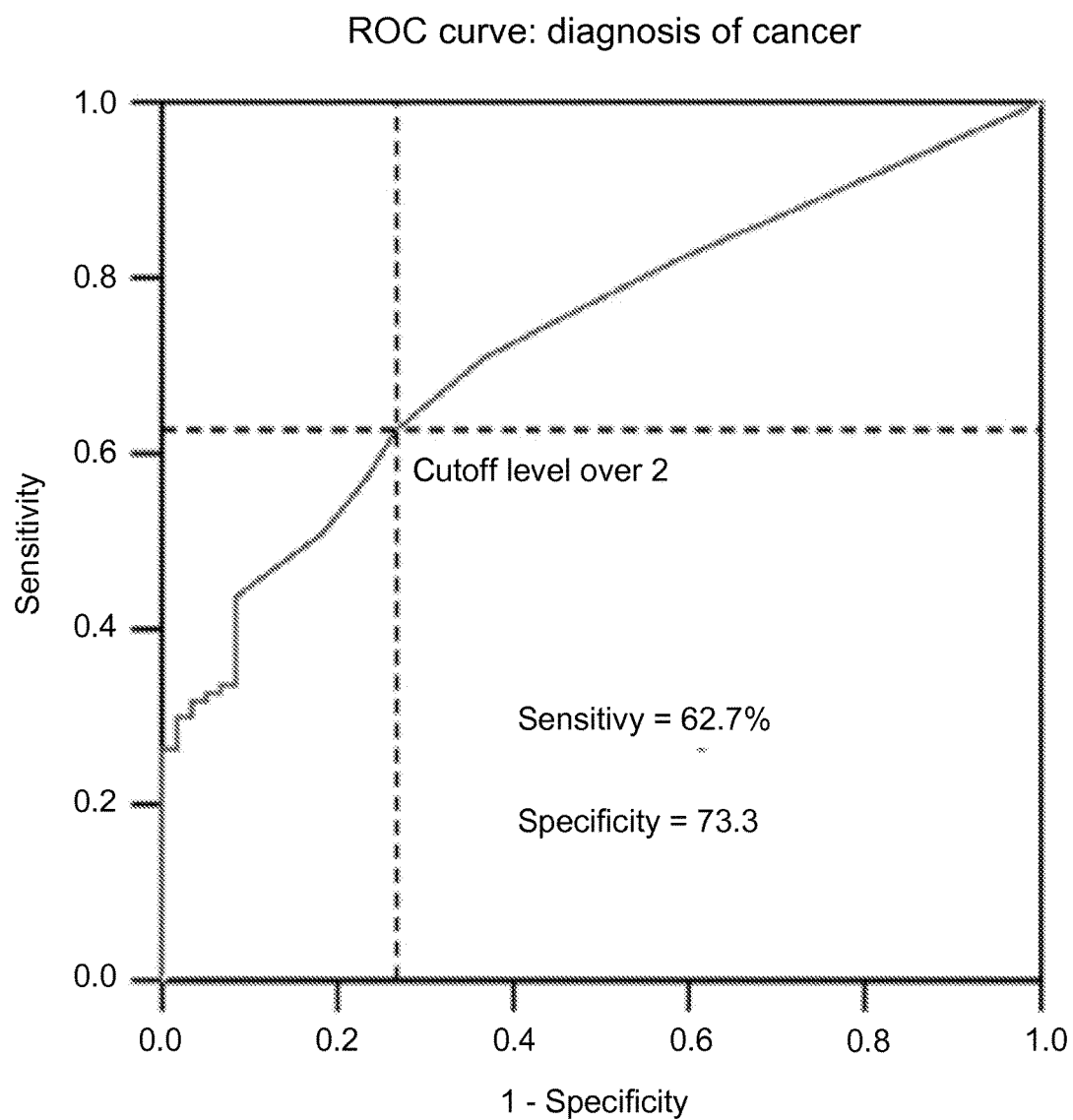
FIG. 22 shows sensitivity and specificity of cancer diagnosis by CTC.

In some embodiments, cancer presence or progression may be predicted based on a CTC cutoff value of number of CTCs found in a sample. Cancer presence or progression as used herein may comprise dysplasia, stage I, stage II, stage III, or stage IV cancer, metastases, micrometastases, polyps, and the like. A volume of blood necessary for detecting cancer presence or progression may be equal to about or less than 25 uL, 50 uL, 75 uL, 100 uL, 0.2 mL, 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL or 8 mL, 9 mL, 10 mL, 11 mL, 12 mL, 13 mL, 14 mL, 15 mL or 16 mL. A volume of blood necessary for detecting cancer presence or progression may be equal to or up to 25 uL, 50 uL, 75 uL, 100 uL, 0.2 mL, 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL or 8 mL, 9 mL, 10 mL, 11 mL, 12 mL, 13 mL, 14 mL, 15 mL or 16 mL. A CTC cutoff value in the sample may be about or more than 1, 2, 3, 4, 5, 6, 7, 8, 9, 10, 15, 20, 25, 30, 40, 50, 60, 80, 100, 120, 140, 160, 180, 200, 250, or 300 CTCs. For example, detection of 3 or more CTCs in a sample of 2 mL of peripheral blood may predict colorectal (CRC) cancer with a clinically acceptable specificity and sensitivity as shown in FIG. 22. For example, detection of 3 or more CTCs in a sample of up to 6 mL of blood may predict cancer with a clinically acceptable specificity and sensitivity. In some embodiments, cancer progression may be defined by distinct stages. For example, the stages may comprise normal/hyperplastic polyp, adenomatous/dysplasia polyp, stages 0/1, 2, 3, or 4. Each distinct stage of cancer progression may be predicted based on a specific CTC cutoff value with a clinically acceptable sensitivity and specificity. In some instances, presence of diseases may be assessed or determined prior to an imaging diagnosis. For example, using the methods and systems mentioned herein, diagnosis or prognosis of cancer may occur at a stage undetectable or undeterminable by imaging techniques. Diagnosis of cancer may be predicted based on a specific CTC cutoff value with a clinically acceptable sensitivity and specificity. The sensitivity may be about or greater than 50%, 60%, 65%, 70%, 75%, 80%, 85%, 90%, 95%, or 99%. The specificity may be about or greater than 50%, 60%, 65%, 70%, 75%, 80%, 85%, 90%, 95%, or 99%. The sensitivity and specificity may be defined by an area under a Receiver Operating Characteristic (ROC) curve. The area under the ROC curve may be about or greater than 0.5, 0.55, 0.6, 0.65, 0.7, 0.75, 0.8, 0.85, 0.9, or 0.95. The positive detection rate of cancer (corresponding to the distinct stages) may be about or greater than 10%, 20%, 30%, 40%, 50%, 60%, 70%, 80%, or 90%. In some embodiments, the cancer may be brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer.

In some embodiments, hematogenous spreading metastasis may be predicted based on a CTC cutoff value, or CTCs detected in a sample. A volume of blood necessary for detecting CTCs in a sample may be equal to about or less than 25 uL, 50 uL, 75 uL, 100 uL, 0.2 mL, 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL or 8 mL, 9 mL, 10 mL, 11 mL, 12 mL, 13 mL, 14 mL, 15 mL or 16 mL. A volume of blood necessary for detecting CTCs in a sample may be equal to or up to 25 uL, 50 uL, 75 uL, 100 uL, 0.2 mL, 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL or 8 mL, 9 mL, 10 mL, 11 mL, 12 mL, 13 mL, 14 mL, 15 mL or 16 mL. A CTC cutoff value in the sample may be about or more than 1, 2, 3, 4, 5, 6, 7, 8, 9, 10, 15, 20, 25, 30, 40, 50, 60, 80, 100, 120, 140, 160, 180, 200, 250, or 300 CTCs. For example, detection of 6 or more CTCs in a sample of 5 mL of peripheral blood may predict hematogenous spreading metastasis (e.g., liver metastasis) with clinically acceptable specificity and sensitivity. For example, a high CTC count in portal venous blood of patients with peri-ampullary malignance may be a significant predictor for liver metastases within 1 year after operation. The sensitivity may be about or greater than 50%, 60%, 65%, 70%, 75%, 80%, 85%, 90%, 95%, or 99%. The specificity may be about or greater than 50%, 60%, 65%, 70%, 75%, 80%, 85%, 90%, 95%, or 99%. The sensitivity and specificity may be defined by an area under a Receiver Operating Characteristic (ROC) curve. The area under the ROC curve may be about or greater than 0.5, 0.55, 0.6, 0.65, 0.7, 0.75, 0.8, 0.85, 0.9, or 0.95. The positive detection rate of hematogenous spreading metastasis may be about or greater than 10%, 20%, 30%, 40%, 50%, 60%, 70%, 80%, or 90%.

In some embodiments, benign diseases may be predicted based on a CTC cutoff value, or CTCs detected in a sample. A volume of blood necessary for detecting CTCs in a sample may be equal to about or less than 25 uL, 50 uL, 75 uL, 100 uL, 0.2 mL, 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL or 8 mL, 9 mL, 10 mL, 11 mL, 12 mL, 13 mL, 14 mL, 15 mL or 16 mL. A CTC cutoff value in the sample may be about or more than 1, 2, 3, 4, 5, 6, 7, 8, 9, 10, 15, 20, 25, 30, 40, 50, 60, 80, 100, 120, 140, 160, 180, 200, 250, or 300 CTCs. For example, detection of 3 or more CTCs in a sample of 2 mL of peripheral blood may predict benign colon disease with a clinically acceptable specificity and sensitivity. For example, detection of 3 or more CTCs in a sample of 2 mL of peripheral blood may predict polyps with a clinically acceptable specificity and sensitivity. The sensitivity may be about or greater than 50%, 60%, 65%, 70%, 75%, 80%, 85%, 90%, 95%, or 99%. The specificity may be about or greater than 50%, 60%, 65%, 70%, 75%, 80%, 85%, 90%, 95%, or 99%. The sensitivity and specificity may be defined by an area under a Receiver Operating Characteristic (ROC) curve. The area under the ROC curve may be about or greater than 0.5, 0.55, 0.6, 0.65, 0.7, 0.75, 0.8, 0.85, 0.9, or 0.95. The positive detection rate of benign disease may be about or greater than 10%, 20%, 30%, 40%, 50%, 60%, 70%, 80%, or 90%.

CTC detection may be affected by clinical conditions. For example, CTC detection may be elevated or deflated in patients with bowel obstruction, previous polypectomy, patients with blood loss, obstruction and/or perforation. Factors may be taken into consideration in order to increase specificity, sensitivity, and/or positive detection rate of diseases or metastasis mentioned herein. Such factors may include, but not limited to, age, sex, tumor location, CEA elevation, bowel obstruction by tumor, tumor size, gross type (e.g., polypoid, ulcerative, infiltrative), T classification, N class, histological differentiation (well, moderate), and the like. Based on the presence, absence, progression, and/or severity of disease (e.g., cancer), a drug therapy or regimen may be selected.

Methods for Assessing the Presence, Absence, and/or the Severity of Diseases

The present disclosure may further provide methods for assessing the presence and/or the severity of a disease in a subject. For example, a method for assessing the presence and/or the severity of a disease in a subject may comprise: 1) isolating circulating tumor cells (CTCs) from the patient according to the methods described herein; 2) detecting the expression of one or more disease-specific markers in the CTCs by staining; 3) enumerating the stained cells; and wherein the change in the number of stained cells as compared to a control is characteristic of the presence and/or the severity of a disease; thereby, assessing the presence and/or the severity of the disease.

In some embodiments, the presence and/or the severity of the disease may be determined based on the combination results of molecular analyses and enumeration of the disease-specific CTCs.

In some embodiments, the presence and/or the severity of the disease may be determined based on the combination of one or more factors which are all weighted separately to provide a single matrix value of the presence and/or severity of the disease. The factors may be taken into consideration in order to increase specificity, sensitivity, and/or positive detection rate of presence, absence, and/or severity of the disease. If two or more factors are used in a determination (e.g., of presence, absence, and/or severity of a disease), the level of each factor can be weighted and combined. Thus, a value may be provided by (a) weighting the determined level of each factor with a predefined coefficient, and (b) combining the weighted level to provide a value. The combining step can be either by straight addition or averaging (e.g., weighted equally) or by a different predefined coefficient. The factors can include: number of CTC, molecular characteristics of the CTC (presence or absence of certain mutations, gene expression, copy number variation, etc.), age of subject, gender of subject, heritage, location, family history of the disease, prior history with the disease, prior treatment or lack thereof. Each of the above factors may be assessed and weighted in coming up with a final display/outcome of likelihood of presence and/or severity.

The information regarding the one or more factors, their weights, or the value (e.g., determined through the combining step) may be stored in a computer readable form. The final display/outcome may be through a computer readable medium and/or a computer system. Such a computer system typically comprises major subsystems such as a central processor, a system memory (typically RAM), an input/output (I/O) controller, an external device such as a display screen via a display adapter, serial ports, a keyboard, a fixed disk drive via a storage interface and a floppy disk drive operative to receive a floppy disc, and a CD-ROM (or DVD-ROM) device operative to receive a CD-ROM. Many other devices can be connected, such as a network interface connected via a serial port.

The computer system may also be linked to a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

Figure 20:
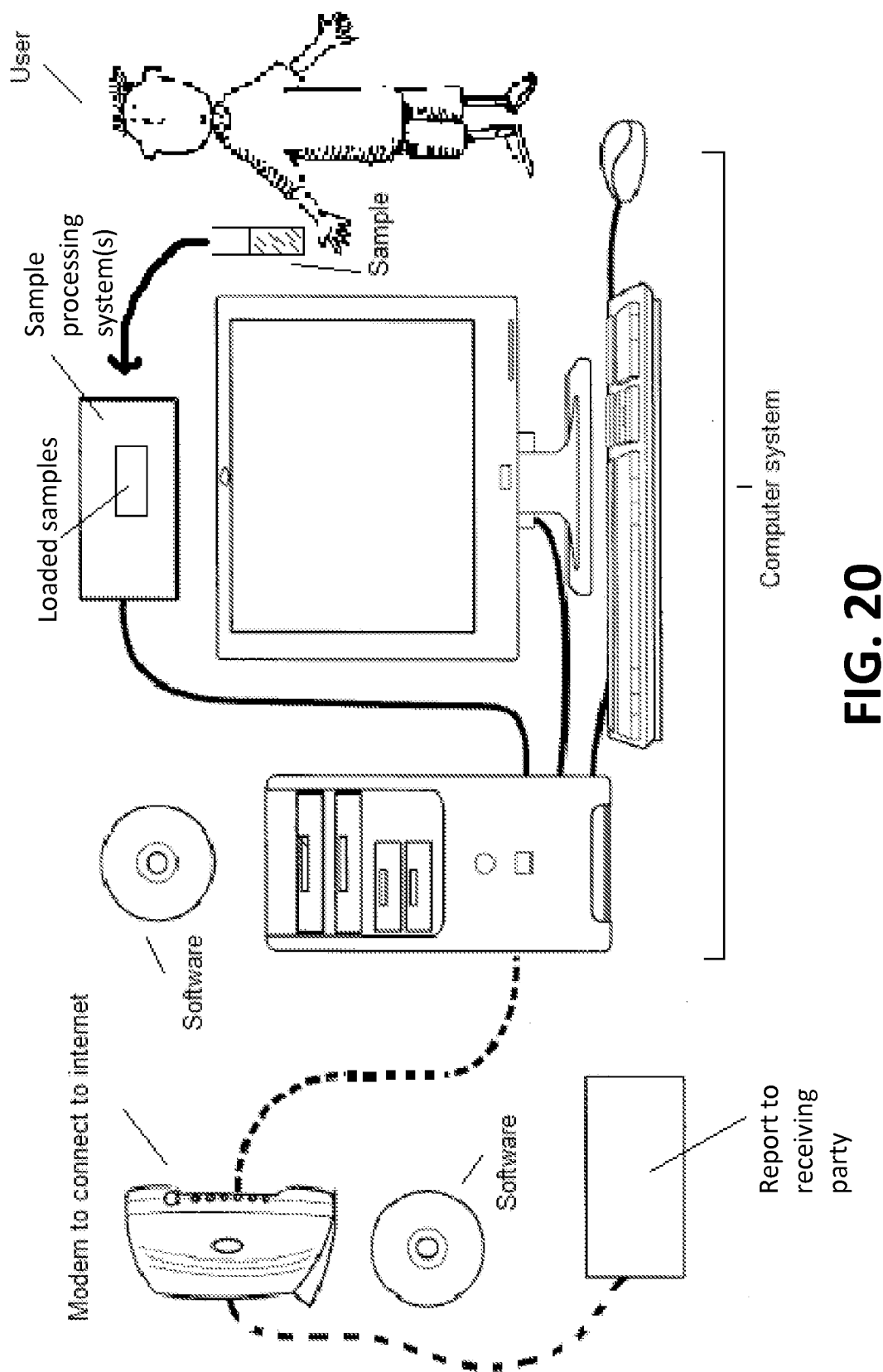
FIG. 20 illustrates the interaction between users, samples, computers, and outputs.

The computer system can comprise code for interpreting the results of a study evaluating the presence, absence, and/or severity of a disease. Thus in an exemplary embodiment, the results are provided to a computer where a central processor executes a computer program for determining the likelihood of a patient that has colorectal cancer. FIG. 20 illustrates the interaction between users, samples, computers, and outputs. For example, the user may be a patient. The sample may be a patient blood sample. The patient blood sample may comprise rare cells (e.g., CTC cells) which may be analyzed using the methods mentioned herein. The analysis may further comprise utilizing codes for interpreting results of a study. The analysis, codes, or the interpretation of the results of the study may be transmitted (e.g., through a computer to computer terminal, via data over a computer terminal, through a modem connected to internet, etc) and/or output to a receiving party.

The invention also provides the use of a computer system, such as that described above, which comprises: (1) a computer; (2) a stored bit pattern encoding testing results obtained by the methods of the invention, which may be stored in the computer; (3) and, optionally, (4a) a program for selecting a drug therapy for a patient having a disease, or (4b) a program for predicting the likelihood of a positive prognosis for a patient having cancer.

In some embodiments, the disease can be a cancer. The increased number of stained cells may be an indication of cancer or metastasis. Examples of the cancer include, but are not limited to, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer.

In some embodiments, the disease is a precancerous disorder. Examples of precancerous disorders include actinic keratosis, Barrett's esophagus, atrophic gastritis, Dyskeratosis congenita, Sideropenic dysphagia, Lichen planus, Oral submucous fibrosis, Solar elastosis and cervical dysplasia.

The presence (e.g., diagnosis of cancer or neoplasm) and/or severity of disease may be assessed via rare cells (e.g., CTC cells) as disclosed herein. In some instances, the CTC cells may be utilized as a marker for disease or severity of a disease. In some instances, the CTC cells may be utilized as a marker for diseases (e.g., cancer or neoplasm) before any imaging techniques (e.g., CT scan, ultrasound, PET, MRI, and the like) are able to detect presence of the disease. For example, a CTC count from a blood sample (e.g., peripheral blood sample) may be utilized as a marker for presence of a disease and/or severity of a disease (e.g., by comparing to a cutoff value).

Methods for Detecting Colorectal Cancer or Gastrointestinal (GI) Tract Diseases

The present disclosure may provide methods for detecting colorectal cancer or gastrointestinal (GI) tract diseases in a human patient. For example, a method for detecting colorectal cancer or gastrointestinal (GI) tract disease in a human patient may comprise: 1) isolating circulating tumor cells (CTCs) from the subject; 2) detecting the expression of one or more markers selected from the group consisting of DAPI, CK20, CD45, CDH17, CDX2, CK7, CEA, panCK, TCN, SULT2B1, ALDOB, COL11A1, PI3, CCL20, MTHFD11, IL-1b, SRPX2, SLCO4A1, TESC, and IL-23a in the CTCs by staining; 3) enumerating the stained cells; and wherein the number and/or change in number of stained cells as compared to a control is an indication of the presence and/or the severity of colorectal cancer or gastrointestinal (GI) tract diseases. For example, a method for detecting colorectal cancer or gastrointestinal (GI) tract disease in a human patient may comprise: 1) isolating circulating tumor cells (CTCs) from the subject; 2) detecting the expression of one or more markers comprising DAPI, CK20, CD45, CDH17, CDX2, CK7, CK8, CK18, CK19, TTF-1, CDX2, PSA, PSMA, CEA, panCK, TCN, SULT2B1, ALDOB, COL11A1, PI3, CCL20, MTHFD11, IL-1b, SRPX2, SLCO4A1, TESC, and IL-23a in the CTCs by staining; 3) enumerating the stained cells; and wherein the number and/or change in number of stained cells as compared to a control is an indication of the presence and/or the severity of colorectal cancer or gastrointestinal (GI) tract diseases.

In some embodiments, the presence and/or the severity of colorectal cancer or gastrointestinal (GI) tract diseases in the patient may be determined based on the combined results of molecular analyses and enumeration of the stained CTCs. The number of the stained cells in the sample is determined and compared to a control, e.g., a sample from an individual or group of individuals that are known to have cancer (positive control) or from an individual or group of individuals that are known not to have cancer (normal, non-disease, or negative control).

In some embodiments, detection may be based on the expression of DAPI+/CK20+/CD45− in the CTCs. For example, assuming control to be a standard range of DAPI+/CK20+/CD45− expression established for a group of individuals that are known not to have colorectal cancer or gastrointestinal (GI) tract diseases (normal, non-disease, or negative control), a higher than normal percentage of DAPI+/CK20+/CD45− expressing cells may indicate presence and/or the severity of colorectal cancer or gastrointestinal (GI) tract diseases.

In some embodiments, the human patient may have or be suspected of having colorectal cancer. In some embodiments, the colorectal cancer patient is suffering from colorectal cancer is stage 0, stage I, stage II, stage III and/or stage IV colorectal cancer.

In some embodiments, the human patient having or suspected of having gastrointestinal (GI) tract diseases. In certain embodiments, the gastrointestinal tract disease is Barret's esophagus, gastric ulcer, gastritis, leiomyoma, polyps, Crohn's disease, ulcerative colitis, pancreatitis, adenocarcinoma, mucinous adenocarcinoma, carcinoid tumor, squamous cell carcinoma, lymphoma, and sarcoma.

Method for Monitoring the Efficacy of a Therapeutic Regimen

The present disclosure may provide methods for monitoring efficacy of a therapeutic regimen. For example a method for monitoring efficacy of a therapeutic regimen may comprise: 1) isolating circulating tumor cells (CTCs) from a patient according to the methods described herein; 2) detecting the expression of one or more disease-specific markers in the CTCs by staining; 3) enumerating stained cells; and wherein the efficacy of a therapeutic regimen is determined based upon the number of the stained cells.

As used herein the term "sample" may include any chemical sample or biological sample. Chemical samples may refer to any chemical mixtures or chemical compounds. Biological samples may include, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" may refer to any solid or fluid sample obtained from, excreted by or secreted by any living organism, including single-celled microorganisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. Animal, as used herein, may refer to humans as well as non-human animals, at any stage of development, including, for example, mammals, birds, reptiles, amphibians, fish, worms and single cells. Cell cultures and live tissue samples may be considered to be pluralities of animals. In some embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

As used herein, the term "subject" may refer to a mammal. The mammal can be a human, non-human primate, mouse, rat, dog, cat, horse, or cow, but are not limited to these examples. Mammals other than humans can be advantageously used as subjects that represent animal models of disease, pre-disease, or a pre-disease condition. A subject can be male or female. A subject can be one who has been previously diagnosed or identified as having a health state (e.g., disease, pre-disease, or a pre-disease condition), and optionally has already undergone, or is undergoing, a therapeutic intervention for the health state. Alternatively, a subject can also be one who has not been previously diagnosed as having a given health state. For example, a subject can be one who exhibits one or more risk factors for a disease, pre-disease, or a pre-disease condition, or a subject who does not exhibit disease risk factors, or a subject who is asymptomatic for a disease, pre-disease, or pre-disease conditions. A subject can also be one who is suffering from or at risk of developing disease, pre-disease, or a pre-disease condition.

As used herein, the terms "condition," "disease," and "disorder" may be used interchangeably. The condition can be a hematological condition, an inflammatory condition, an ischemic condition, a neoplastic condition, infection, trauma, endometriosis, or kidney failure. The neoplastic condition can be selected from the group consisting of acute lymphoblastic leukemia, acute or chronic lymphocytic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic corneal nerve tumor, in situ carcinoma, intestinal ganglioneuroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

As used herein, the term "about" may refer to an amount within +/−1, 2, 3, 4, 5, 6, 7, 8, 9, or 10% of a subsequently mentioned value. For example, a sample of blood 11 mL may also be referred to as a sample of blood equal to about 10 mL.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervenining value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The following examples are presented in order to more fully illustrate the preferred embodiments of the invention. They should in no way be construed, however, as limiting the broad scope of the invention.

EXAMPLES

Example 1: Microchannel Fabrication and Surface Modification

Figure 5:
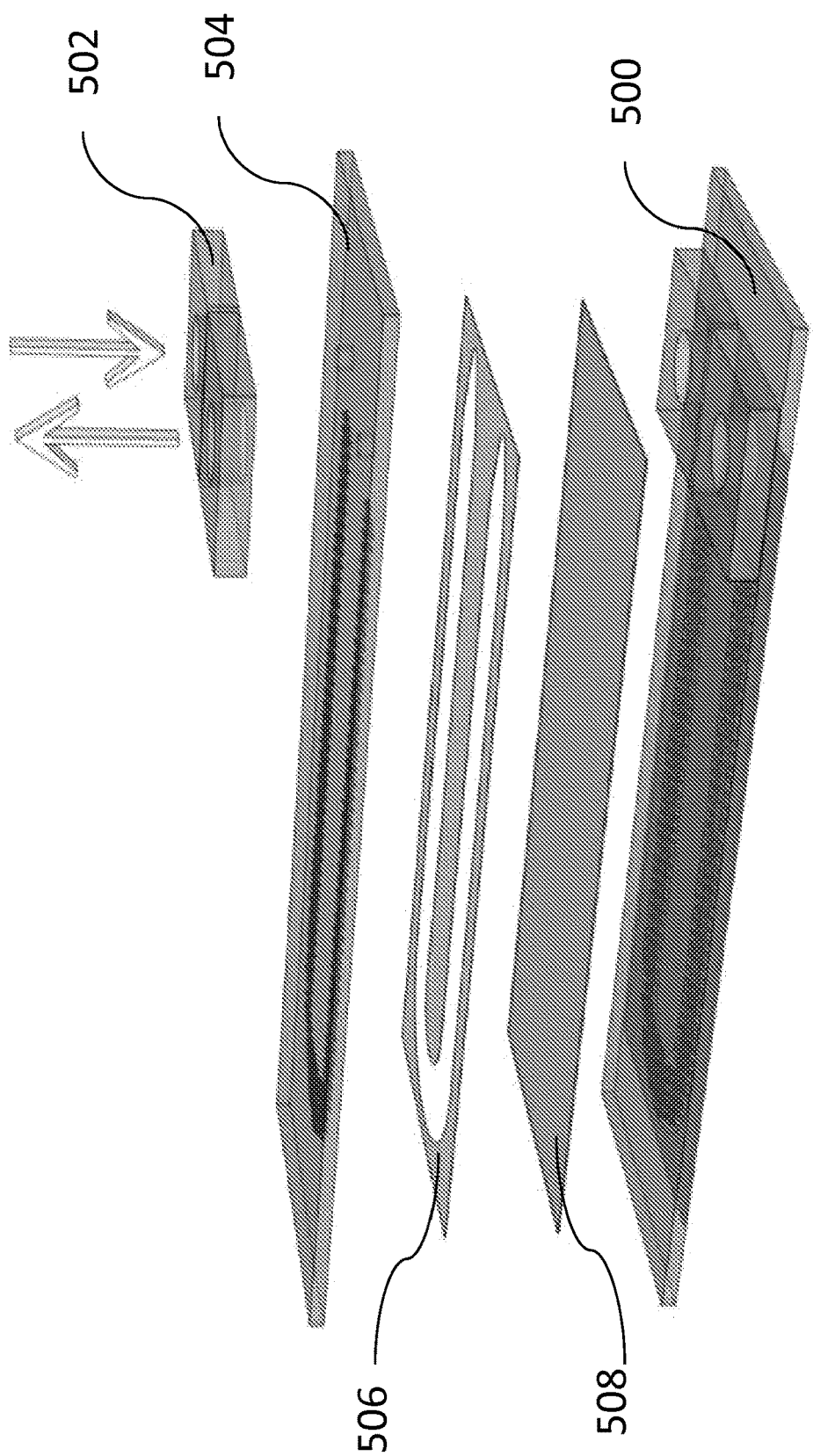
FIG. 5 provides an exploded view of a microfluidic device.

The microfluidic devices is fabricated with one inlet and outlet connected by a U-shape micro-channel using laser micro-machining technology. FIG. 5 provides an exploded view of a microfluidic device 500, in accordance with embodiments. The microfluidic device may comprise connectors 502, a top plate 504, a spacer 506, and a base slide 508. The construction of the device starts with the manufacture of a PMMA top plate having two drilled holes, inlet and outlet. A U shape is carved into the spacer, which is double-coated with acrylic adhesive on both sides to be bound to the PMMA top plate on one side and to a standard cover glass slide on the other side to form the microfluidic channel. PMMA connectors bind to the PMMA top plate. The micro-channel is about 110 mm long, 5.5 mm wide, and 0.06 mm high. In order to disrupt the streamlines followed by cells of laminar flow that dominates the flow conditions in microfluidic-based devices and to increase the number of cell-surface interactions, the upper surface of the micro-channel is patterned with a line groove whose average height is about 0.05 mm, average width about 0.25 mm, and average length about 1 mm.

Figure 6:
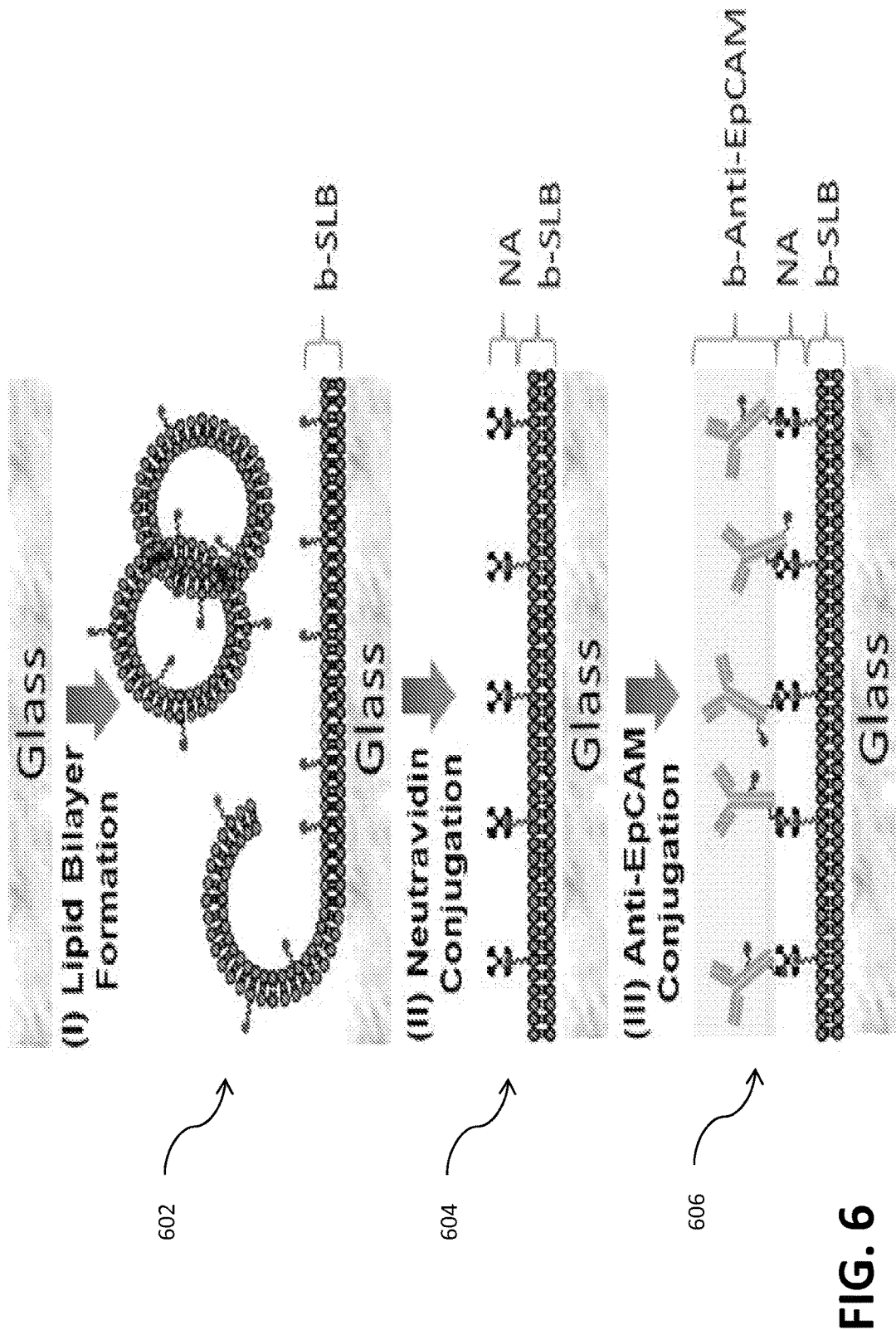
FIG. 6 illustrates sequential steps followed to prepare an antibody-tethered SLB coating in a microfluidic channel, in accordance with embodiments.

FIG. 6 illustrates sequential steps followed to prepare an antibody-tethered SLB coating in a microfluidic channel, in accordance with embodiments. In step 602, 0.2 mg/ml of lipid vesicles consisting of POPC/b-PE (95/5, 90/10, 85/15, and 80/20 mol/mol) is filled in the microfluidic channels and incubated for 1 h to form a complete lipid bilayer coating, followed by rinsing with 10 mM phosphate buffer saline (PBS) with 150 mM NaCl, pH 7.2 to remove excess vesicles and unbound lipids. In step 604, 0.1 mg/ml solution of Neutravidin (NA) is flown onto SLB-bPE-coated microchannel and incubated for 1 h, followed by rinsing with PBS buffer to remove excess NA. In step 606, 0.05 mg/ml solution of b-anti-EpCAM is introduced to conjugate with SA-SLB-bPE immobilized surface for 1 h, followed by rinsing with PBS buffer to remove excess b-anti-EpCAM.

Example 2: Generating a Foam Composition Using a Syringe

Figure 7:
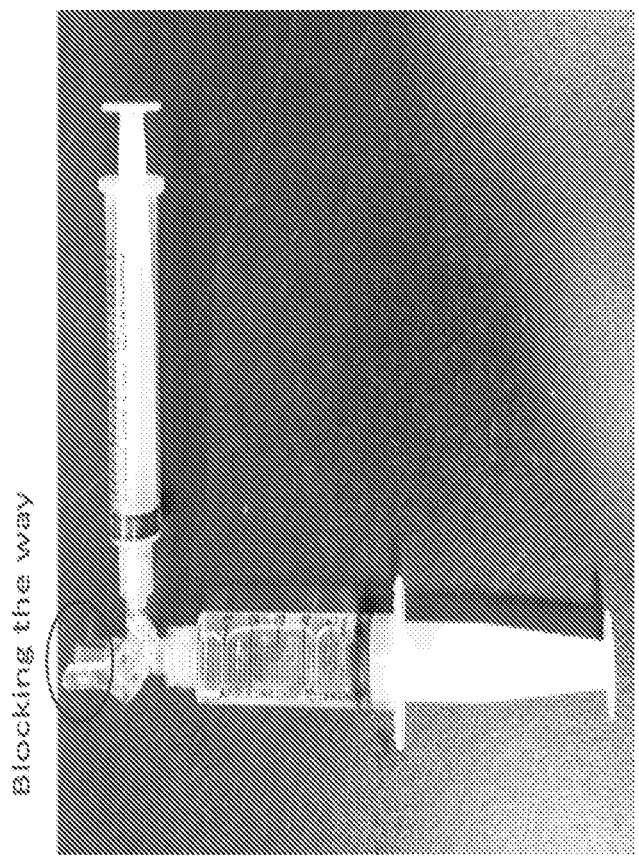
FIG. 7 depicts an exemplary device for the generation of a foam composition of the disclosure.
Figure 8:
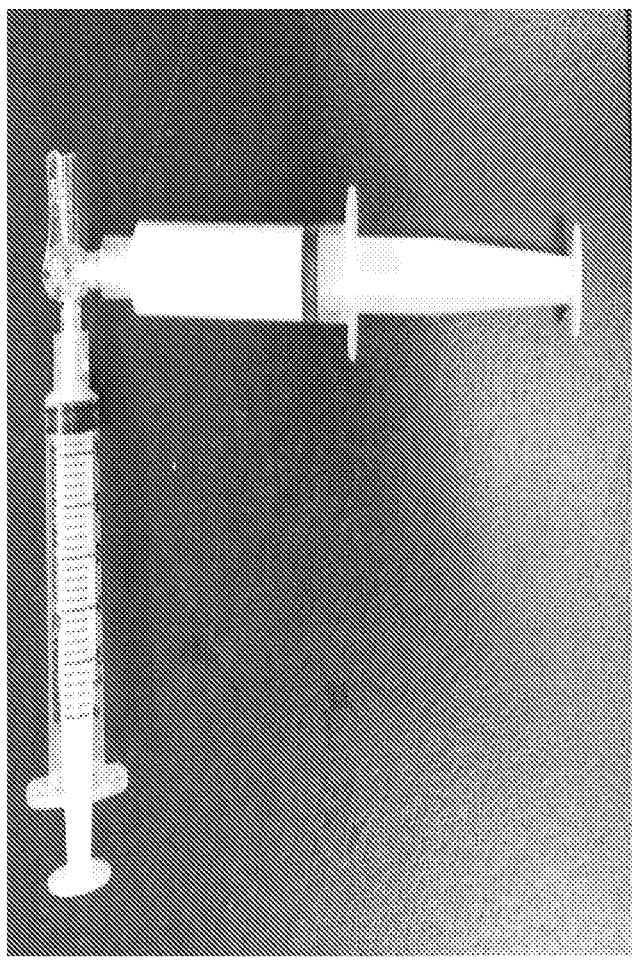
FIG. 8 depicts an exemplary device for the generation of a foam composition of the disclosure.

A foam composition is made by connecting a 5 mL first syringe containing 4 mL of 2:1 mixture of 5% BSA in phosphobuffered saline and 2 mL of air (See FIG. 7) with an empty second syringe. The two syringes are connected by a three-way valve. The third orifice of the valve that is not used is blocked to generate a continuous flow path between the two syringes. The piston of the first syringe comprising the mixture is depressed such that the contents of the first syringe are forced into the second syringe. The piston of the second syringe is then depressed to force the contents back into the first syringe. The process is repeated 10 times with each depressing taking less than five seconds. The process generates a foam composition of at least 1.5 milliliters where at least 50% of the air bubbles comprise a diameter from 10 to 100 micrometers (See FIG. 8).

Example 3: Generating a Foam Composition Using a Membrane

A fine pore membrane is place over a container comprising 4 mL of 2:1 mixture of 5% BSA in phosphobuffered saline and 2 mL air. The membrane comprises pores of 10 micrometers in diameter. The container is turned upside down such that the liquid in the container does not come out and does not drip through the fine pore membrane. The tip of a 5 mL syringe is placed on the membrane. The piston of the syringe is pulled thereby generating a force to pull the liquid from the container through the membrane. The liquid in the syringe is then transferred back into the container through the membrane, by depressing the piston of the syringe with pressure such that the liquid goes through the membrane. The process is repeated 5 times. The membrane is removed from the opening of the container and the foam composition is collected.

Example 4: Generating a Foam Composition by Vortexing 4 mL of a 2:1 mixture of 5% BSA in phosphobuffered saline and air is added to a 10 mL conical tube. The conical tube is vortexed for 20 seconds on a vortexer at the highest speed setting. The foam is removed from the conical tube and injected into a microfluidic chip that has already been contacted with a sample comprising a rare circulating tumor cell, in which the rare circulating cell has already bound to a binding moiety on the chip. The foam composition is flowed into the chip at 3 mm/s. The rare circulating tumor cell is released from the microfluidic chip and collected along with the foam. Nucleic acid from the rare circulating tumor cell is sequenced.

Example 5: Releasing Cells from a Non-Fouling Composition Using a Foam Composition A sample comprising a circulating tumor cell is contacted to the surface. The surface comprises a non-fouling composition. The non-fouling composition comprises a lipid bilayer and a binding moiety. The lipids of the non-fouling composition are non-covalently attached to the surface of the microfluidic channel (e.g., via Van der Waals interaction). The end of the lipid comprises a biotin moiety. The binding moiety comprises a streptavidin moiety. The biotin moiety and the streptavidin moiety bind together, thereby linking lipid to the binding moiety. The binding moiety is an anti-EpCAM antibody. The sample is flowed over the surface with a flow rate from 0.5 to 4 mm/s. The circulating tumor cells of the sample bind to the binding moiety. The surface of the non-fouling composition is purified by flowing a wash buffer comprising phosphobuffered saline over the non-fouling composition. The wash buffer removes non-specifically bound cells, but does not disrupt binding of the circulating tumor cells. 1.5 milliliters of a foam composition comprising 5% BSA in phosphobuffered saline and air bubbles, wherein at least 50% of the air bubbles comprise a diameter from 10 to 100 micrometers is flowed over the non-fouling composition. The air bubbles of the foam composition interact with the lipids of the non-fouling composition to remove the lipids from the surface. The lipids are removed by shear forces in combination with the amphiphilicity of the foam composition from the air-liquid interface between the air bubble and the non-fouling composition. The shear force turns the lipid bilayer inside out, thereby loosening the lipids so they are easily detached. The circulating tumor cells attached to the binding moiety of the non-fouling composition are also removed along with the lipids. The shear force is strong enough to remove the circulating tumor cells, but does not damage the cells. The released cells are viable. In this way, the circulating tumor cells are collected using a method of releasing by a foam composition.

Example 6: Cell Capture and Purification

Human colorectal cancer cell lines HCT 116 is maintained and grown in Dulbecco's modified Eagle medium (DMEM) (Gibco-RBL life Technologies, Paisley, UK) supplemented with 10% fetal bovine serum (FBS) and 1% antibiotic/antimycotic (100 U/ml penicillin sodium, 100 lg/ml streptomycin, and 0.25 lg/ml amphotericin B; Gibco-RBL life Technologies, Paisley, UK), at 37° C. with 5% CO2 atmosphere in a humidified incubator. At approximately 90% confluence, cells are pre-stained with CellTracker Green CMFDA or CellTracker Red CMTPX (Invitrogen, Calif., USA) for 1 h and followed by using 0.2% trypsin with 0.1% ethylenediamine-tetraacetic acid (EDTA) (Sigma Aldrich, St. Louis, USA) to resuspend cells in the same medium for subsequent experiments.

Figure 9:
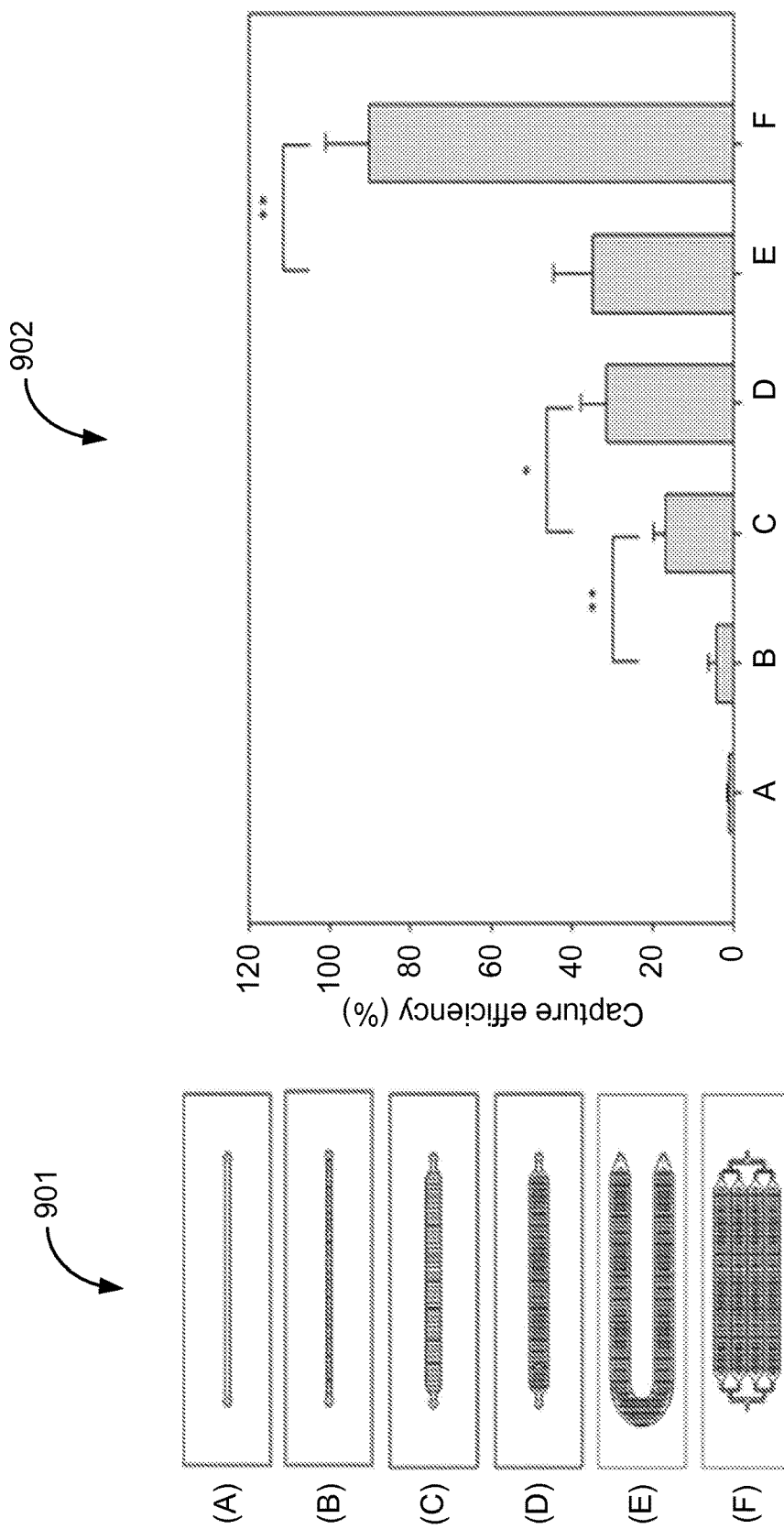
FIG. 9 illustrates the geometry and performance of 6 different microfluidic channel designs (A through F).
Figure 11:
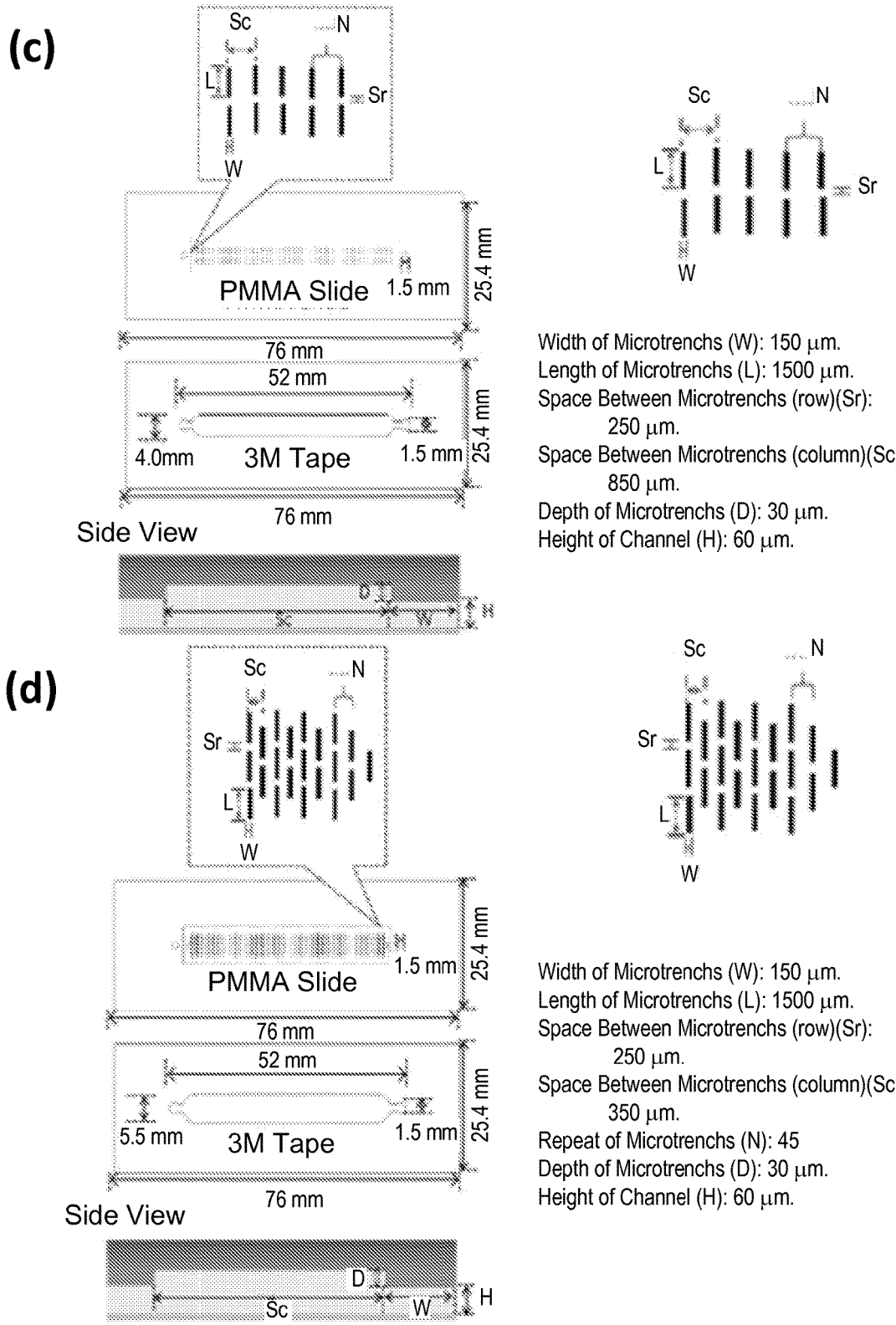
FIG. 11 illustrates the construction and dimension of microfluidic channel design C and D.

300 to 2000 HCT116 cells pre-stained with CellTracker Green are spiked into 1 mL whole blood collected from healthy individuals in EDTA tubes. After adequate mixing, the cell-blood mixture is flowed through the functionalized microchannel. Afterward, the microchannel is washed with 0.5 mL of phosphate buffer solution (PBS), followed by 0.3 mL of Hoechst solution (1 μg/mL in PBS) to stain the DNA in the nuclei of cells. The channel is fluorescently photo-micrographed to enumerate total number of cells bound to the channel surface. The cells that are double-positive with CellTracker and Hoechst dye are identified as HCT116 cells, and single positive DAPI-only cells are identified as non-specifically bound cells such as white blood cells (WBCs). FIG. 9 illustrates the geometry 901 and performance 902 of 6 different microfluidic channel designs (A through F), in accordance with embodiments. FIG. 10 illustrates the construction and dimension of microfluidic channel design A and B, in accordance with embodiments. FIG. 11 illustrates the construction and dimension of microfluidic channel design C and D, in accordance with embodiments. FIG. 12 illustrates the construction and dimension of microfluidic channel design E and F, in accordance with embodiments. In straight channels with simple patterns under same linear velocity, the capture performance (defined as the ratio of number of HCT116 cells bound on chip to the number of cells sending to chip) are very low due to the limited retention time and non-mixing flow pattern. Type A chip capture performance=1.2±0.6% and Type B chip performance=4.5±2.2%. When the number of micro patterns increases to create efficient mixing, capture efficiencies increase substantially: Type C chip=17.9±3.0% and Type D chip=33.5±6.6%. Further doubling channel length only slightly increased efficiency to 37.0±10.5% (Type E), while 4 parallel channels increased that to 93.7±8.9% (Type F). Type F chip is used for the remaining experiments unless specified otherwise.

Figure 13:
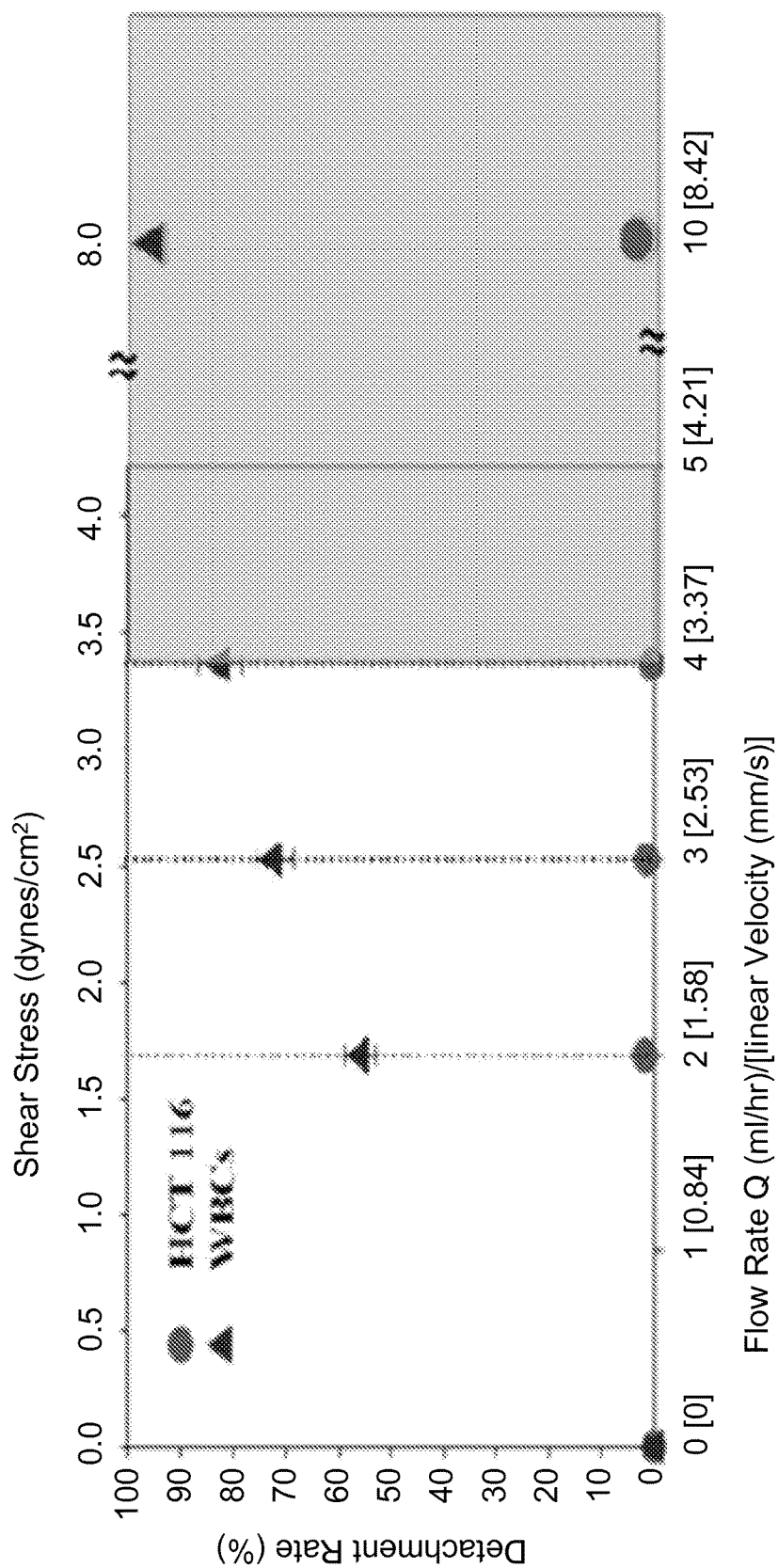
FIG. 13 illustrates purification via selectively increasing shear stress in the flow channel through increased buffer flow rates.

Purification of the captured cells is accomplished by increasing the flow rate of the PBS buffer flush. As the flow rate of PBS increased, the percentage of retained WBCs decreases significantly. The induced shear stress to remove 80-100% of WBCs while retaining 95%+HCT116 only requires ~4-8 dynes/cm2 (corresponding to flow rates of ~5-10 mL/h, FIG. 13). FIG. 13 illustrates purification via selectively increasing shear stress in the flow channel through increased buffer flow rates. Target HCT116 cells were retained while the shear stress is just large enough to flush out non-target WBCs. Shown in chart are cell detachment rates (%, Y-Axis) vs. flow rates [or linear velocity] (lower X-axis) and the corresponding shear stress (upper X-axis). Flow rates are generally maintained below the grey zone to avoid any potential loss of captured CTCs. *: P<0.05; **: P<0.01

The shear stress required to purify target cells is substantially lower than that was reported in previous cell detachment studies based on conventional antibody silanized surfaces and is considered low enough to have minimal or no impact on cell viability or protein expression. On the contrary, there are ~80% of HCT116 remained bounded even at 50 mL/h due to the strong antibody-antigen binding. For the clinical samples, an even smaller flow rate of 4 mL/h may be chosen to avoid any potential loss of CTCs.

Example 7: Release of Captured Viable Cells

Releasing viable CTCs from the microfluidic chips is a critical step enabling convenient cell preservation, downstream molecular analysis, and cell culture. Previous attempts using enzymatic cleavage, chemical, or mechanical forces to detach cells have shown either partial release or inevitable cell death, attributed by the breakage of antibody-antigen linkages or membrane rupture. SLB is a lipid molecular assembly at water-solid interface stabilized by inward hydrophobic-hydrophobic interactions of long hydrocarbon chains of lipid molecules and outward hydrophilic head groups interacting with water or hydrophilic silicon oxide surfaces (i.e. glass). The SLB assembly can be disintegrated by introducing hydrophobic component as simple as air bubbles. We offer a strategy to gently release adhesive CTCs without disrupting the antibody-antigen bonds by injecting continuous air foam to the microfluidics.

Figure 14:
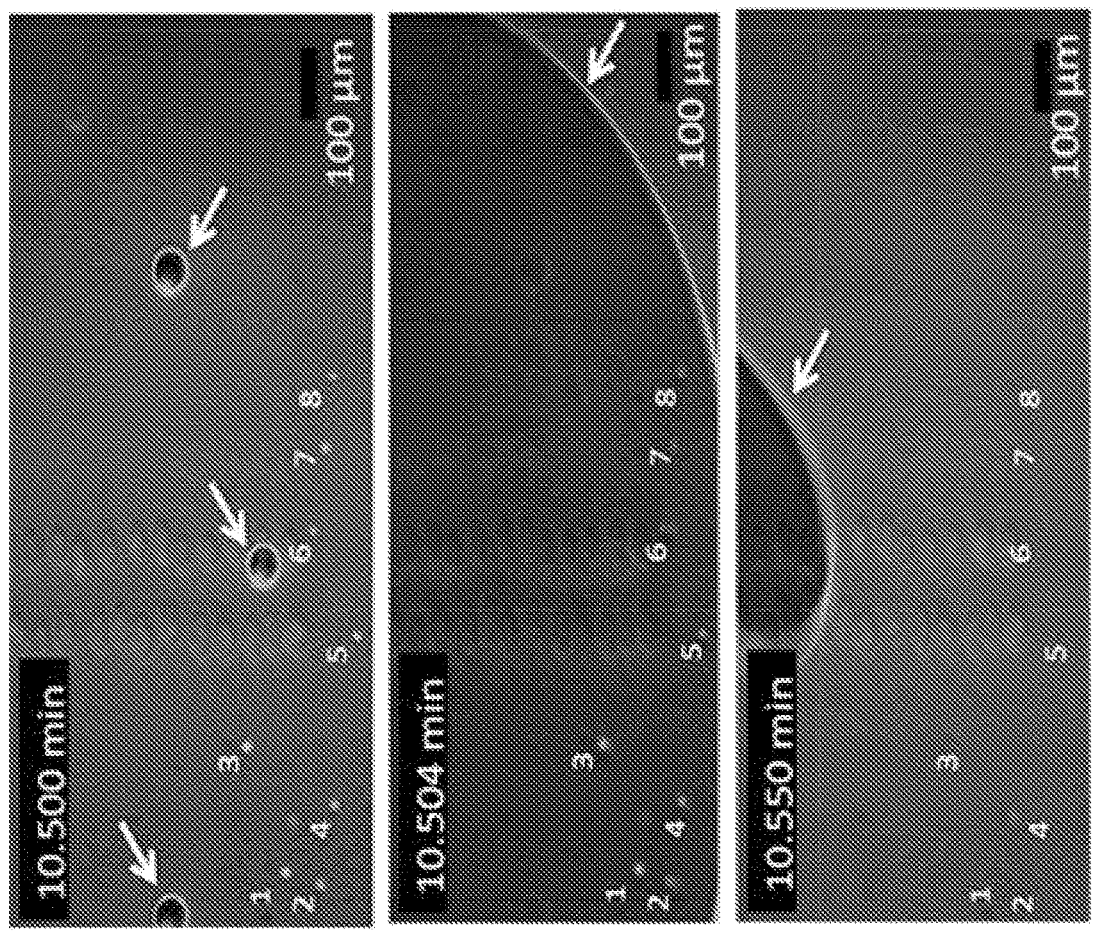
FIG. 14 provides a time-lapse micrograph of the releasing process.

The foamy solution is created by a mixture of air and cell culture medium (1:2 ratio by volume) and gently vortexing for 1 minute for foam creation. The micrographs of time-lapse experiments show that the captured HCT116 cells are released upon air-foam sweeping on them within seconds (FIG. 14, based on Chip E). FIG. 14 provides a time-lapsed micrographs of the releasing process. At t=10.500 min, pre-stained HCT116 cells (green dots marked with numbers) were captured on the surface. The 3 arrows point to existing small bubbles. At t=10.504 min, these cells were covered within the air phase of an incoming air bubble as it flowed through the area. The arrow points to the boundary of this large introduced bubble. At t=10.550 min, cells were released from the attachment sites and swept away by the outgoing bubble. The arrows point to fluorescent light reflected off interfacial boundary of tiny trapped air and the introduced larger air bubble. The average release efficiency using 250 uL foamy solution is 99.7% in 3 repeats as shown in Table 2.

Example 8: Culture and Maintenance of Viable Cells

Figure 16:
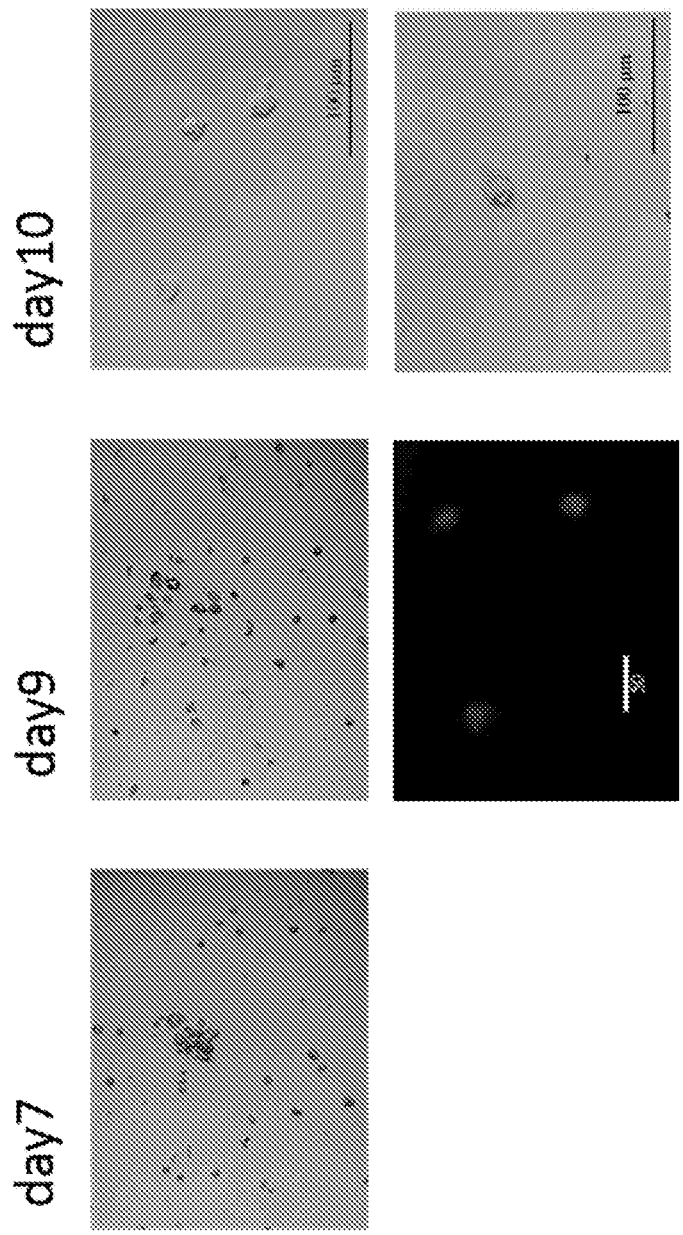
FIG. 16 shows cultivation of eluted CTCs and genetic mutation analyses.

To determine whether the isolated cells can be cultured in vitro, air foam released CTCs from clinical samples i collected and seeded onto 96-well tissue culture plates, incubated at 37° C. under 5% CO2. As shown in FIG. 16, cancer cells isolated from a stage III patient gather and attached to the bottom of plate at day 7 and became more spread out at day 9. Immunofluorescent staining shows DAPI (blue) and CK20 (red) positivity. To prove these cells have a propensity to re-attach, they are treated with 0.1% trypsin and re-seeded onto 96-well plate at day 9. After 1 day, these cells (day 10) re-attach to the substrate firmly with an apparent cell size ~25 um. The maintenance of CTC viability is observed.

Example 9: Molecular Analysis

To detect genetic mutations, the DNA is extracted directly from the eluted cells to perform castPCR for 7 high frequency cancer hotspots in P53, adenomatous polyposis coli (APC) and K-ras mutations as shown in Table 3.

TABLE 3

TaqMan ® Mutation assays

| Assay Name | Nucleotide mutation | Amino acid change | Mutation genome location |
|---|---|---|---|
| KRAS_520_mu | c.35G>T | p.G12V | chr.12 25398284-25398284 on NCBI build 37 |
| KRAS_532_mu | c.38G>A | p.G13D | chr.12 25398281-25398281 on NCBI build 37 |
| APC_13113_mu | c.3927_3931delAAAGA | p.E1309fs*4 | chr.5 112175218-112175222 on NCBI build 37 |
| APC_18561_mu | c.4666_4667insA | p.T1556fs*3 | chr.5 112175957-112175958 on NCBI build 37 |
| TP53_10656_mu | c.742C>T | p.R248W | chr.17 7577539-7577539 on NCBI build 37 |
| TP53_10662_mu | c.743G>A | p.R248Q | chr.17 7577538-7577538 on NCBI build 37 |
| TP53_10648_mu | c.524G>A | p.R175H | chr.17 7578406 on NCBI build 37 |

TABLE 2

Cell release efficiencies

| Exp no. | Number of cells captured by the chip | Cells remained in chip after air foam sweep | Release efficiency |
|---|---|---|---|
| 1 | 117 | 1 | 99.15% |
| 2 | 72 | 0 | 100% |
| 3 | 111 | 0 | 100% |

Figure 15:
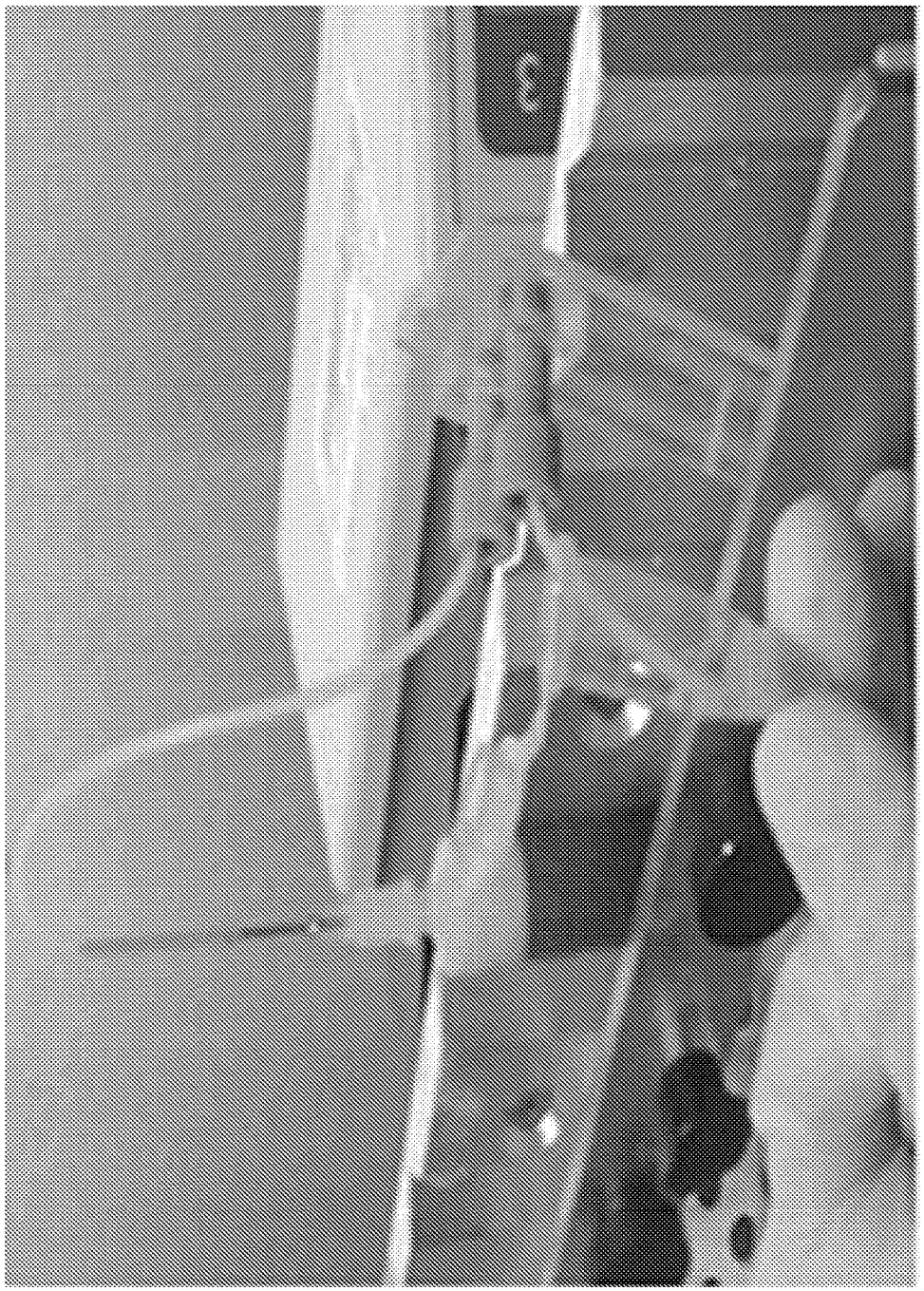
FIG. 15 provides cells released from the chip collected, along with the attached antibody and air foams, into an Eppendorf tube.

FIG. 15 shows that the eluted cell is wrapped by lipids, indicating cell release through peeling off SLB by air. Cells released from the chip were collected, along with the attached antibody and air foams, into an Eppendorf tube. Alternatively, eluted cells can be collected onto a planar porous membrane (shown diameter 10 mm) for immunofluorescent staining and enumeration. Live/Dead assay (Life Technologies) is performed immediately after cell elution; results showed 86% of eluted CTCs remaining viable as contrary to 0% viability from the conventionally coated anti-EpCAM silanized chip.

The result of 3 healthy donors are all negative (ΔCt>9.96); among 10 randomly selected CRC patients, 2 samples are positive (ΔCt<9.96) for TP53 R248Q and 3 are positive for APC1556fs*3.

Example 10: High Throughput Analysis of Clinical Sample

Figure 17:
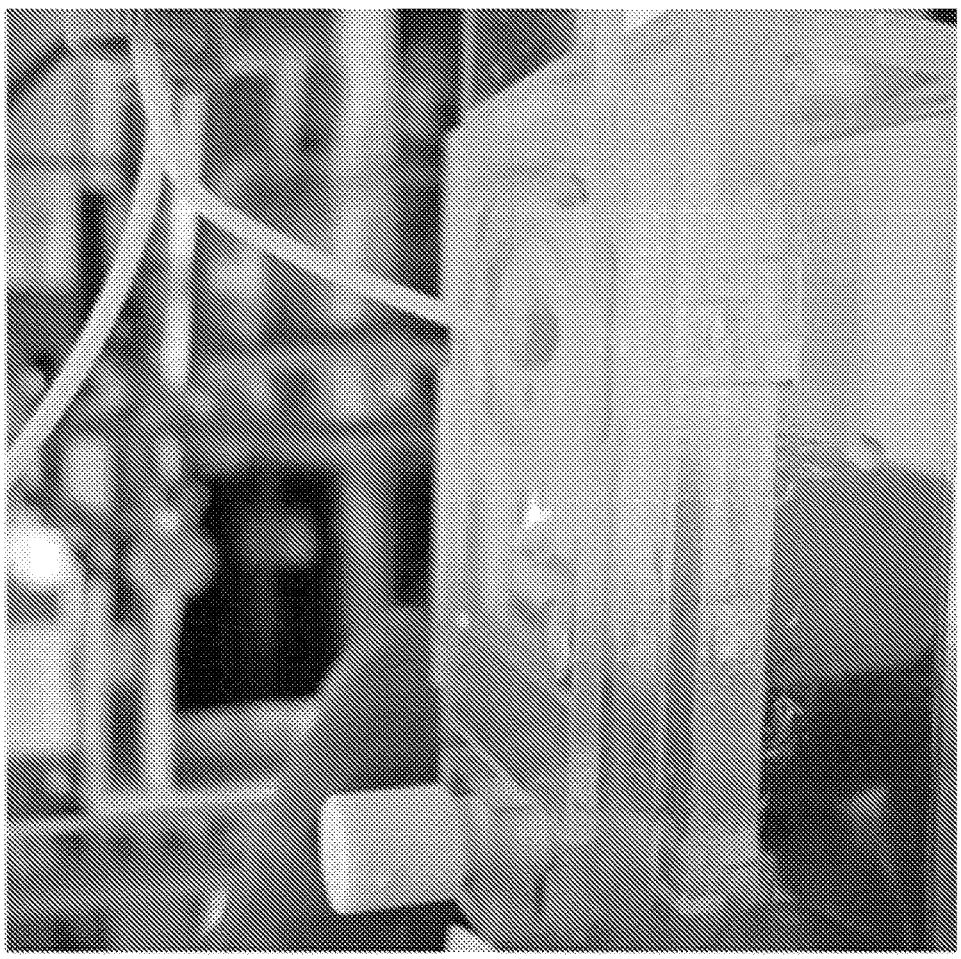
FIG. 17 illustrates cells collected on a small substrate.

An important advantage of easy cell release from a microfluidic device is that cells can be collected and stained on a small planar substrate. Instead of the in-chip inspection within the 3-dimensional complex microfluidic channels, imaging CTCs on a much smaller area (~10 mm in diameter) enables easy relocation of the cells of interests, and significantly reduce imaging and inspection time from 6 h to <0.5 h (FIG. 17). As a result, high throughput of clinical sample analysis becomes feasible.

Example 11: Analysis of CTCs in all Stages of Colorectal Cancers

CTCs are fairly rare in blood. The only FDA cleared assay for detecting and isolating CTC at this time is the CellSearch® assay from Veridex. In most patients, the Cell- Search® assay finds less than five CTCs per 7.5 ml of blood. Although CellSearch assay results demonstrate the clinical utility of counting CTCs in a patient sample as a prognosis marker, this utility is only adopted for cancers in late stages, not adoptable for all stages of cancer detection.

The device disclosed herein is useful for detecting all stages of cancers. An example is illustrated by the detection of CTCs from colorectal cancer patients of all stages. 110 CRC patients with stages 0/I (n=20), II (n=29), III (n=46) and IV (n=15) with no prior cancer therapy and colon disease-free donors negative controls (confirmed by colonoscopy, n=28) are included in a double blinded, prospective study.

Figure 18:
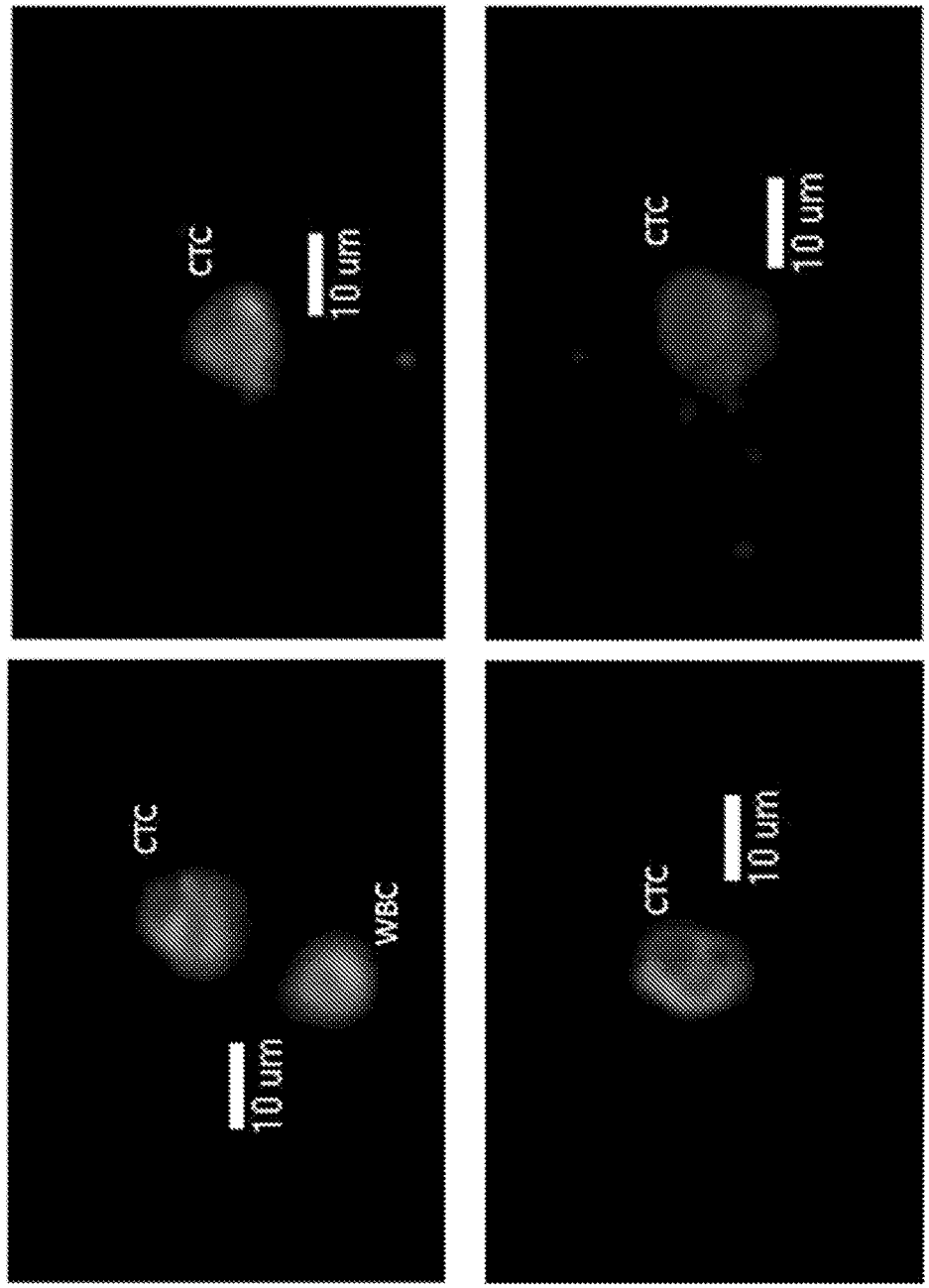
FIG. 18 illustrates cancer cells overlaid fluorescent images for cell identification.
Figure 19:
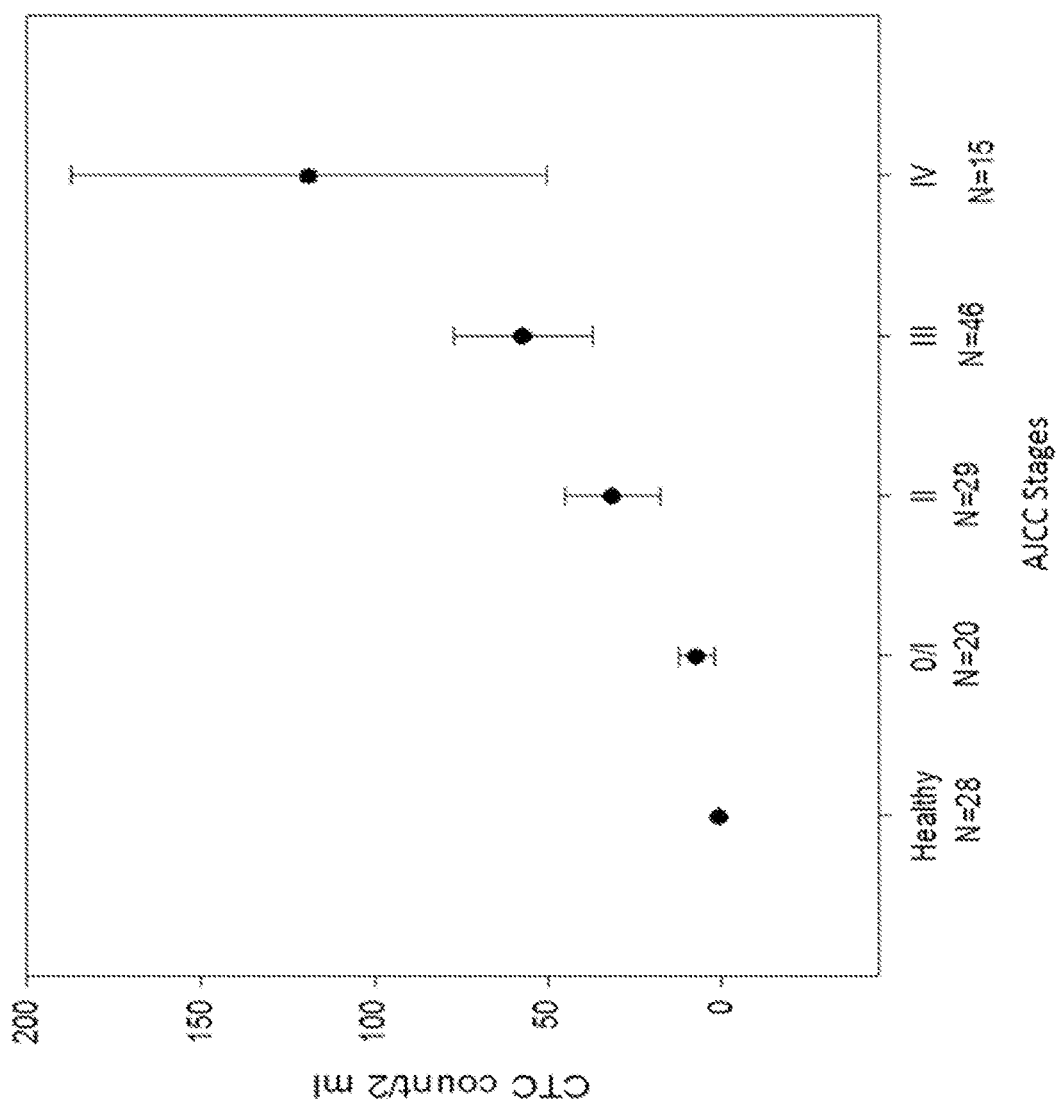
FIG. 19 illustrates CTC counts per 2 mL versus CRC disease TNM stages.
Figure 23:
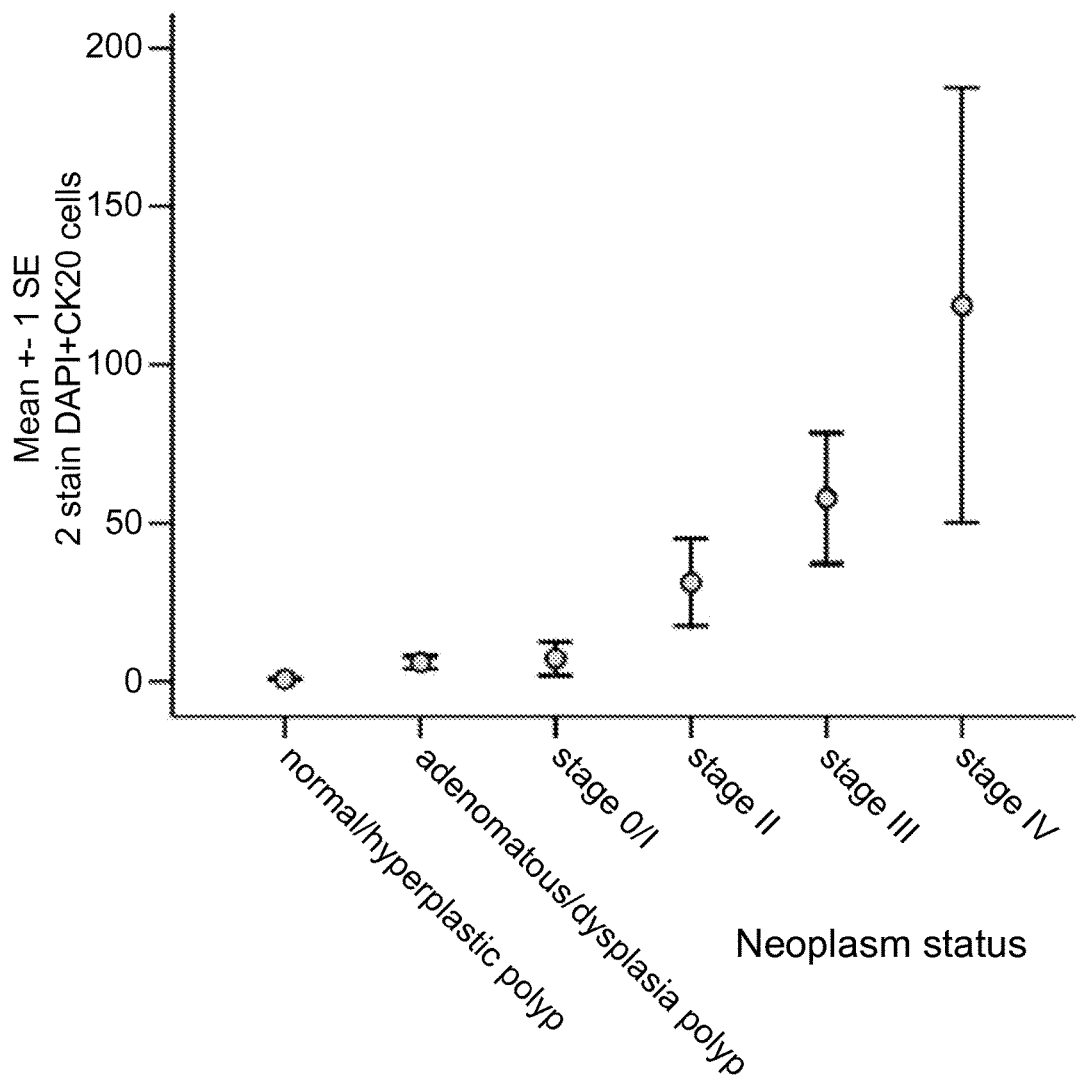
FIG. 23 illustrates the mean CTC number according to cancer progression.

Peripheral human blood is obtained from the CRC patients. After CTC capture and purification, air foam sweep is used to release captured CTCs onto a small membrane (~2 um) pore size to drain the excessive staining solutions) where immunofluorescent staining is performed to identify and enumerate the released cells (FIG. 18). We chose monoclonal antibody against cytokeratin 20 (CK20) as the positive staining marker as it is more colorectal-specific than pan-CKs. As shown in FIG. 19, patient CTCs, defined as DAPI+/CK20+/CD45-cells, increases with the advance of patient's disease stage. Among 28 healthy donors, the range of DAPI+/CK20+/CD45-cells is from 0 to 3. The median numbers of DAPI+/CK20+/CD45-cells in healthy, stage 0/I, stage II, stage III and stage IV are 0, 2, 4, 7, and 36, respectively. The CTC counts of stage IV is broadly distributed with the highest cell count exceeding 1000; the mean and standard deviation of each clinical stage were shown in FIG. 19. The mean of each clinical stage is plotted as shown in FIG. 23.

Example 12: Correlation of CTC Number with Colorectal Cancer and Gastrointestinal (GI) Tract Diseases To evaluate the correlation of CTC numbers with colorectal cancer (CRC) and gastrointestinal (GI) tract diseases, CTCs in peripheral blood obtained preoperatively from 120 cases with primary CRC are examined. We randomly select 60 cases without previous cancer history to perform CTC before colonoscopy examination as control. Among the 120 cancer patients, 10 patients (4 cases with stage IV and 6 cases with stage I to III) who had received preoperative concurrent chemotherapy and radiotherapy, chemotherapy or radiotherapy alone before CTC examination are excluded out for further analysis.

Classification of control group is basically according to the colonoscopic findings. At the classification of normal colon, three patients with peptic disease and one patients with endometrial polyp who received operation after CTC examination (also had the history of operation for parotic gland Castleman's disease 3 years ago before CTC examination) are classified into the sub-classification named as "had other site mucosa lesion". Two sub-classifications of diseased colon are classified according to the presence of polyp or not. However, two cases with polyps and ulcerative colitis are classified into the ulcerative group. One case with diverticular disease also suffered from cervical carcinoma in situ and received operative resection after CTC examination. One case with cecal focal severe dysplasia adenoma also suffered from ovary clear cell carcinoma (pathologic stage T2N0) and received operative resection of both tumors after CTC examination. For evaluating the correlation of circulating tumor cell presence to colonic neoplasm progression more precisely, we exclude out the patients belonged to the sub-classification of normal colon with other site mucosa lesion and diseased colon with other mucosa lesion for further analysis. In total, 161 cases (110 cancer and 51 control cases) are enrolled into the analysis of relationship between CTC and progression of colorectal neoplasm. The pathologic classification of TNM stage is according to AJCC 7th edition. Six cases of stage IV cancer does not receive surgical intervention. One case of stage 0 (Tis) only receives endoscopic mucosa resection. All other cases receive curative or intending curative resection of tumor. All the clinicopathologic parameters of patients are classified according to the chart records.

Statistical analysis is performed using SPSS for Windows (Version. 12.0, SPSS Inc, Chicago, Ill.). Two-independent-samples T test is used to compare the mean value of each group. Anova analysis is used to compare the mean and linearity between the subgroups of same parameter. Linear regression test is used to test the linear association between groups. Pearson's chi-square test is used to analyze the differences in incidence of positive rates over cutoff level between groups. All P-values are two-sided; P-values of less than 0.05 indicated statistical significance.

1) Distribution of CTC Number in Each Classification

The mean age of control group is 50.6±13.5 (range from 25 to 76) years old and significantly younger than 62.0±11.5 (range from 34 to 87) years old of cancer group (P<0.001). The ratio of female/male are 28/25 and 62/48 of control and cancer group respectively and there is no statistical difference between the two groups.

As summarized in Table 4, the mean values of CTC numbers in cancer group and diseased colon group are significantly higher than that of normal groups (P<0.01). The mean value of CTC in cancer group also is significantly higher than that of diseased group (P=0.01). In the cancer group, the detected CTC number is lower in patients who had received treatment before CTC examination than in those not.

TABLE 4

Number of CTC detected in control and cancer cases

| | | CK20+/CK45− cell No. | | |
|---|---|---|---|---|
| | Case No. | Mean ± SD | Range (Median) | >Cutoff level 2 No. (%) |
| Control cases | 60 | 2.8 ± 5.4 | 0~28 (1) | 16 (26.7) |
| Normal colon | 32 | 1.1 ± 1.6* | 0~6 (0) | 4 (12.5) |
| No other site mucosa lesion | 28 | 0.6 ± 0.9 | 0~3 (0) | 1 (3.6) |
| Had other site mucosa lesion | 4 | 4.3 ± 2.4 | 1~6 (5) | 3 (75) |
| Peptic disease | 3 | 3.7 ± 2.5 | 1~6 (4) | 2 (66.7) |
| Endometrial polyp | 1 | 6 | | 1 (100) |
| Dieseased colon | 28 | 4.9 ± 7.2* | 0~28 (1) | 12 (42.9) |
| Colorectal polyp | 23 | 4.9 ± 7.6 | 0~28 (1) | 9 (39.1) |
| Hyperplastic polyp | 6 | 1.3 ± 2.3 | 0~6 (0.5) | 1 (16.7) |
| Adenomatous polyp | 13 | 5.5 ± 7.0 | 0~21 (2) | 6 (46.2) |
| Severe dysplasia polyp | 4 | 8.5 ± 13.1 | 1~28 (2.5) | 2 (50) |
| Other mucosa lesion | 5 | 4.6 ± 6.0 | 0~15 (3) | 3 (60) |
| Ulcerative colitis | 3 | 1.3 ± 1.5 | 0~3 (1) | 1 (33.3) |
| Diverticular disease | 2 | 9.5 ± 7.8 | 4~15 (9.5) | 2 (100) |
| Colorectal cancer cases | 120 | 46.0 ± 135.0* | 0~1012 (4) | 71 (59.2) |

TABLE 4-continued

Number of CTC detected in control and cancer cases

| | | CK20+/CK45− cell No. | | |
|---|---|---|---|---|
| | Case No. | Mean ± SD | Range (Median) | >Cutoff level 2 No. (%) |
| No therapy before CTC test | 110 | 50 ± 140.6 | 0~1012 (5) | 69 (62.7) |
| Stage 0/I | 20 | 7.3 ± 23.8 | 0~108 (1) | 7 (35) |
| Stage II | 29 | 31.4 ± 73.7 | 0~381 (4) | 19 (65.5) |
| Stage III | 46 | 57.9 ± 140 | 0~699 (6.5) | 31 (67.4) |
| Stage IV | 15 | 118.7 ± 266 | 0~1012 (36) | 12 (80) |
| Had therapy before CTC test | 10 | 2.8 ± 4.6 | 0~14 (1) | 2 (20) |

*P < 0.05 when compared the mean value to each other.

2) Relationships Between CTC Number and Clinicopathologic Characteristics

In total, 110 CRC cases without treatment before CTC test are involved in this analysis. The mean CTC number increased gradually from T1 to T4 classification of tumor (Anova analysis, P=0.022), especially the mean CTC number of T4 significantly higher than other T classification (t test, P<0.01). The mean CTC number also increased gradually along with the tumor size and advancement of lymph node metastasis (Anova test, P<0.05). The mean CTC value of N2 is significantly higher than that of N0 or N1 classification (t test, P<0.01). The mean CTC value of tumor size over 5 cm also is significantly higher than that of tumor size smaller than 5 cm (t test, P<0.01). The mean CTC value of M1 is significantly higher than that of M0 classification (t test, P<0.01). These results reveal that the increase of CTC number in blood correlates well with the tumor progression named as TNM stage and tumor size. The mean CTC value of CEA elevation (>5) is higher than that of no CEA elevation but without statistical significance (t test, P=0.076). The mean CTC values is significantly higher in poor differentiated tumor than that in well or moderate differentiation one (t test, P<0.01). There is no difference of CTC value between well and moderate differentiation groups. The CTC presence is no difference between the different groups of sex, age and tumor location.

TABLE 5

CTC distribution in varied groups of cancer without previous therapy

| | Case No. | CK20+/CD45− | >cutoff level 2 (%) |
|---|---|---|---|
| Age | | | |
| <=70 | 82 | 54.8 ± 151.3 | 64.6 |
| >70 | 28 | 35.7 ± 104.2 | 57.1 |
| Sex | | | |
| Male | 62 | 50.5 ± 152.8 | 67.7 |
| Female | 48 | 42.9 ± 124 | 56.3 |
| Tumor location | | | |
| Colon | 73 | 58.6 ± 159.3 | 68.5 |
| Rectum | 37 | 32.9 ± 92.7 | 51.4 |
| CEA elevation | | | |
| <=5 | 75 | 39.2 ± 105.3 | 61.3 |
| >5 | 35 | 73.2 ± 196.1 | 65.7 |
| Tumor size | | | |
| <2 cm | 15 | 12.3 ± 28.5 | 46.7 |
| 2~5 cm | 60 | 24.1 ± 56.9 | 58.3 |
| >5 cm | 28 | 90.7 ± 183.2* | 71.4 |
| Gross type | | | |
| Polypoid | 15 | 32.5 ± 55.4 | 73.3 |
| Ulcerative | 78 | 43.2 ± 121 | 57.7 |
| Infiltrative | 3 | 69.3 ± 111.4 | 100 |
| T classification | | | |
| Tis | 4 | 4 ± 3.7 | 50 |
| T1 | 8 | 19.5 ± 38.4 | 37.5 |
| T2 | 12 | 10.4 ± 30.2 | 41.7 |
| T3 | 62 | 29.4 ± 84.5 | 62.9 |
| T4 | 17 | 119 ± 196.7* | 76.5 |
| N class | | | |
| N0 | 49 | 21.5 ± 57.5 | 53.1 |
| N1 | 26 | 27.7 ± 71.8 | 65.4 |
| N2 | 27 | 86.2 ± 178.6* | 66.7 |
| M class | | | |
| M0 | 95 | 39.1 ± 107.2 | 60 |
| M1 | 15 | 118.7 ± 266* | 80 |
| Histologic differentiation* | | | |
| Well | 5 | 12.0 ± 17.0 | 60 |
| Moderate | 81 | 35.3 ± 100 | 60.5 |
| Poor | 15 | 83.3 ± 162.6* | 66.7 |

*P < 0.05, t test

3) Presence of CTC in Stage IV Cancer Varied Type of Metastasis

Among the 19 stage IV cases, 4 cases had received treatment before CTC test. Although the detected CTC number is lower in patients with treatment than that of not, there is no statistical difference between the two groups. Among the 15 cases without treatment before CTC test, the detected CTC number of liver and lung metastasis is higher than that of peritoneal invasion and central lymph node metastasis (t test, P=0.076), as summarized in Table 6. That means the presence of CTC has the tendency to become more in hematospreading metastasis than peritoneal seeding or lymphatic route metastasis. There are 2 cases without previous treatment, had K-ras mutation in their primary tumor. One case with liver and lung metastasis cannot detect the existence of CTC. The other one with central lymph node metastasis has 2 CTC. The other patients without treatment before CTC test had wild type K-ras. So, it is doubtful that the CTC detection is related to K-ras mutation or not.

TABLE 6

CTC distriution in varied types of metastasis in stage IV cancer

| | | CK20+/CD45− | | |
|---|---|---|---|---|
| | Case No. | Mean | Range (Median) | >cutoff level 2 No. (%) |
| Total | 19 | | | |
| Had treatment befor CTC detection | 4 | 0.5 ± 0.6 | 0~1 (0.5) | 0 (0) |
| CCRT | 3 | 0.33 ± 0.6 | 0~1 (0) | 0 (0) |
| Chemotherapy | 1 | 1 | | 0 (0) |

TABLE 6-continued

CTC distriution in varied types of metastasis in stage IV cancer

| | | CK20+/CD45− | | |
|---|---|---|---|---|
| | Case No. | Mean | Range (Median) | >cutoff level 2 No. (%) |
| No treatment before CTC detection | 15 | 118.7 ± 266 | 0~1012 (36) | 12 (80) |
| Liver metastasis | 8 | 207.9 ± 348.8 | 3~1012 (50) | 8 (100) |
| Lung metastasis | 1 | 36 | | 1 (100) |
| Liver and lung metastasis | 1 | 0 | | 0 (0) |
| Peritoneal invasion | 3 | 25.3 ± 21.6 | 1~42 (33) | 2 (66.7) |
| Central LN metastasis | 2 | 3 ± 3 | 2~4 (3) | 1 (50) |

It may be observed that the hematogenous spreading metastais has more CTCs number than peritoneal or LN metastasis. The one case with liver and lung metastasis has cervical cancer with intra-abdominal invasion and has K-ras mutation and poor differentiation of tumor. One case (D-colon cancer) among the liver metastasis group had 3 CTCs, just equal to cutoff level and CEA=1.1. Among the 19 cases with stage IV, 13 cases are with palliative resection of primary and metastatic tumors.

TABLE 7

Characteristics of control and patients with colorectal cancer

| | Control | Cancer |
|---|---|---|
| Case number | 60 | 120 |
| Age | | |
| Mean | 50.8 ± 13.7 | 62.2 ± 11.4* |
| Range | 25~76 | 34~87 |
| Sex | | |
| Male | 32 | 69 |
| Female | 28 | 51 |
| Colonoscopy findings | | |
| Normal | 28 | |
| Others wihtout CRC | 32 | |
| Colon polyp | 25 | |
| Colitis | 2 | |
| Other peptic disease | 3 | |
| Other neoplasm | 2 | |
| Cancer status | | |
| No treatment before CTC test | | 110 |
| Colon cancer | | 73 |
| Rectum | | 37 |
| Had treatment before CTC test | | 10 |
| Colon cancer (chemotherapy) | | 1 |
| Rectal cancer | | 9 |
| CCRT | | 8 |
| Radiotherapy only | | 1 |

TABLE 8

Data of CK20+/CD45− and CK20+/CD45+ cells

| | | CK20+/CK45− cell No. | | |
|---|---|---|---|---|
| | Case No. | Mean ± SD | Range (Median) | >Cutoff level 2 No. (%) |
| Control cases | 60 | 2.8 ± 5.4* | 0~28 (1) | 16 (26.7) |
| Normal | 28 | 0.6 ± 0.9 | 0~3 (0) | 1 (3.6) |
| Colorectal polyp | 25 | 4.6 ± 7.3 | 0~28 (1) | 10 (40) |
| Hyperplastic polyp | 7 | 1.1 ± 5.5 | 0~6 (0) | 1 (14.3) |
| Adenomatous polyp | 13 | 5.5 ± 7.0 | 0~21 (2) | 6 (46.2) |
| Dysplasia polyp | 5 | 7.4 ± 11.6 | 1~28 (3) | 3 (60) |
| Other conditions | 7 | 5.3 ± 4.8 | 1~15 (4) | 5 (71) |
| Colitis | 2 | 8.0 ± 9.9 | 1~15 (8) | 1 (50) |
| Peptic disease | 3 | 3.7 ± 2.5 | 1~6 (5) | 2 (66.7) |
| Other neoplasm | 2 | 5.0 ± 1.4 | 4~6 (2) | 2 (100) |
| Colorectal cancer cases | 120 | 46.0 ± 135.0* | 0~1012 (4) | 71 (59.2) |
| No therapy before CTC test | 110 | 50 ± 140.6** | 0~1012 (5) | 69 (62.7) |
| Stage 0/I | 20 | 7.3 ± 23.8 | 0~108 (1) | 7 (35) |
| Stage II | 29 | 31.4 ± 73.7 | 0~381 (4) | 19 (65.5) |
| Stage III | 46 | 57.9 ± 140 | 0~699 (6.5) | 31 (67.4) |
| Stage IV | 15 | 118.7 ± 266 | 0~1012 (36) | 12 (80) |
| Had therapy before CTC test | 10 | 2.8 ± 4.6** | 0~14 (1) | 2 (20) |

*P < 0.05 when compared to each other.
**P < 0.05 when compared to each other.

TABLE 9

CTC distribution in varied groups of cancer without previous therapy

| | Case No. | CK20+/CD45− | >cutoff level 2 (%) |
|---|---|---|---|
| Age | | | |
| <=70 | 82 | 54.8 ± 151.3 | 64.6 |
| >70 | 28 | 35.7 ± 104.2* | 57.1 |
| Sex | | | |
| Male | 62 | 50.5 ± 152.8 | 67.7 |
| Female | 48 | 42.9 ± 124* | 56.3 |
| Tumor location | | | |
| Colon | 73 | 58.6 ± 159.3 | 68.5 |
| Rectum | 37 | 32.9 ± 92.7* | 51.4 |
| CEA elevation | | | |
| <=5 | 75 | 39.2 ± 105.3 | 61.3 |
| >5 | 35 | 73.2 ± 196.1* | 65.7 |
| Tumor size | | | |
| <2 cm | 15 | 12.3 ± 28.5 | 46.7 |
| 2~5 cm | 60 | 24.1 ± 56.9 | 58.3 |
| >5 cm | 28 | 90.7 ± 183.2 | 71.4 |
| Gross type | | | |
| Polypoid | 15 | 32.5 ± 55.4 | 73.3 |
| Ulcerative | 78 | 43.2 ± 121 | 57.7 |
| Infiltrative | 3 | 69.3 ± 111.4 | 100 |
| T classification | | | |
| Tis | 4 | 4 ± 3.7 | 50 |
| T1 | 8 | 19.5 ± 38.4 | 37.5 |
| T2 | 12 | 10.4 ± 30.2 | 41.7 |

TABLE 9-continued

CTC distribution in varied groups
of cancer without previous therapy

|  | Case No. | CK20+/CD45− | >cutoff level 2 (%) |
|---|---|---|---|
| T3 | 62 | 29.4 ± 84.5 | 62.9 |
| T4 | 17 | 119 ± 196.7 | 76.5 |
| N class |  |  |  |
| N0 | 49 | 21.5 ± 57.5 | 53.1 |
| N1 | 26 | 27.7 ± 71.8 | 65.4 |
| N2 | 27 | 86.2 ± 178.6 | 66.7 |
| M class |  |  |  |
| M0 | 95 | 39.1 ± 107.2 | 60 |
| M1 | 15 | 118.7 ± 266* | 80 |
| Histologic differentiation* |  |  |  |
| Well | 5 | 12.0 ± 17.0 | 60 |
| Moderate | 81 | 35.3 ± 100 | 60.5 |
| Poor | 15 | 83.3 ± 162.6 | 66.7 |

*P < 0.05 Mann-Whitney test

N2 was significant higher in CTC than N0 and N1 group.

TABLE 10

CTC distribution in patients with short
course radiotherapy or long course CCRT

|  |  | CK20+/CK45− cell No. |  |
|---|---|---|---|
|  | Case No. | Mean ± SD | Range (Median) |
| Total | 6 | 4.4 ± 5.5 | 0~14 (1.5) |
| CCRT | 5 |  |  |
| Stage I | 1 |  | 8 |
| Stage II | 1 |  | 2 |
| Stage III | 3 |  | 1 |
|  |  |  | 1 |
|  |  |  | 14 |
| Short course RT | 1 |  |  |
| stage III | 1 |  | 0 |

As a comparison, the widely used Veridex CellSearch CTC enumeration system demonstrated a detection sensitivity of ≥3 CTCs per 7.5 mL blood (defined as DAPI+/panCK+/CD45−) at only 25% of stage IV CRC patients50. Our platform showed that using ≥3 CTC (DAPI+/CK20+/CD45−) per 2 mL blood as a cutoff, 80%, 67%, 66%, and 30% of CRC stages IV, III, II, and I/0 are positive, on the contrary, only one of 28 healthy donors (4%) has 3 CTC (the rest had 0~2 CTCs). With this level of sensitivity and specificity, we showed that CTCs can be detected at early stages and the quantity correlates with disease progression.

Figure 24:
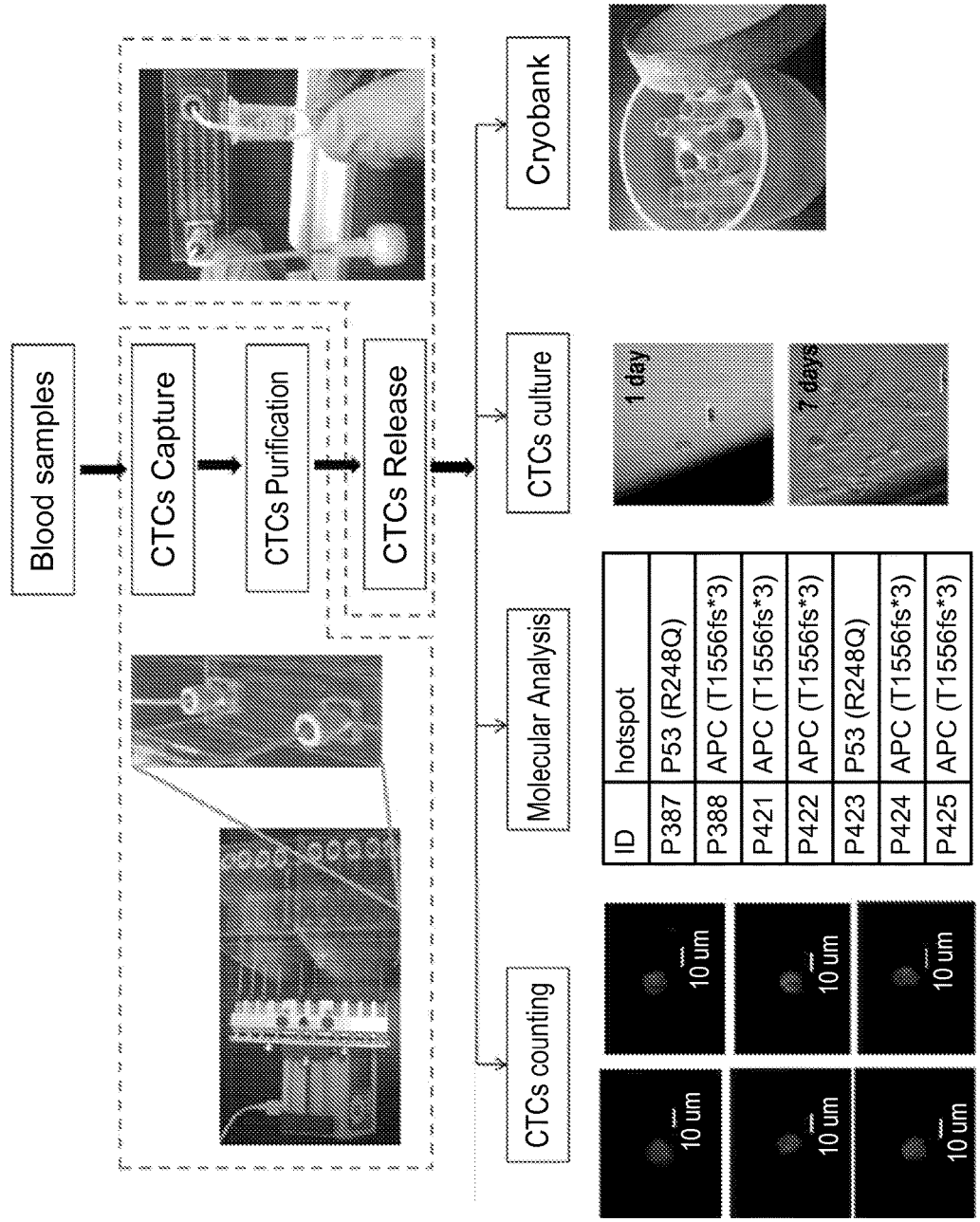
FIG. 24 illustrates a simple workflow of the system.

A typical 1 mL blood sample contains ~6.6×106 nucleated WBCs, and the SLB coated microfluidic system eliminates 99.9962% on average. Currently there are ~500-2000 WBCs eluted with the CTCs due to gentle wash at flow rate of 4 mL/h, and the dead volume in the fluidic device and tubing. Nevertheless, this purity level of CTCs is sufficient to facilitate molecular analyses for oncogene identification (0.1% purity for cast PCR) and possibly offer benefits of early intervention using appropriately selected therapy. As shown in FIG. 24, a simple workflow of our system performs capture, purification and release in a continuous and parallel process economically. 8 mL blood sample, split equally into 4 aliquots, were fed into 4 chips in parallel. All chips went through cell capture, purification and then cells were released for one of many downstream applications, including IF staining, cell counting, PCR hotspot analysis, cell culture and/or cryobanking. The platform offers the complete solution for CTC research for imaging, molecular analysis, cell culture and preservation simultaneously, only requiring total 8 mL of blood. This opens up the opportunity for the routine clinical utility of CTCs in cancer screening, monitoring, molecular profiling and drug selection.

Example 13: Predicting Early Liver Metastases after Operation

From Jul. 4, 2012 to Nov. 1, 2012, randomly selected 110 patients with primary CRC and 50 healthy donors without previously known cancer history upon colonoscopy examination were recruited in Chang Gung Memorial Hospital, Linkou Campus. The prospective study is double-blinded upon the blood drawn and CTC enumeration. All the 110 cancer patients had not received any prior treatment upon the blood drawn. Clinical status of non-metastatic CRC patients was followed up until November 2014, including serial serum CEA measurements every 3 months, abdominal sonography or CT scan, chest X-ray, and colonoscopy every 12 months or the time of suspected metastasis by clinical symptom or CEA elevation.

Classification of control group is based on the colonoscopic findings and chart records. The pathologic classification of TNM stage is based on AJCC 7th edition. Except one case without surgical resection, all other non-metastatic cases had received curative or intending curative resection of tumor. All the clinicopathologic parameters of patients are classified according to the chart records. Informed consent with IRB approval (No. 100-4274B of Ethic Committee of Chang Gung Memorial Hospital, and AS-IRB01-11056 in Academia Sinica) had been obtained from all cases before examination.

The CMx platform was used for CTC isolation and enrichment. The procedures of this method were described briefly as below. First, about 7~9 mL peripheral blood samples from donors were drawn and collected into 10 ml Vacutainer tubes containing the anticoagulant EDTA (BD Biosciences), then 2 mL of blood was infused into the anti-EpCAM-SLB coated chip with a flow-rate of 1.5 mL/h. After the completion of the blood infusion, the PBS buffer was used to wash out the loosely bound cells; subsequently, air foam was infused to the chip to disintegrate the SLB thus eluting the captured cells. The released cells were stained with DAPI, CK20, and CD45. The round particle with cell morphology and within 7-25 um in diameter with CK20 positive in cytoplasm, DAPI positive in nucleus and CD45 negative stain are defined as CTCs and counted under microscopy of Leica DM-IRE2 (Automatic Inverted Microscope and Living Cell System) and Leica AF 6000 (Advanced Fluorescence Imaging System). At least two trained operators independently assessed the cell image and the CTCs were counted based on consensus.

Statistical analysis was performed using SPSS for Windows (Version. 12.0, SPSS Inc, Chicago, Ill.). Two-independent-samples T test and Anova analysis was used to compare the mean value and linearity between different groups. Linear regression test was used to test the linear association between groups. Pearson's chi-square test was used to analyze the differences in incidence of positive rates between groups. Survival analysis was performed by Kaplan-Meier method and Log-rank test. Cox-regression model was used to multivariate analysis of prognosis factors. All P-values were two-sided; P-values of less than 0.05 indicated statistical significance.

Example 14: Microfluidic Chip Preparation

The fabrication of custom microfluidic chips is described as follows: A commercial CO2 laser scriber (Helix 24, Epilog, USA) is used to create micropatterns on the poly (methyl methacrylate (PMMA) slide (size=standard slide, thickness=1.5 mm). The laser is also used to engrave a 63 um-thick adhesive double sided tape (8018PT, 3M Corp) to carve out the borders surrounding the microfluidic patterns on the PMMA. The microtrenched patterns and microstructures on PMMA slide were drawn using CorelDraw (Corel, Ottawa, Canada) and then transferred to the laser scriber for direct machining on the substrate. In this study, six types of chips were prepared. The engraved chips were bonded with plasma treated glass slide by placing the carved out 3M adhesive tape (sandwiched) between the top (PMMA slide) and a glass slide on the bottom to form sealed channels. The preparation of lipid vesicles, biotinylation of antibody of EpCAM, EpAb4-1, the sequential preparation of anti-EpCAM-supported lipid bilayer coating in the microfluidic chip are described previously but are briefly described herein.

The inner walls of the microfluidic channels are treated with lipid vesicles consisting of 1-palmitoyl-2-oleoyl-sn-glycero-3-phosphocholine (POPC) and 1,2-dipalmitoyl-sn-glycero-3-phosphoethanolamine-N-cap-biotinyl (b-PE) in molar ratios of 95/5. After removal of excess lipids, Neutravidin™ (NA) was conjugated to the b-PE in the SLB via NA-biotin recognition, followed by conjugation of biotinylated EpAb4-1 (b-EpAb4-1) to the NA to complete the surface formation. FIG. 9 shows a series of microfluidic devices with different flow paths, dimensions and microstructures with this surface modification.

Example 15: Colorectal Cancer Cell Line Capture Efficiency Study

Colorectal cancer cell line capture efficiency was characterized using HCT116. 300 to 2000 HCT116 cells pre-stained with CellTracker Green were spiked into glass-bottomed wells (Diameter: 6 mm, Height: 5 mm) and waited 10 min for cells to settle down. Well plate bottoms were imaged before and after cells were transferred to the whole blood collected from healthy individuals by fluorescence microscopy (Leica AF 6000 Advanced Fluorescence Imaging system) to ensure accurate counts. The actual number of spiked cells were defined as (cell number in well before transfer) minus (cell number remaining in well after transfer). After proper, gentle mixing, the cell-blood mixture was flowed through the functionalized microchannel. Afterward, the microchannel was washed with 0.5 mL of PBS and 0.3 mL of Hoechst solution (1 µg/mL in PBS) was introduced to stain the cell nuclei. The channel was fluorescently photomicrographed to enumerate total number of cells captured in the channel. Colorectal cancer cell line capture efficiency was defined as (number of confirmed captured cells)/(number of actual spiked cells)×100%.

Example 16: Clinical Sample Selection and Immunofluorescence Staining of CTCs for Clinical Samples & Genotyping Using castPCR Technology One tube each of peripheral blood was obtained from 110 patients with stage 0~IV colorectal cancer and 28 healthy donors (62 female and 76 male). The colorectal cancer patients were accepted in this study having no prior cancer treatments, receiving blood draw prior to the surgery on the same day or a day before. The healthy donors were confirmed by colonoscopy examination with no colon disease and received blood draw before the procedure. Average ages of patients and healthy donors are 62 and 44 years old. The study protocol was approved by the Institutional Review Boards of Academia Sinica (AS•IRBOI-12040) and Chang Gung Memorial Hospital (100-1023B).

Figure 21:
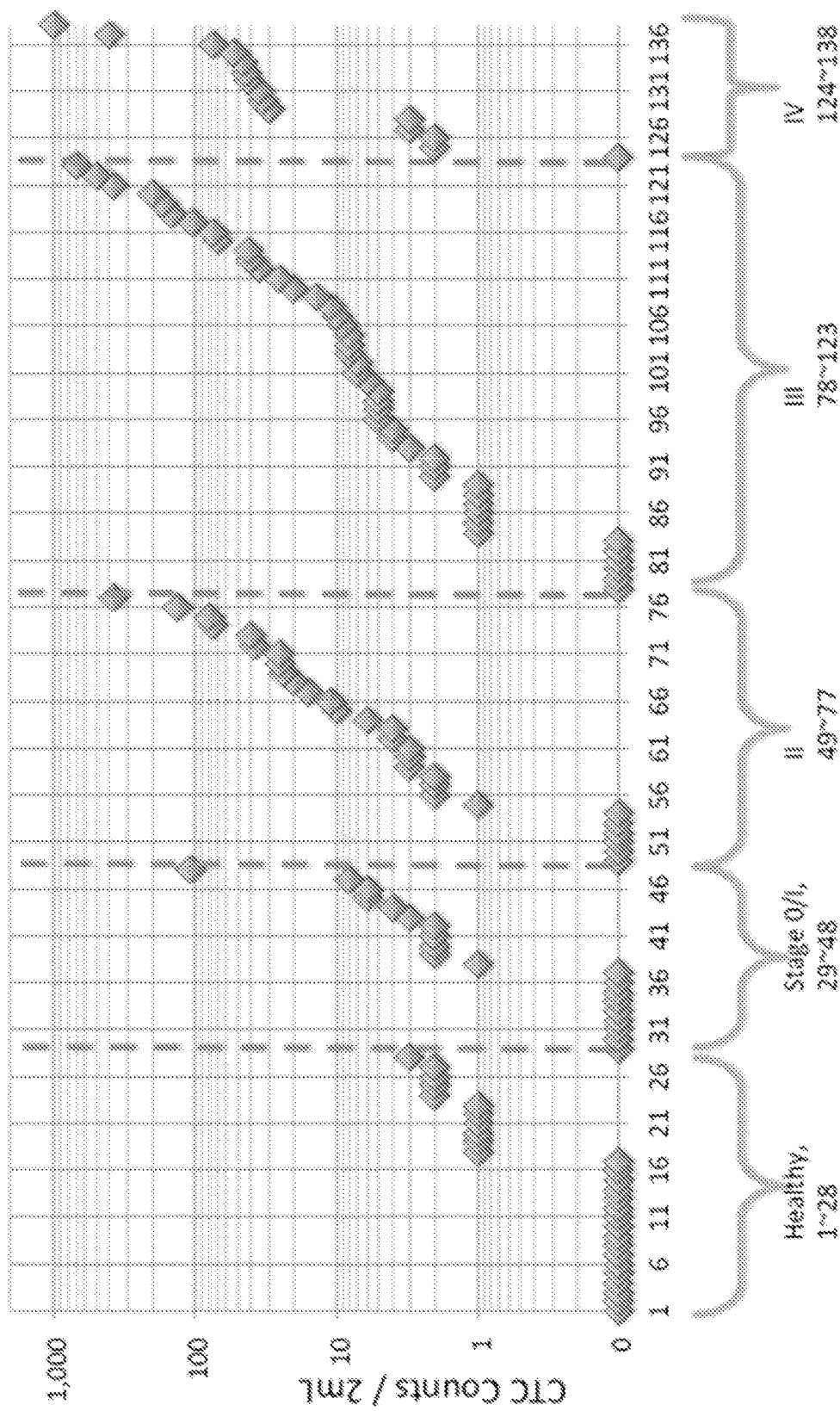
FIG. 21 shows CTC counts per 2 mL of peripheral blood for all subjects from healthy donors to colorectal cancer patients with TNM stages from 0/I, II, III to IV.

The captured cells, released from chip onto the filter membrane, were fixed with 4% paraformaldehyde (PFA), permeabilized with 0.1% triton X-100 in 1×PBS, and blocked with BSA. Subsequently, cells were stained with rabbit anti-human cytokeratin 20 (CK20) (Abcam, Cambridge, UK) and rat anti-human CD45 (Abcam Cambridge, UK) overnight at 4° C. and followed by PBS washing. After PBS washing, cells were incubated with the FITC conjugated goat anti-rat IgG antibody (Abcam Cambridge, UK) and the Alexa Fluor® 568 anti-rabbit IgG antibody (Life Technologies, Calif., USA) for 1 h at room temp, following by PBS washing to remove the excess secondary antibody. The CTC counts are summarized in FIG. 21.

KRAS, TP53 and APC mutation status were detected by commercially available TaqMan® mutation detection assay (Life Technologies, Carlsbad, Calif.). These assays use competitive allele-specific TaqMan PCR (castPCR technology). Each wild-type or mutant allele assay composed of a modified or unmodified allele-specific forward primer, locus-specific TaqMan® probe, locus specific reverse primer, and allele-specific MGB blocker. Each test sample was run with a mutant allele assay(s) and the corresponding gene reference assay. Results were analyzed with the Seq Detection System version 2.3 to generate the values of $CT_{target}$ and $CT_{reference}$. The detection ΔCT cutoff value is used to determine the limit of the percent mutation in a sample that the mutant allele assay can detect. The conversion formula between % and ΔCT is 2−(ΔCT)×100%. The mutant allele assay sensitivity was 0.1%. Therefore, the value of ΔCT<9.96 is positive and the value of ΔCT>9.96 is negative.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of releasing target cells from a blood sample captured on a surface of a microfluidic channel, the method comprising:

flowing a foam composition across the surface, wherein the surface comprises a lipid bi-layer coupled to a binding moiety selective for said target cells and the target cells are captured in association with said binding moiety coupled to the lipid bi-layer; and detaching at least a part of the lipid bi-layer, thereby releasing the target cells captured on the lipid bi-layer, wherein the foam composition comprises a plurality of air bubbles, a majority of which has a diameter smaller than a width of the microfluidic channel or a height of the microfluidic channel.

2. The method of claim 1, wherein the captured target cells are released with at least 40% efficiency and 40% viability.

3. The method of claim 1, further comprising a) staining the target cells with a panel of antibodies and b) identifying an origin source based on the staining result.

4. The method of claim 3, wherein the panel of antibodies comprises at least two of anti-panCK, anti-CK18, anti-CK7, anti-TTF-1, anti-CK20 mixed with anti-CDX-2, anti-PSA mixed with anti-PSMA.

5. The method of claim 1, further comprising analyzing the released target cells thereby assessing a presence, absence, severity, metastasis, or tissue of origin of a condition in a subject.

6. The method of claim 5, wherein the condition is cancer and assessing the severity comprises determining a cancer stage.

7. The method of claim 5, wherein the target cells are CTCs, and wherein analyzing comprises enumerating CTCs, enumerating viable CTCs, or performing a molecular analysis assay on the CTCs.

8. The method of claim 5, wherein the analyzing comprises comparing a number of released viable target cells to a cutoff value.

9. The method of claim 1, wherein the blood sample has a volume equal to or less than 6 mL.

10. The method of claim 9, wherein the blood sample has a volume equal to or less than 2 mL.

11. The method of claim 1, wherein at least 50% of said air bubbles comprise a diameter from 10 to 100 microns.

12. The method of claim 1, wherein the majority of the air bubbles has a diameter smaller than ½ a width of the microfluidic channel or ½ a height of the microfluidic channel.

13. The method of claim 1, wherein said flowing comprises flowing the foam composition at a linear velocity of at least 2.5 mm/s.

14. The method of claim 1, wherein said flowing comprises flowing the foam composition at a linear velocity of at most 4 mm/s.

15. The method of claim 1, wherein said flowing removes greater than 60% of said lipid bi-layer.

16. The method of claim 1, wherein a ratio of liquid to air in said composition is at least 1.5:1.

17. The method of claim 1, wherein the foam composition comprises a protein-containing solution mixed with air.

\* \* \* \* \*